United States Patent
Sullenger et al.

(10) Patent No.: US 9,687,529 B2
(45) Date of Patent: Jun. 27, 2017

(54) METHOD OF CONTROLLING COAGULATION

(75) Inventors: Bruce A Sullenger, Durham, NC (US); Jens Lohrmann, Durham, NC (US); James Frederiksen, Durham, NC (US); Kristin Bompiani, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 14/115,797

(22) PCT Filed: May 7, 2012

(86) PCT No.: PCT/US2012/036783
§ 371 (c)(1),
(2), (4) Date: Nov. 5, 2013

(87) PCT Pub. No.: WO2012/151575
PCT Pub. Date: Nov. 8, 2012

(65) Prior Publication Data
US 2014/0275226 A1    Sep. 18, 2014

Related U.S. Application Data

(60) Provisional application No. 61/457,642, filed on May 5, 2011.

(51) Int. Cl.
| | | |
|---|---|---|
| A61K 48/00 | (2006.01) | |
| C07H 21/02 | (2006.01) | |
| C07H 21/04 | (2006.01) | |
| A61K 38/36 | (2006.01) | |
| C12N 15/115 | (2010.01) | |
| A61K 38/58 | (2006.01) | |
| A61K 45/06 | (2006.01) | |
| A61K 31/7088 | (2006.01) | |
| A61K 31/702 | (2006.01) | |
| A61K 31/713 | (2006.01) | |

(52) U.S. Cl.
CPC ............ *A61K 38/36* (2013.01); *A61K 31/702* (2013.01); *A61K 31/7088* (2013.01); *A61K 31/713* (2013.01); *A61K 38/58* (2013.01); *A61K 45/06* (2013.01); *C12N 15/115* (2013.01); *C12N 2310/113* (2013.01); *C12N 2310/16* (2013.01); *C12N 2310/51* (2013.01); *C12N 2320/31* (2013.01); *C12N 2320/53* (2013.01)

(58) Field of Classification Search
CPC .............................. C12N 15/113; A61K 48/00
See application file for complete search history.

(56) References Cited

U.S. PATENT DOCUMENTS

| | | | |
|---|---|---|---|
| 5,660,985 A | 8/1997 | Pieken et al. | |
| 5,756,291 A | 5/1998 | Griffin et al. | |
| 5,770,198 A | 6/1998 | Coller et al. | |
| 6,376,190 B1 | 4/2002 | Gold et al. | |
| 6,855,496 B2 | 2/2005 | Pagratis et al. | |
| 7,300,922 B2 | 11/2007 | Sullenger et al. | |
| 7,312,325 B2 | 12/2007 | Sullenger et al. | |
| 7,566,701 B2 | 7/2009 | Diener et al. | |
| 7,741,307 B2 | 6/2010 | Sullenger et al. | |
| 7,776,836 B2 | 8/2010 | Sullenger et al. | |
| 8,367,627 B2 | 2/2013 | Sullenger et al. | |
| 8,790,924 B2 | 7/2014 | Sullenger et al. | |
| 2003/0083294 A1 | 5/2003 | Sullenger et al. | |
| 2003/0153506 A1 | 8/2003 | Bylund et al. | |
| 2003/0158120 A1 | 8/2003 | Mattsson | |
| 2003/0175703 A1 | 9/2003 | Sullenger et al. | |
| 2005/0176940 A1 | 8/2005 | King | |
| 2006/0193821 A1 | 8/2006 | Diener et al. | |
| 2006/0246123 A1 | 11/2006 | Gilboa et al. | |
| 2006/0264369 A1 | 11/2006 | Diener et al. | |
| 2008/0220055 A1 | 9/2008 | Ludwig et al. | |
| 2010/0003244 A1 | 1/2010 | Munch et al. | |
| 2010/0184822 A1* | 7/2010 | Sullenger ............... A61K 31/00 514/44 A |
| 2010/0297654 A1* | 11/2010 | Heyduk ................. C12N 15/111 435/6.11 |
| 2010/0311820 A1 | 12/2010 | Layzer et al. | |
| 2010/0324120 A1* | 12/2010 | Chen .................... A61K 9/1272 514/44 A |
| 2011/0118187 A1 | 5/2011 | Sullenger et al. | |
| 2012/0183564 A1 | 7/2012 | Sullenger | |
| 2014/0050717 A1* | 2/2014 | Dockal ................. A61K 31/727 424/94.64 |

FOREIGN PATENT DOCUMENTS

WO    WO 2007035532    3/2007

OTHER PUBLICATIONS

International Search Report for PCT/US2012/036783, mailed Nov. 23, 2012.
Written Opinion of the International Searching Authority for PCT/US2012/036783, mailed Nov. 23, 2012.
Mackman, N., "Triggers, targets and treatments for thrombosis", Nature, vol. 451, No. 7181, (Feb. 21, 2008), pp. 914-918, (Author Manuscript).
Rusconi, C.P. et al., "Antidote-mediated control of an anticoagulant aptamer in vivo", Nature Biotechnology, vol. 22, No. 11, (Nov. 2004), pp. 1423-1428.
Bompiani et al. "Probing the Coagulation Pathway with Aptamers Identifies Combinations that Synergistically Inhibit Blood Clot Formation" (2014) Chemistry & Biology 21: 935-944.
Dougan et al., "Evaluation of DNA aptamers directed to thrombin as potnetial thrombus imaging agents," (2003) Nuclear Medicine and Biology 30:61-72.
Franciscis et al., "Nucleic Acid Aptamers for In Vivo Molecular Imaging," (2012) Molecular Imaging Chapter 5.

(Continued)

*Primary Examiner* — Amy Bowman
(74) *Attorney, Agent, or Firm* — Andrus Intellectual Property Law, LLP

(57) ABSTRACT

The present invention relates, in general, to methods of controlling coagulation, and in particular, to methods of effecting neutralizable rapid onset anticoagulation, and to compounds and compositions suitable for use in such methods.

17 Claims, 53 Drawing Sheets

(56) References Cited

OTHER PUBLICATIONS

Kiefer, T.L. et al., "Inhibitors of platelet adhesion," (2009) Circulation 120:2488-2495.
Li, M. et al., "Selecting aptamers for a glycoprotein through the incorporation of the boronic acid moiety," (2008) J. Am. Chem. Soc.130(38):12636-12638.
Long, S.B., et al., "Crystal Structure of an RNA aptamer bound to thrombin," (2008) RNA 14:2504-2512.
Oney, et al., "Antidote-controlled platelet inhibition targeting von Willebrand factor with aptamers," (2007) Oligonucleotides 17(3):265-274—Abstract.
White, R. et al., "Generation of Species Cross-reactive Aptamers Using Toggle SELEX," (2001) Molecular Therapy 4(6):567-573.
International Search Report and Written Opinion for PCT/US2006/036109 dated Sep. 5, 2007.
International Search Report and Written Opinion for PCT/US2008/004119 dated Jun. 26, 2008.
International Search Report and Written Opinion for PCT/US2007/022358 dated Aug. 18, 2008.
Office Action dated May 10, 2012 for U.S. Appl. No. 12/311,943.
Office Action dated Jun. 21, 2013 for U.S. Appl. No. 12/311,943.
Office Action dated Aug. 6, 2012 for U.S. Appl. No. 13/296,045.
Office Action dated Oct. 22, 2013 for U.S. Appl. No. 13/296,045.
Office Action dated Aug. 16, 2011 for U.S. Appl. No. 11/992,125.
Office Action dated Apr. 9, 2012 for U.S. Appl. No. 11/992,125.
Office Action dated Jul. 22, 2014 for U.S. Appl. No. 13/878,539.
Office Action dated Dec. 8, 2014 for U.S. Appl No. 13/878,539.
Office Action dated Sep. 17, 2015 for U.S. Appl. No. 14/115,797.

* cited by examiner

Amino acid sequence of lepirudin

Amino acid sequence of bivalirudin

Structure of fondaparinux

PRT 54004 betrixaban

Molecular structure of argatroban

Molecular structure of EP217609

Structure of a pentasaccharide anticoagulant moiety of EP217609.
R5 on C3 is OMe and R5 on C6 is OSO3⁻

EP217609's DTI residue

Molecular structure of biotin

Mechanical components of a TEG analyzer

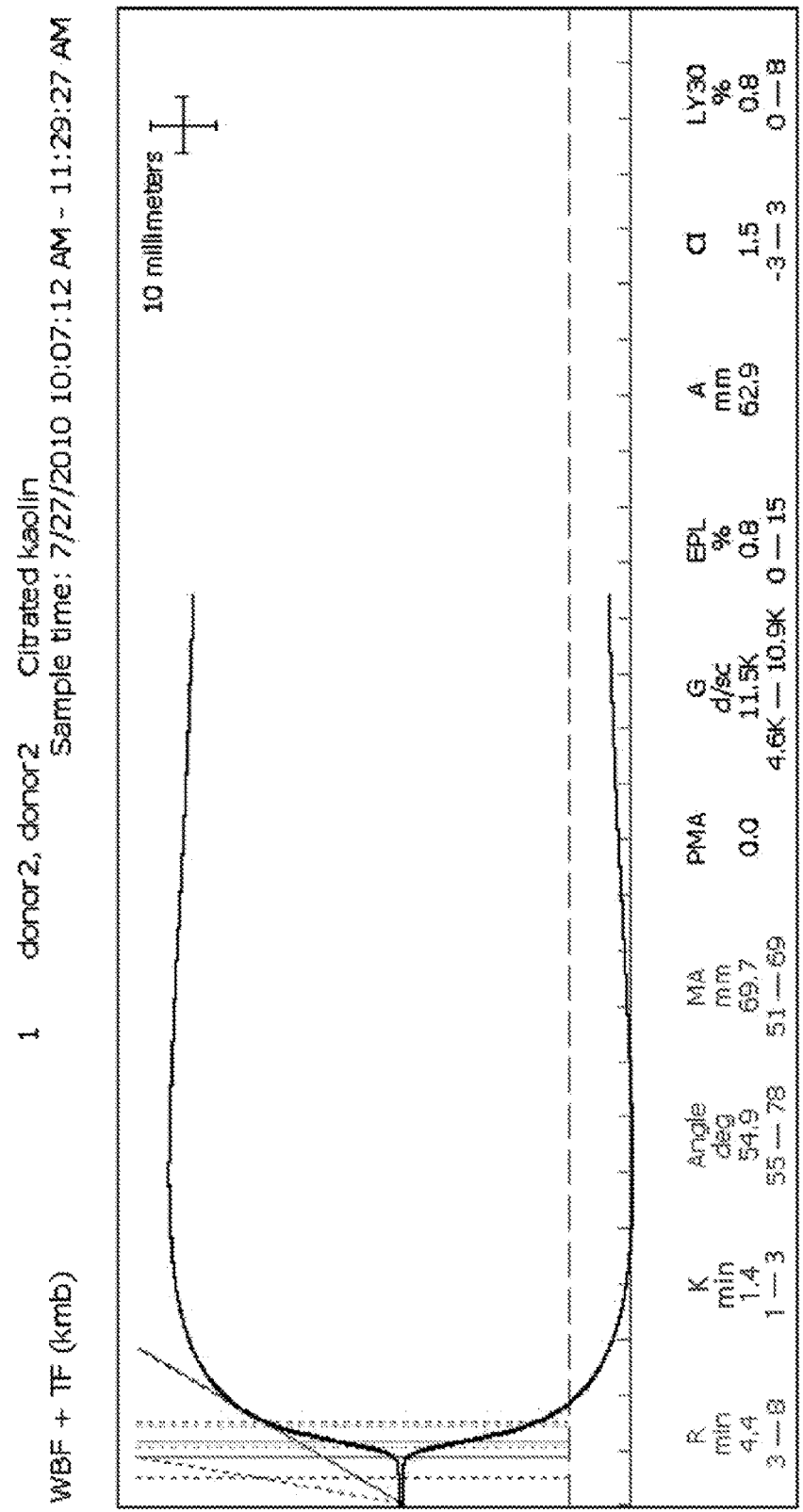
FIG. 14A. BUFFER

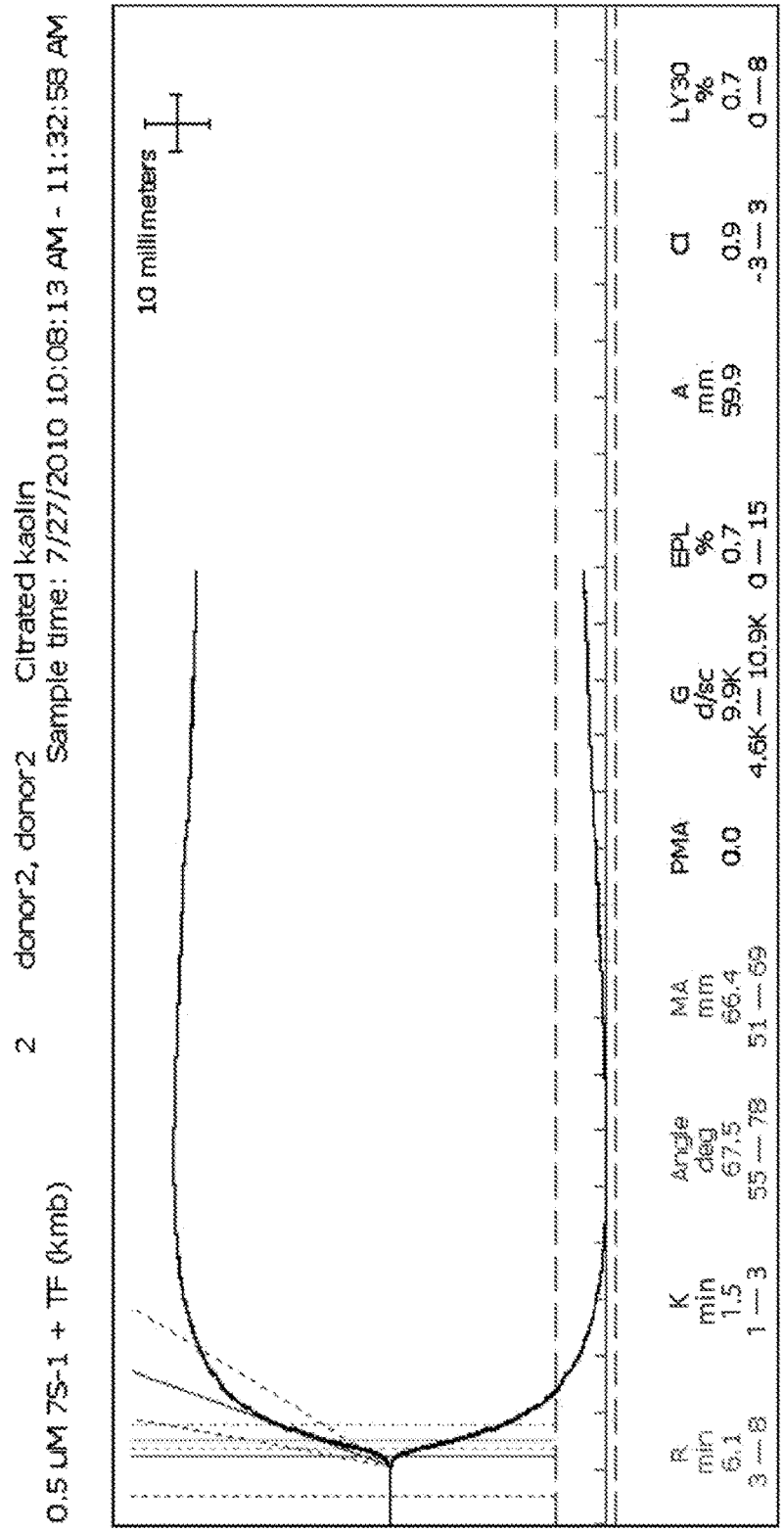
FIG. 14B. FVIIa APTAMER, 0.5 MICROMOLAR

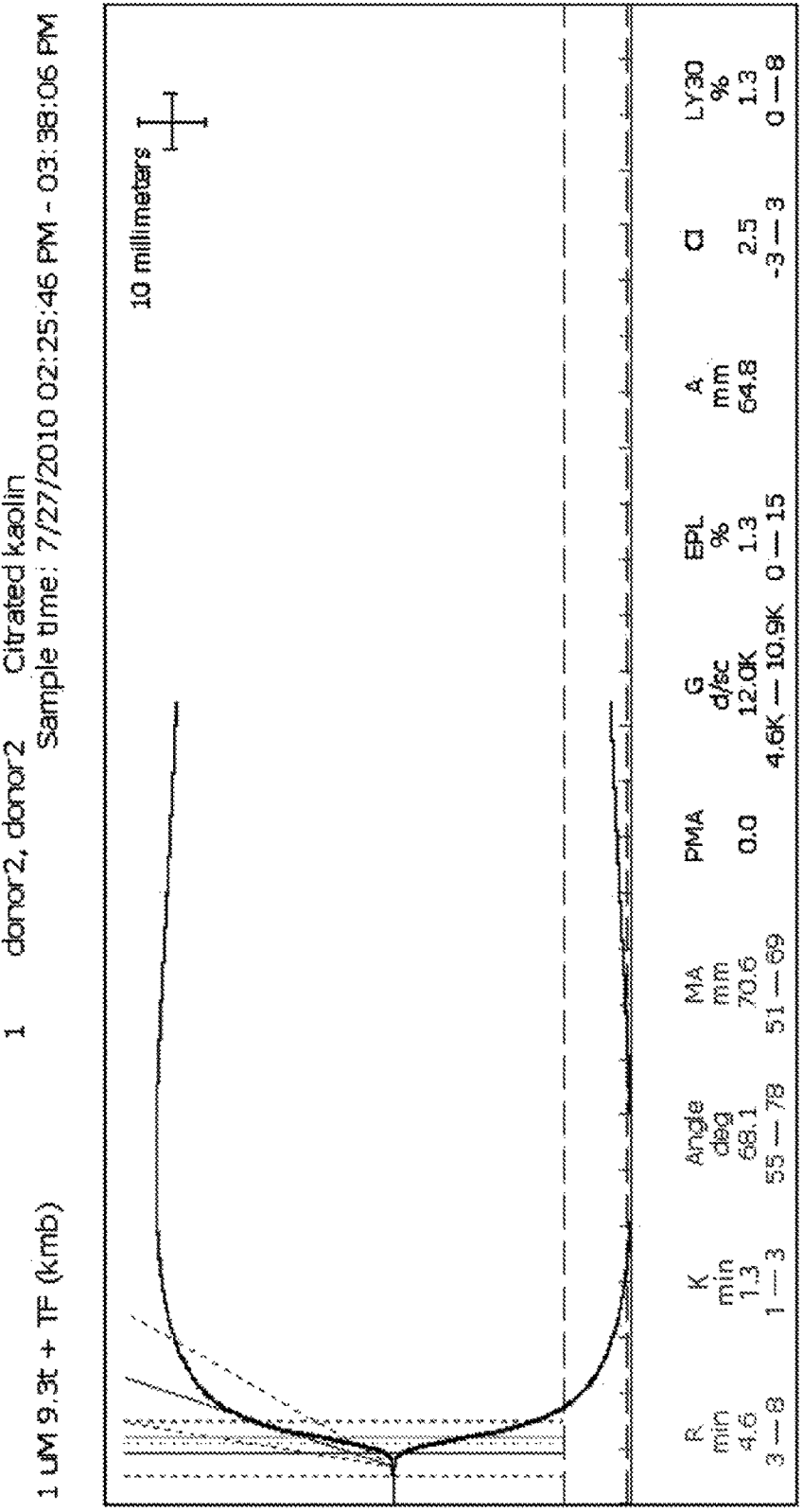
FIG. 14C. FIXa APTAMER, 1.0 MICROMOLAR

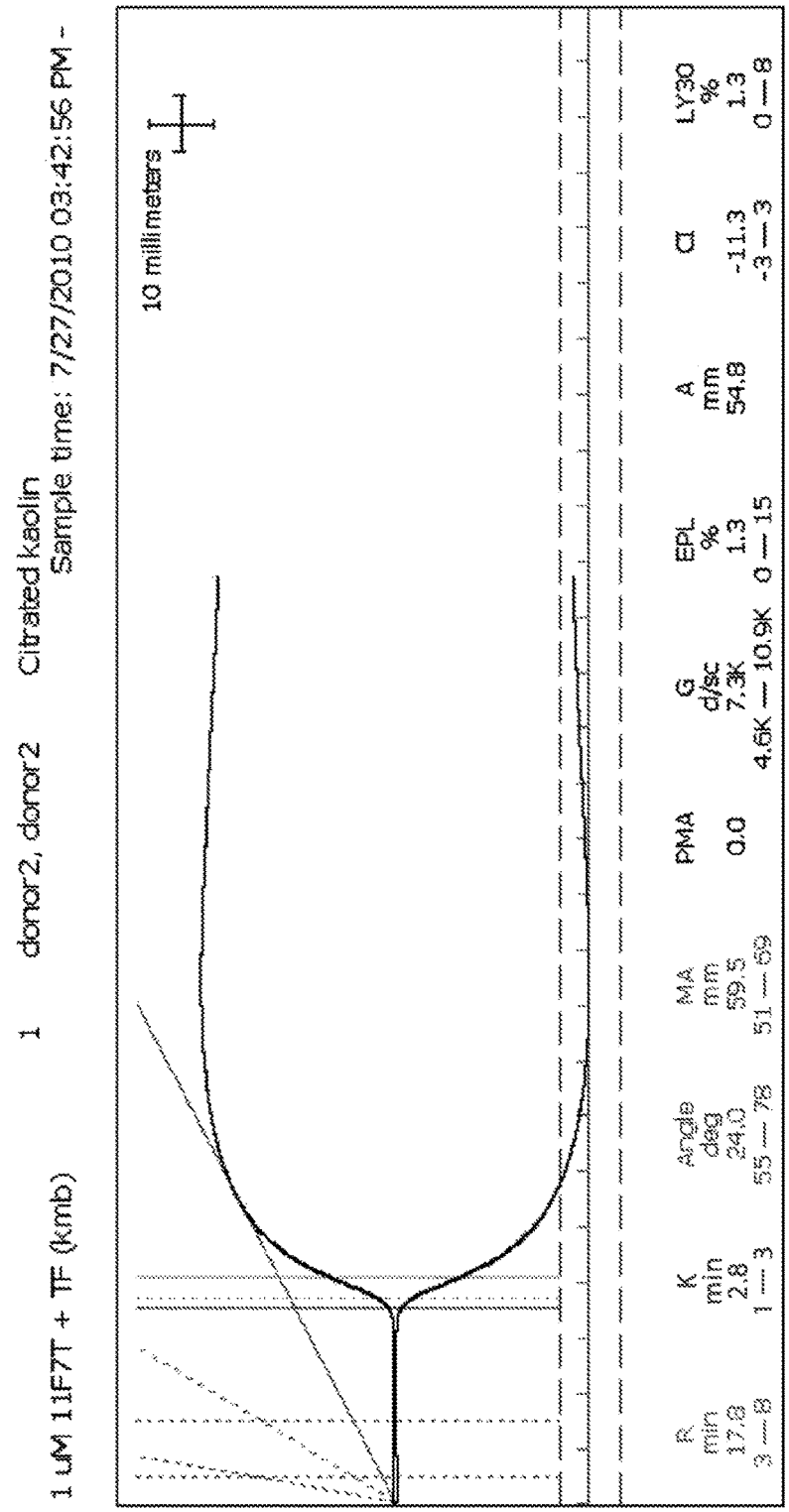
FIG. 14D. FXa APTAMER, 1.0 MICROMOLAR

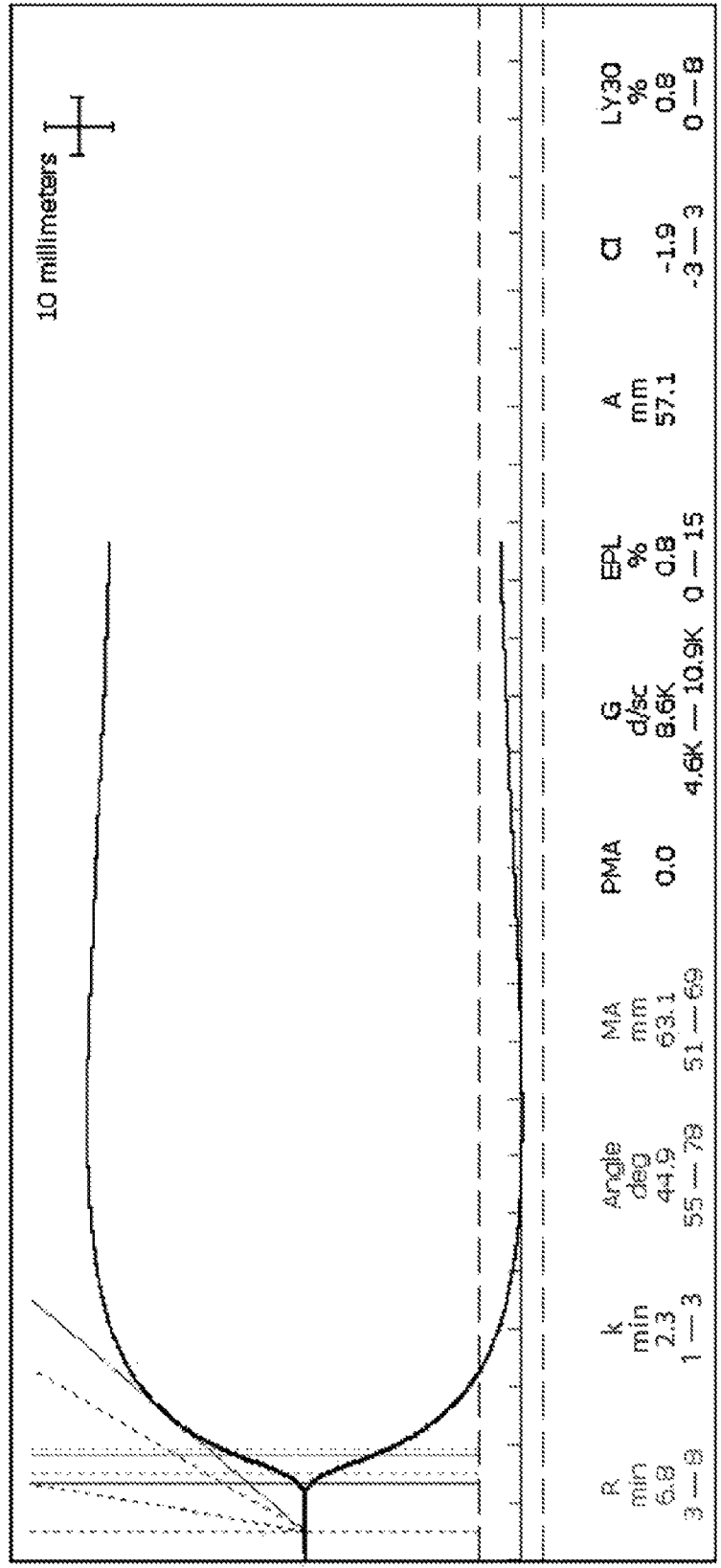
FIG. 15A. BUFFER

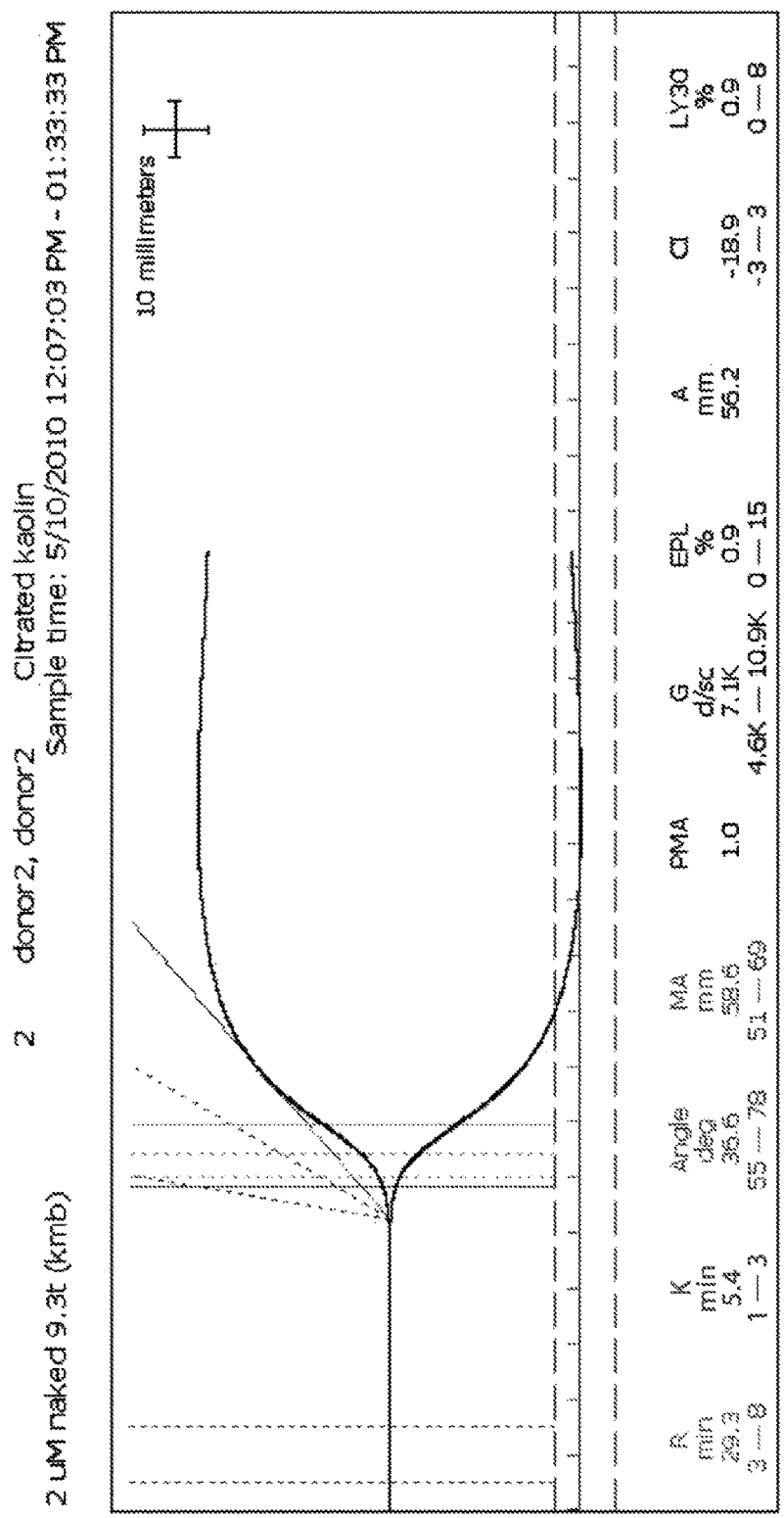
FIG. 15B. FIXa APTAMER, 2.0 MICROMOLAR

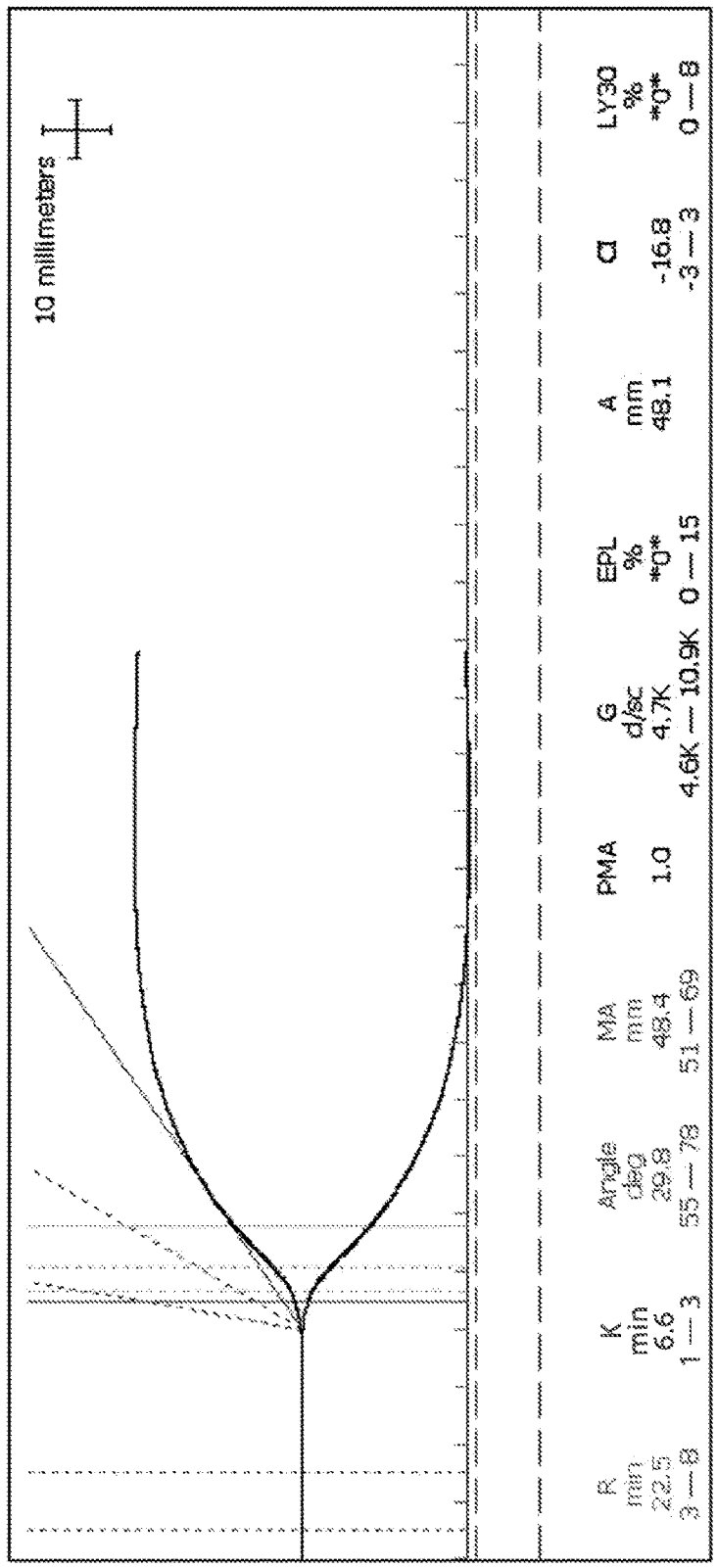
FIG. 15C. FXa APTAMER, 2.0 MICROMOLAR

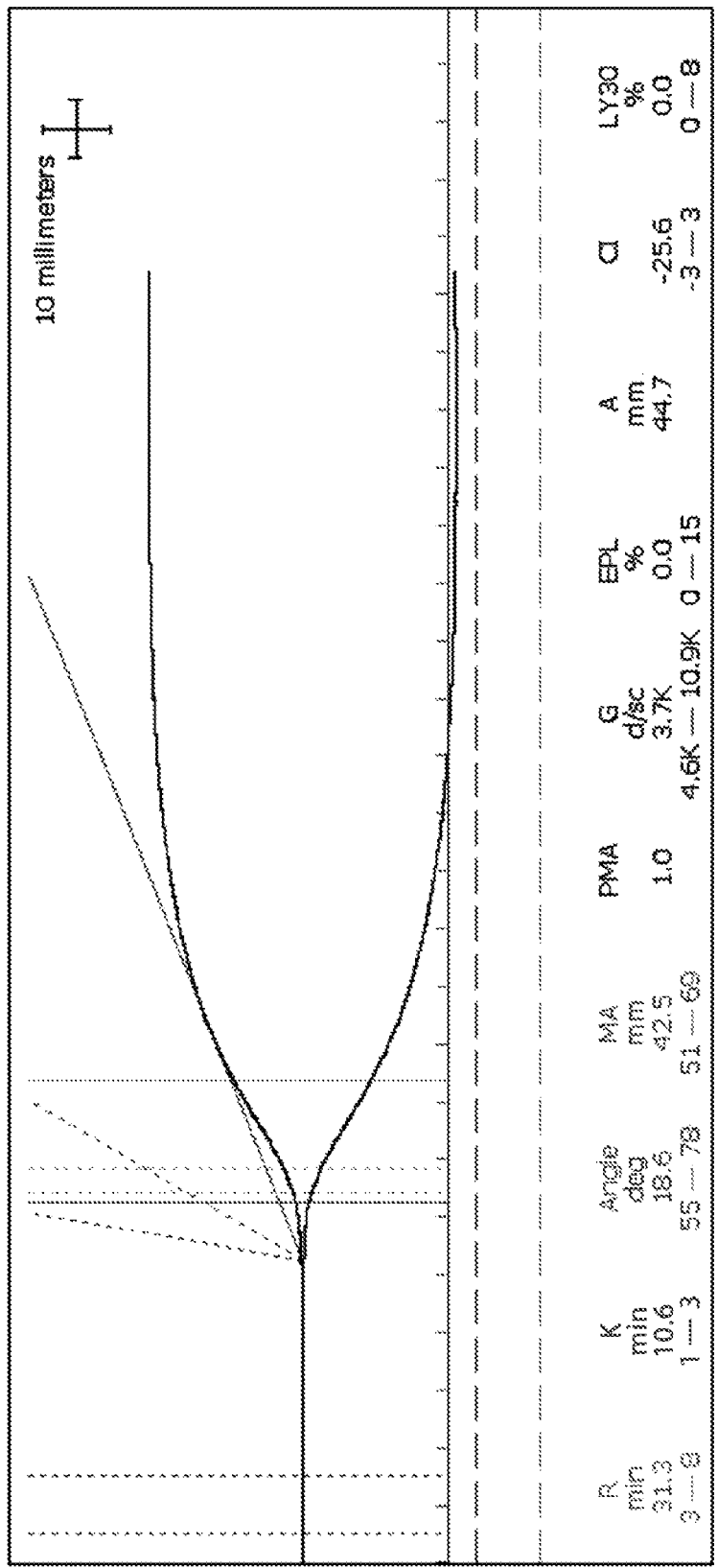
FIG. 15D. THROMBIN APTAMER, 5.0 MICROMOLAR

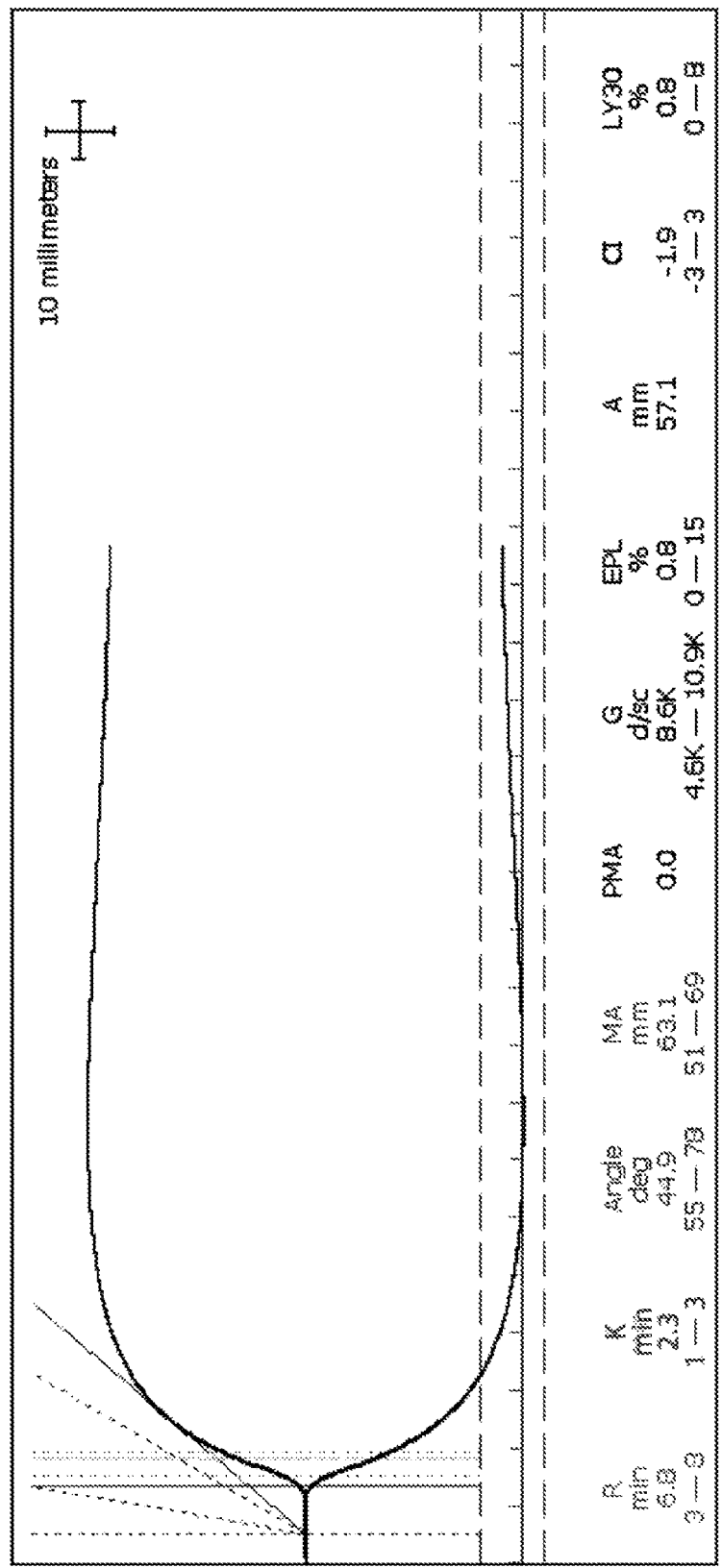
FIG. 16A. BUFFER

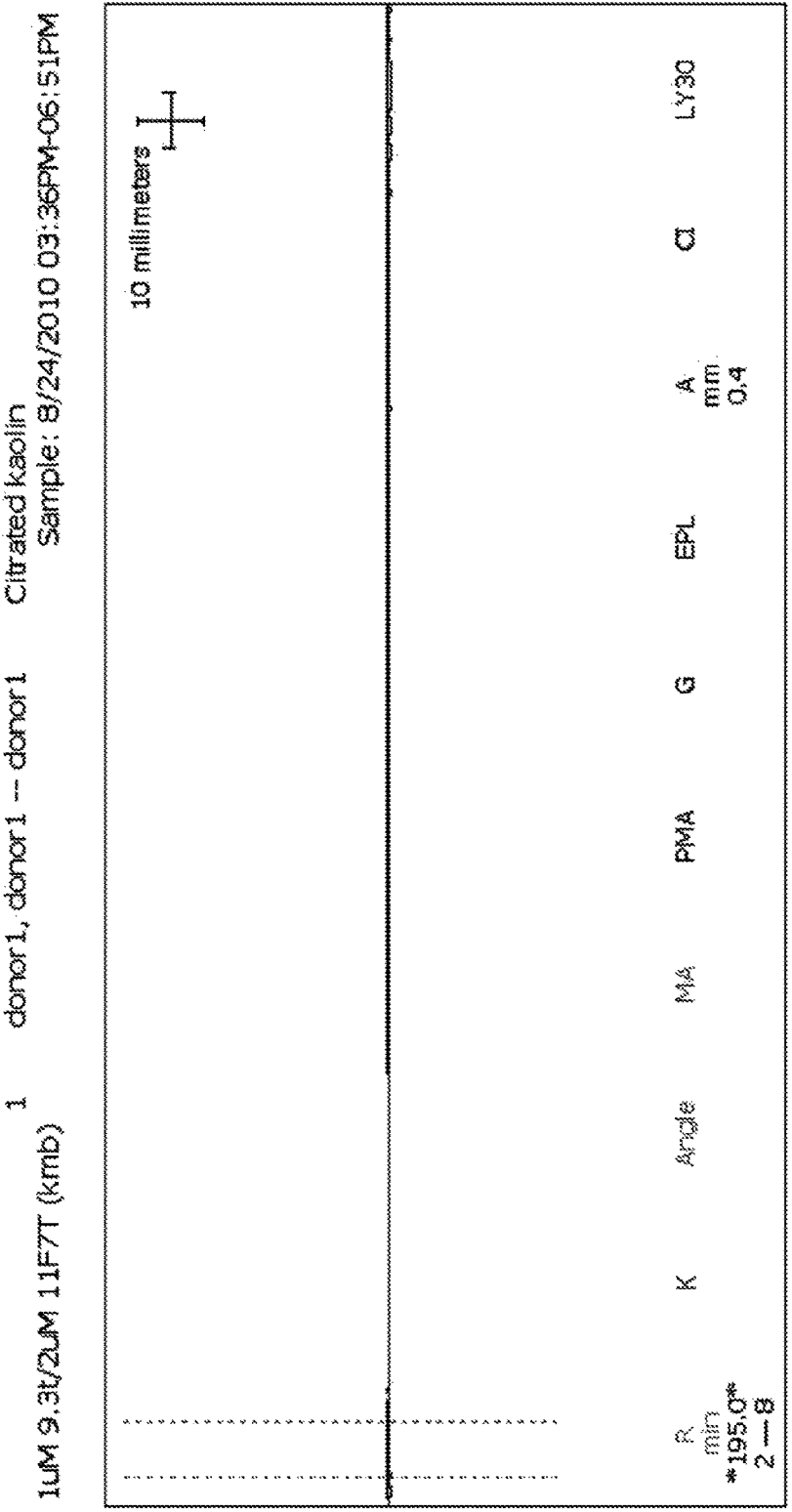
FIG. 16B. FIXa APTAMER, 1.0 MICROMOLAR + FXa APTAMER, 2.0 MICROMOLAR

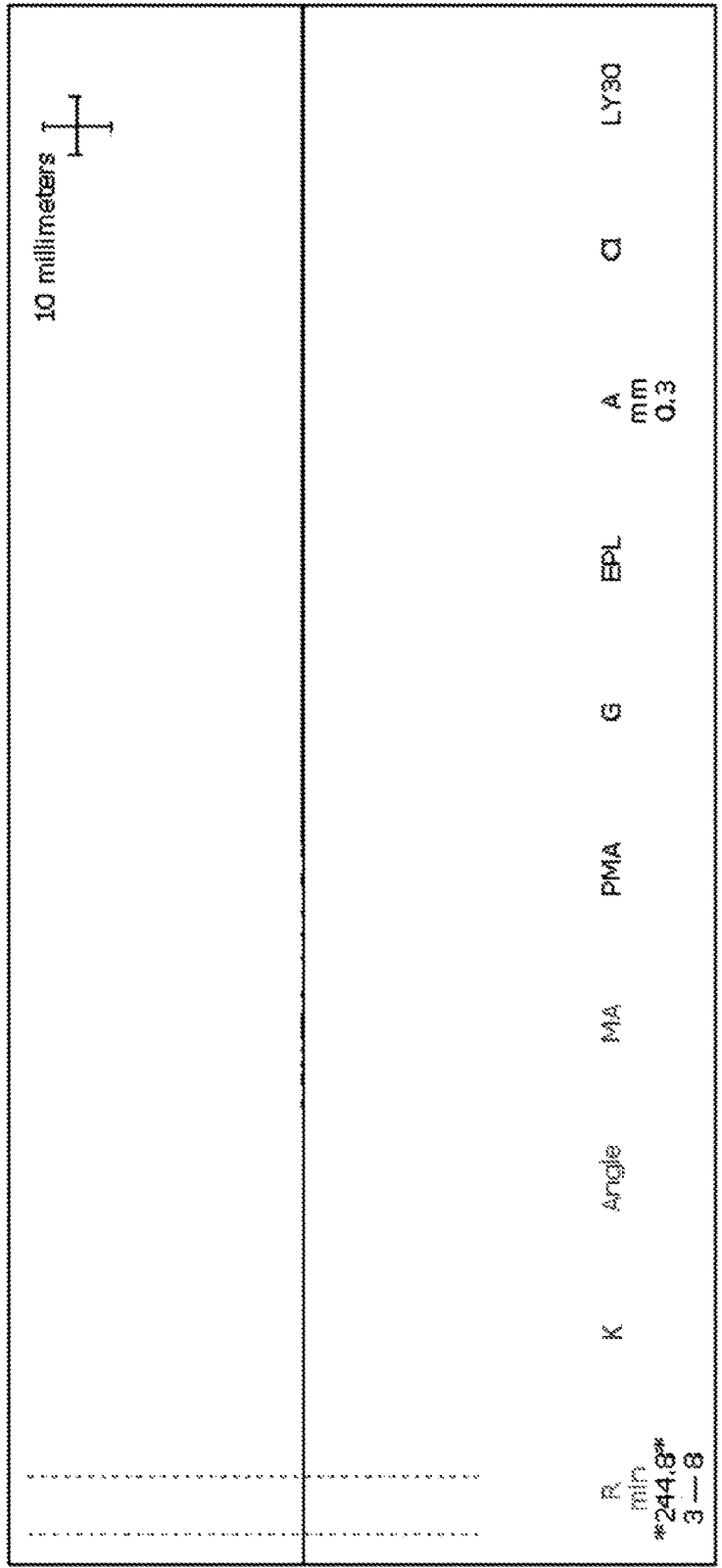
FIG. 16C. FIXa APTAMER, 1.0 MICROMOLAR + THROMBIN APTAMER, 5.0 MICROMOLAR

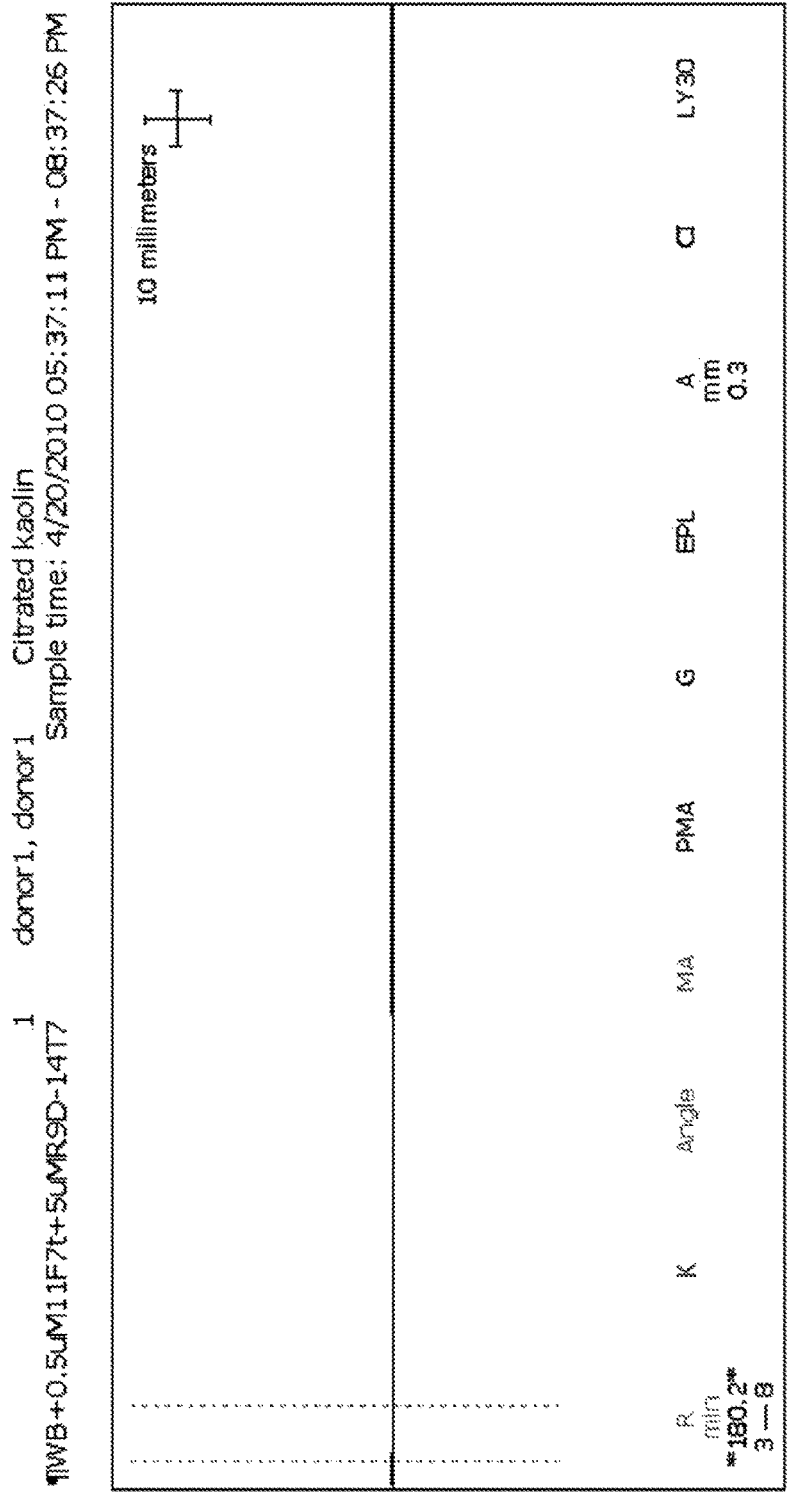
FIG. 16D. FXa APTAMER, 0.5 MICROMOLAR + THROMBIN APTAMER, 5.0 MICROMOLAR

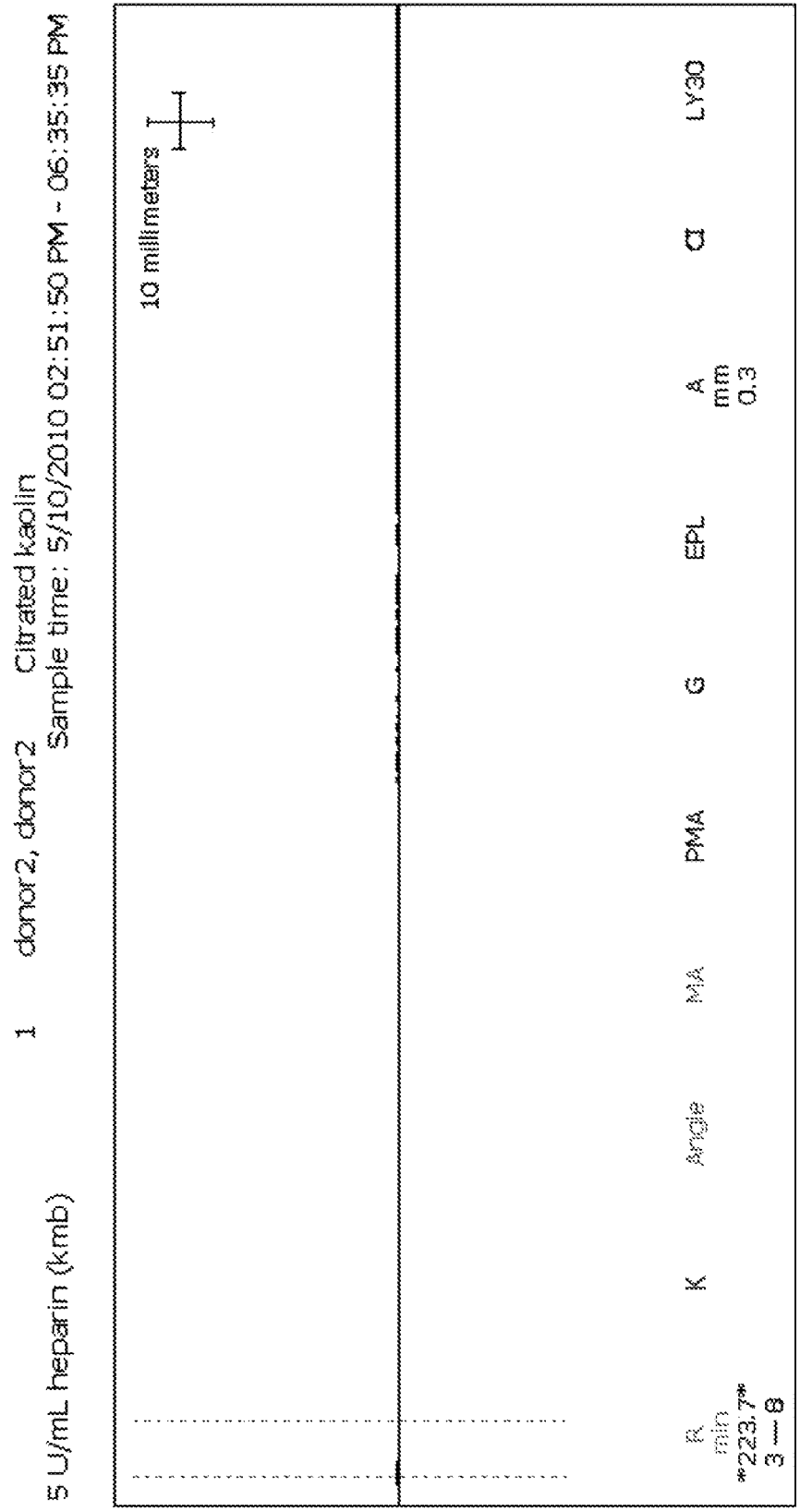
FIG. 16E. UFH, 5 U/mL

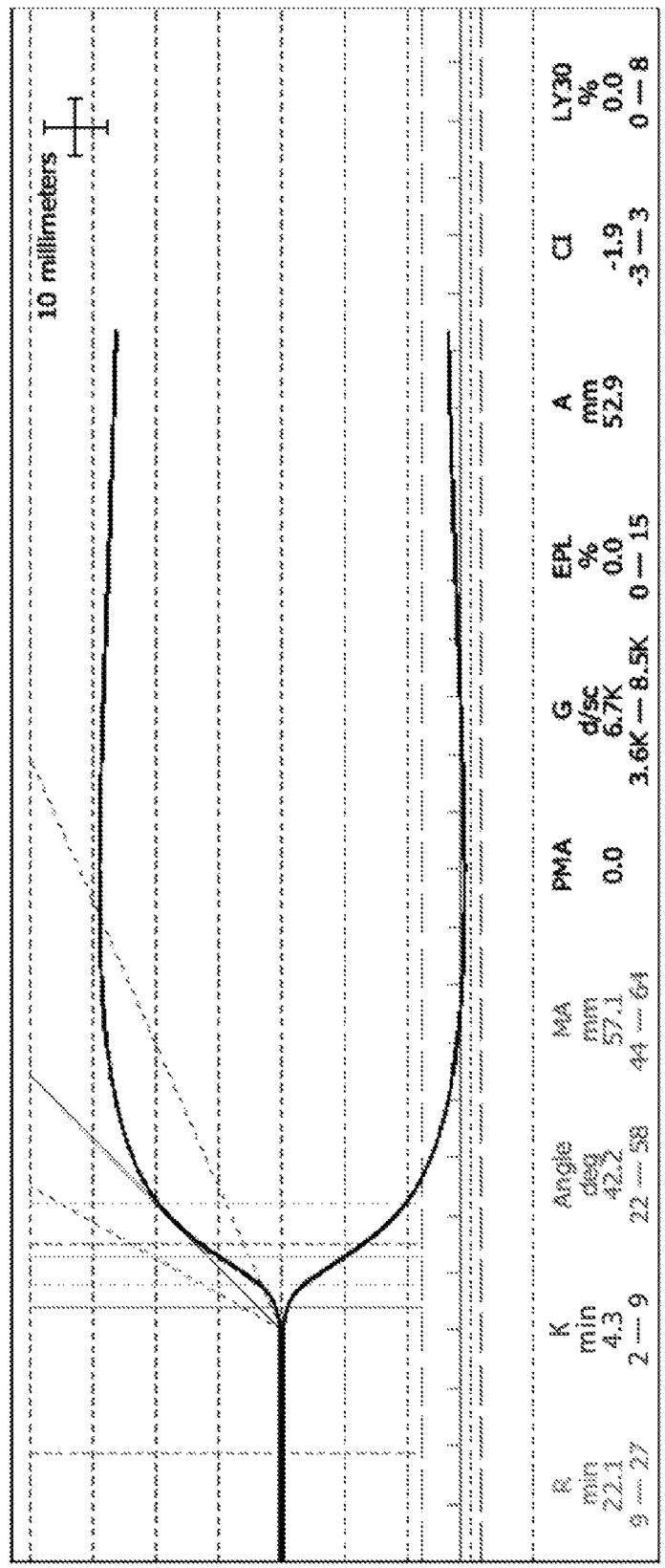
FIG. 17A. FIXa APTAMER, 0.5 MICROMOLAR

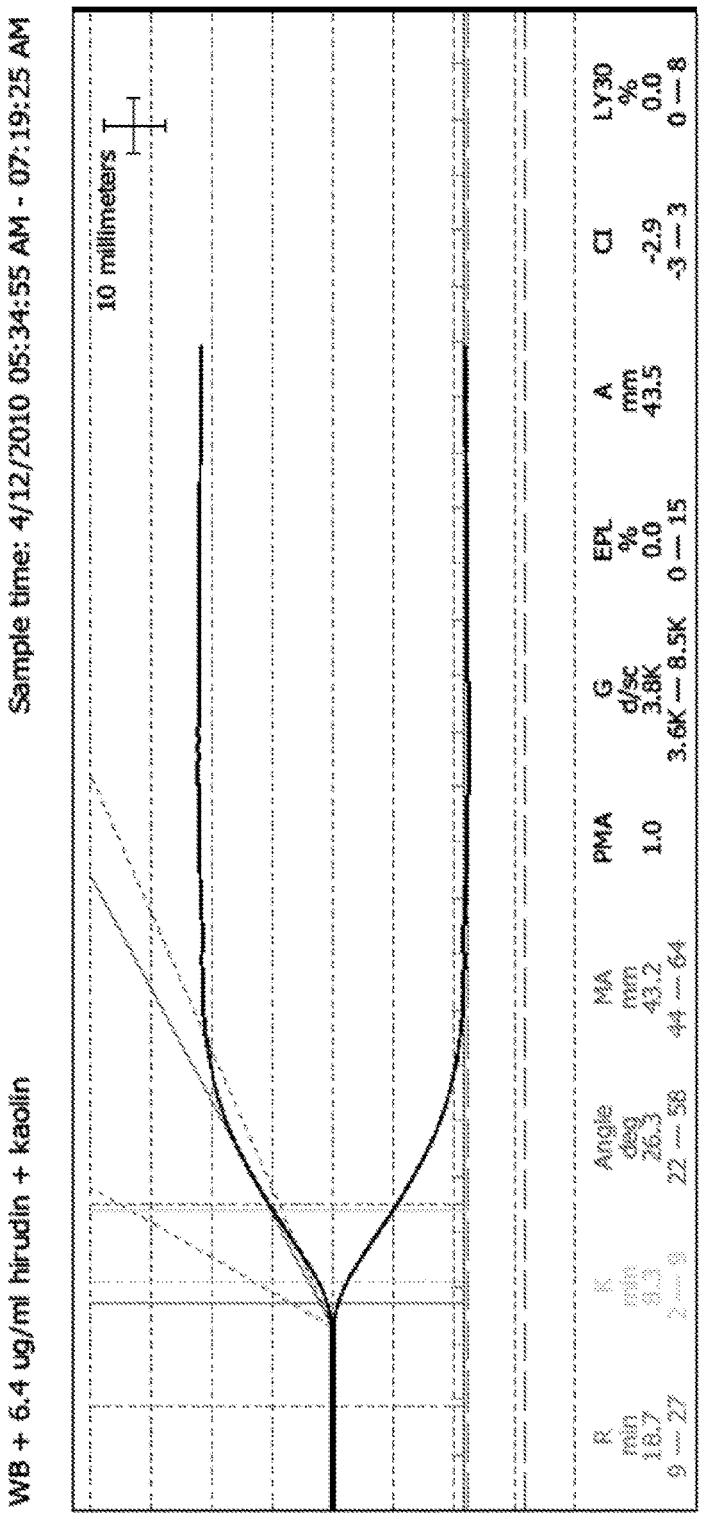
FIG. 17 B. LEPIRUDIN, 6.4 MICROGRAMS/ML (0.860 MICROMOLAR)

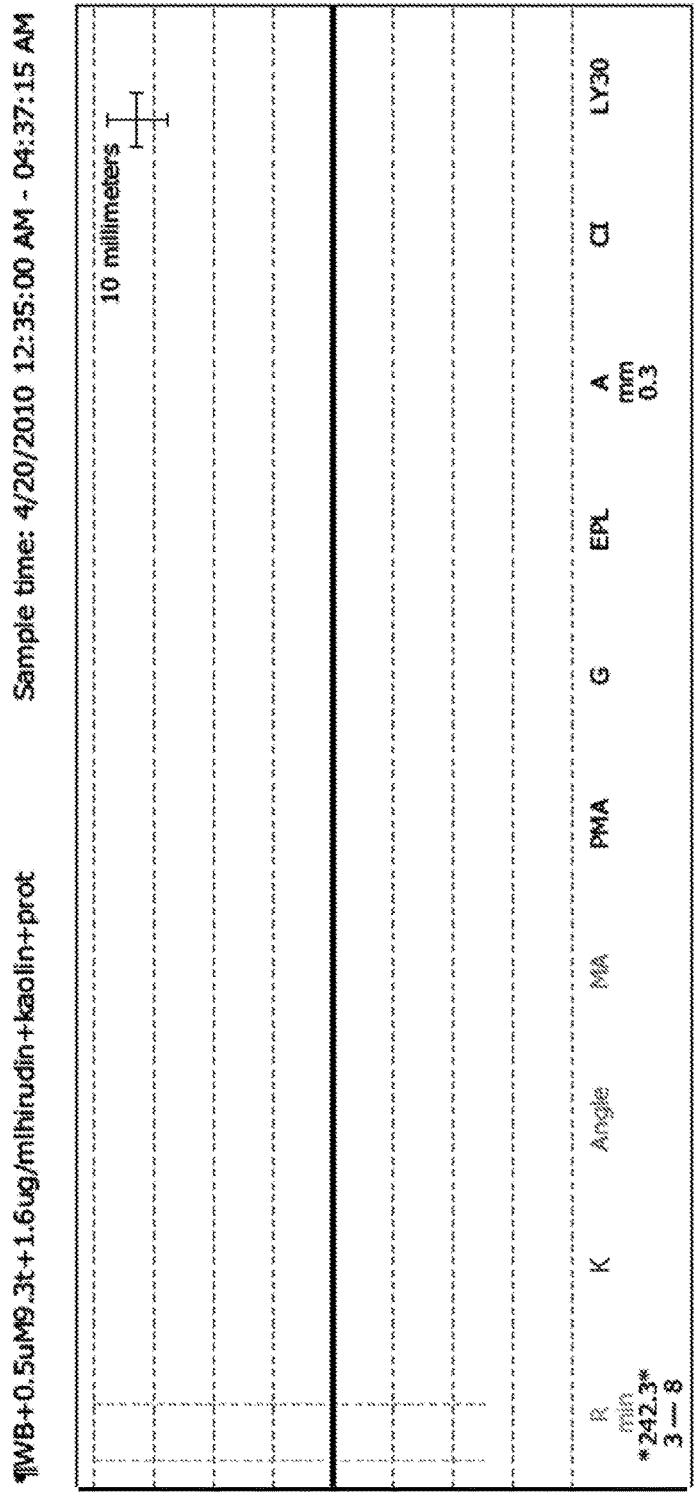
FIG. 17C. FIXa APTAMER, 0.5 MICROMOLAR + LEPIRUDIN, 1.6 MICROGRAMS/ML (0.215 MICROMOLAR)

Isolated oxygenator circuit

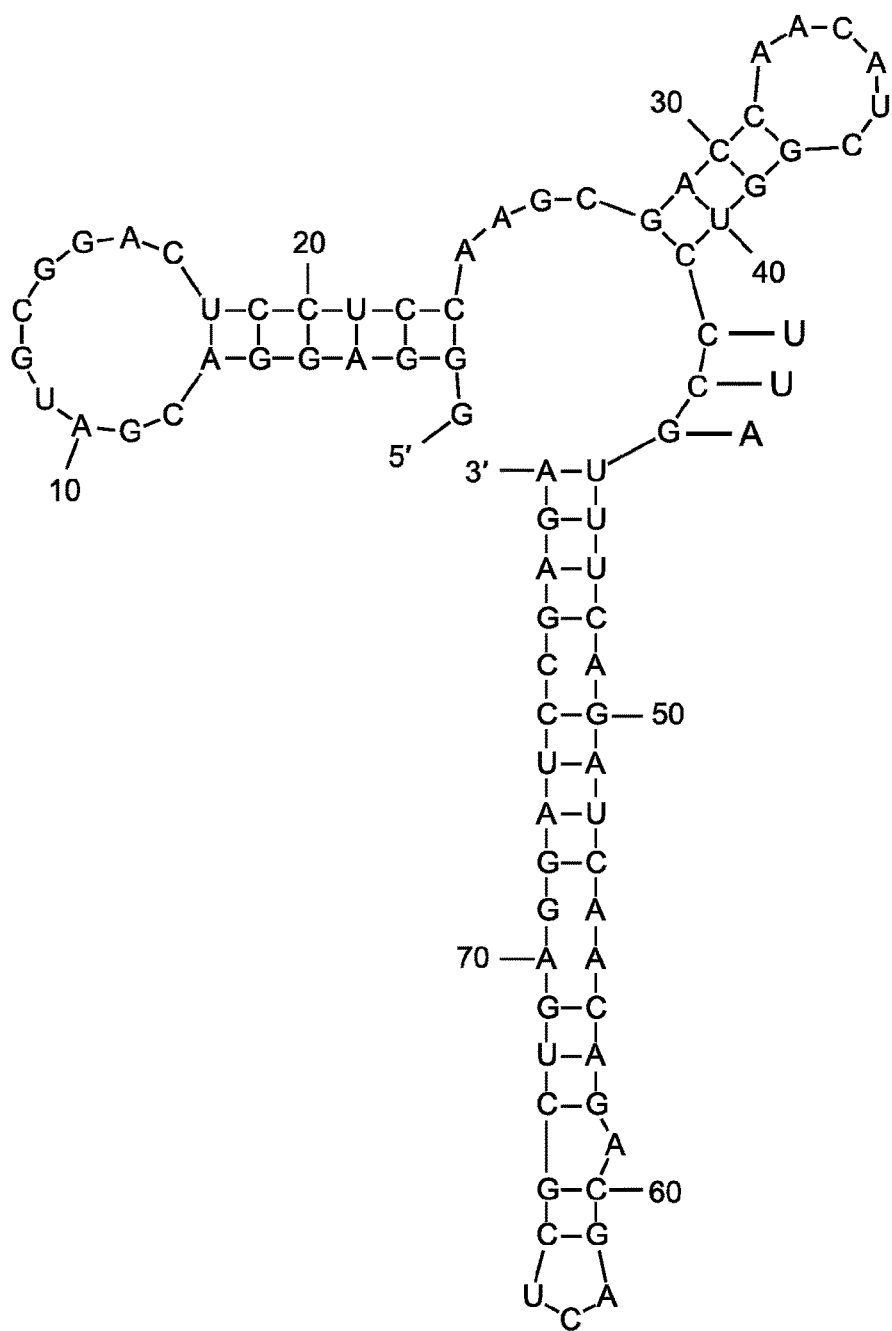
FIG. 19. The M-fold predicted secondary structures of the four modified RNA anticoagulant aptamers and their point mutants.

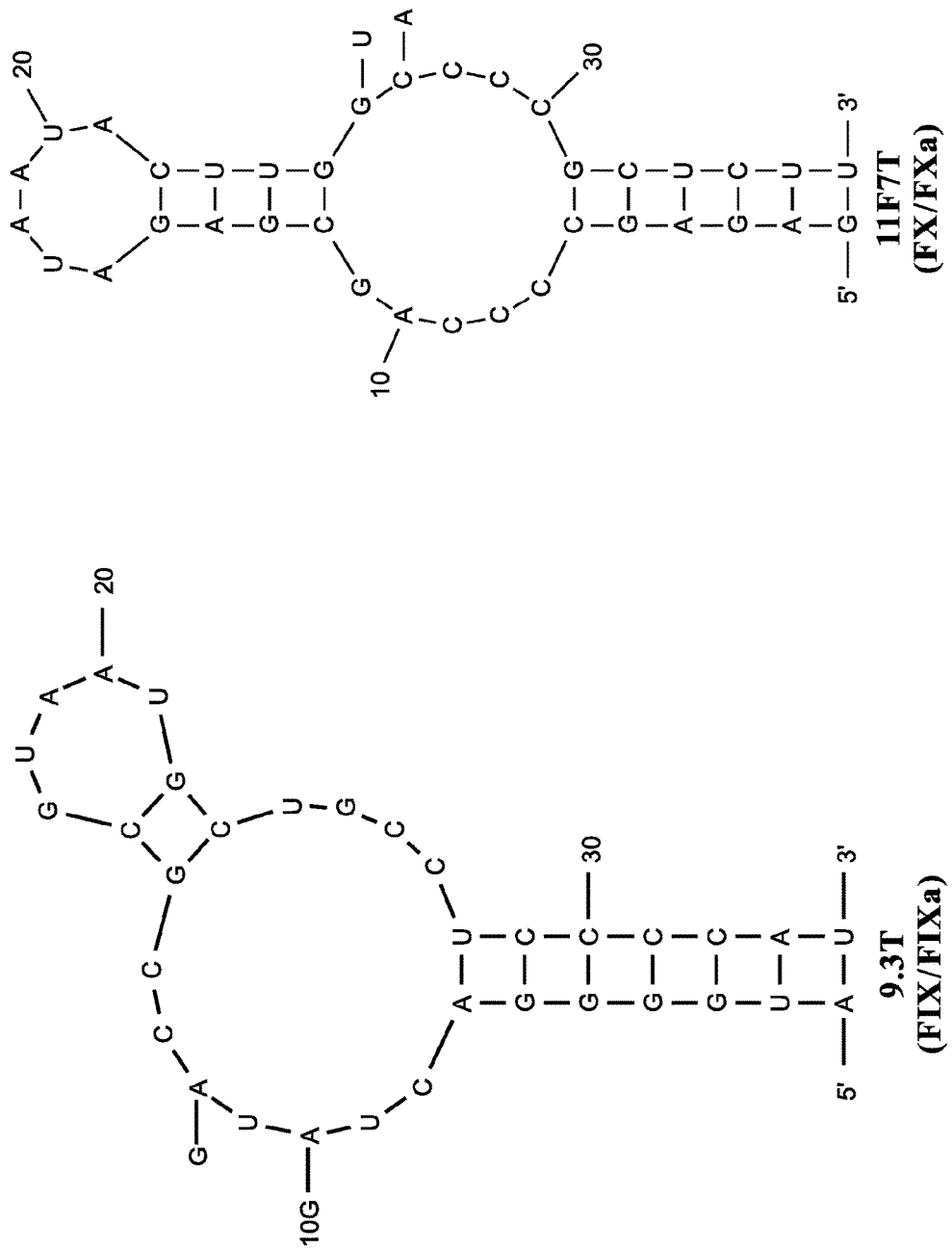
FIG. 19 cont'd-1. The M-fold predicted secondary structures of the four modified RNA anticoagulant aptamers and their point mutants.

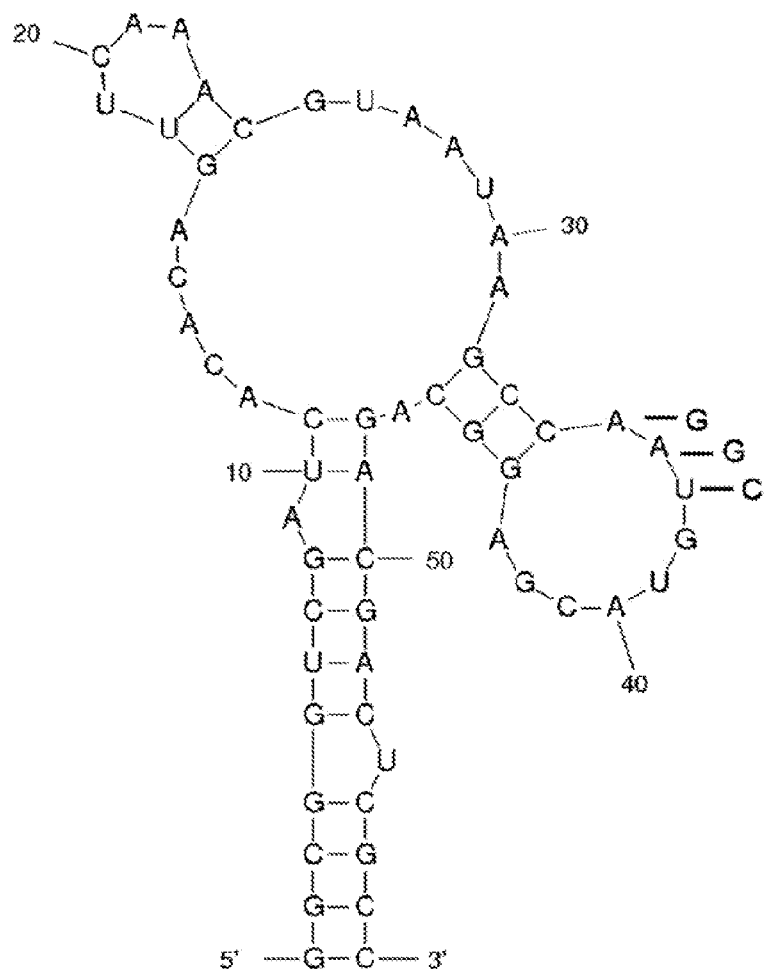
R9D-14T
(prothrombin/thrombin)
FIG. 19 cont'd-2. The M-fold predicted secondary structures of the four modified RNA anticoagulant aptamers and their point mutants.

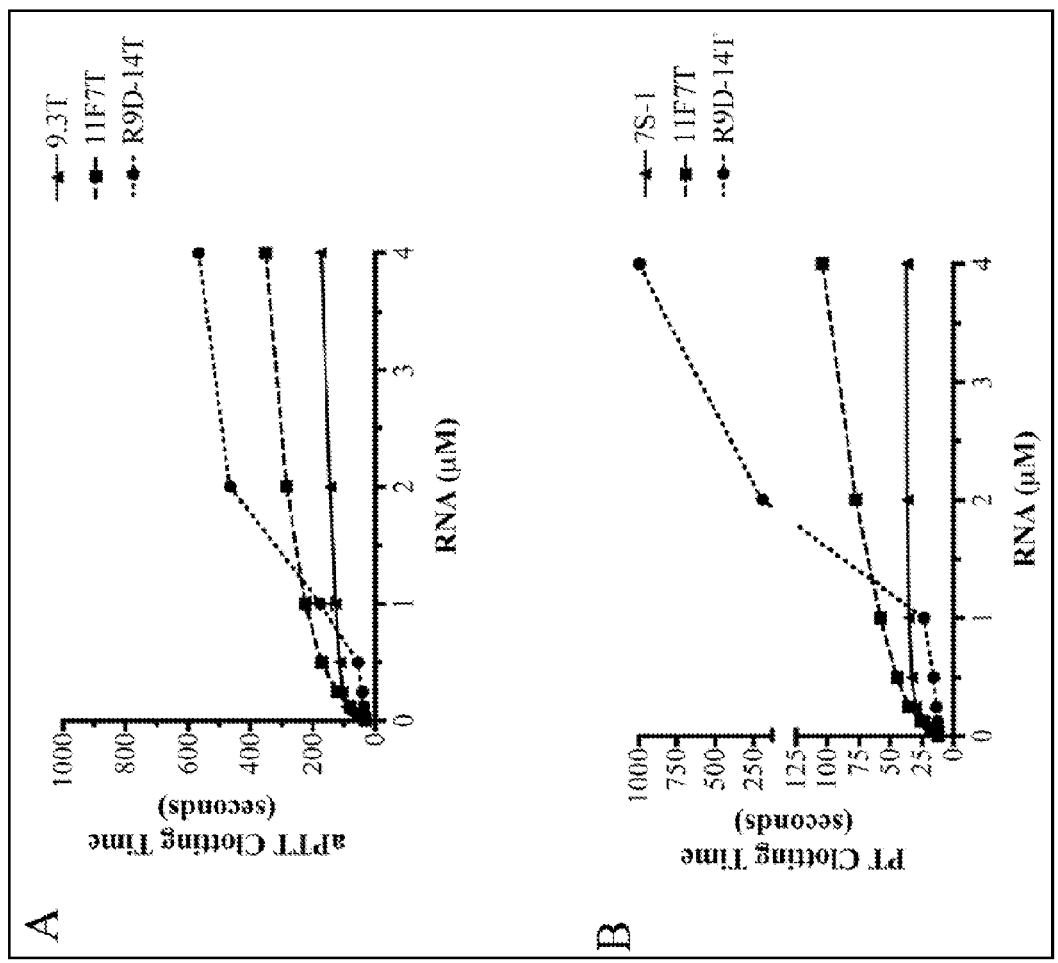

FIG. 20. Dose titrations with each of the four anticoagulant aptamers in clinical aPTT and PT plasma clotting assays. A) Dose titration response with individual aptamers in the activated partial thromboplastin time (aPTT) assay. B) Dose titration response with the individual aptamers in the prothrombin time (PT) assay. The data represent the mean ± SEM of duplicates; the lines were arbitrarily drawn. 7S-1: FVIIa aptamer; 9.3T: FIXa aptamer; 11F7T: FXa aptamer; and R9D-14T: prothrombin aptamer.

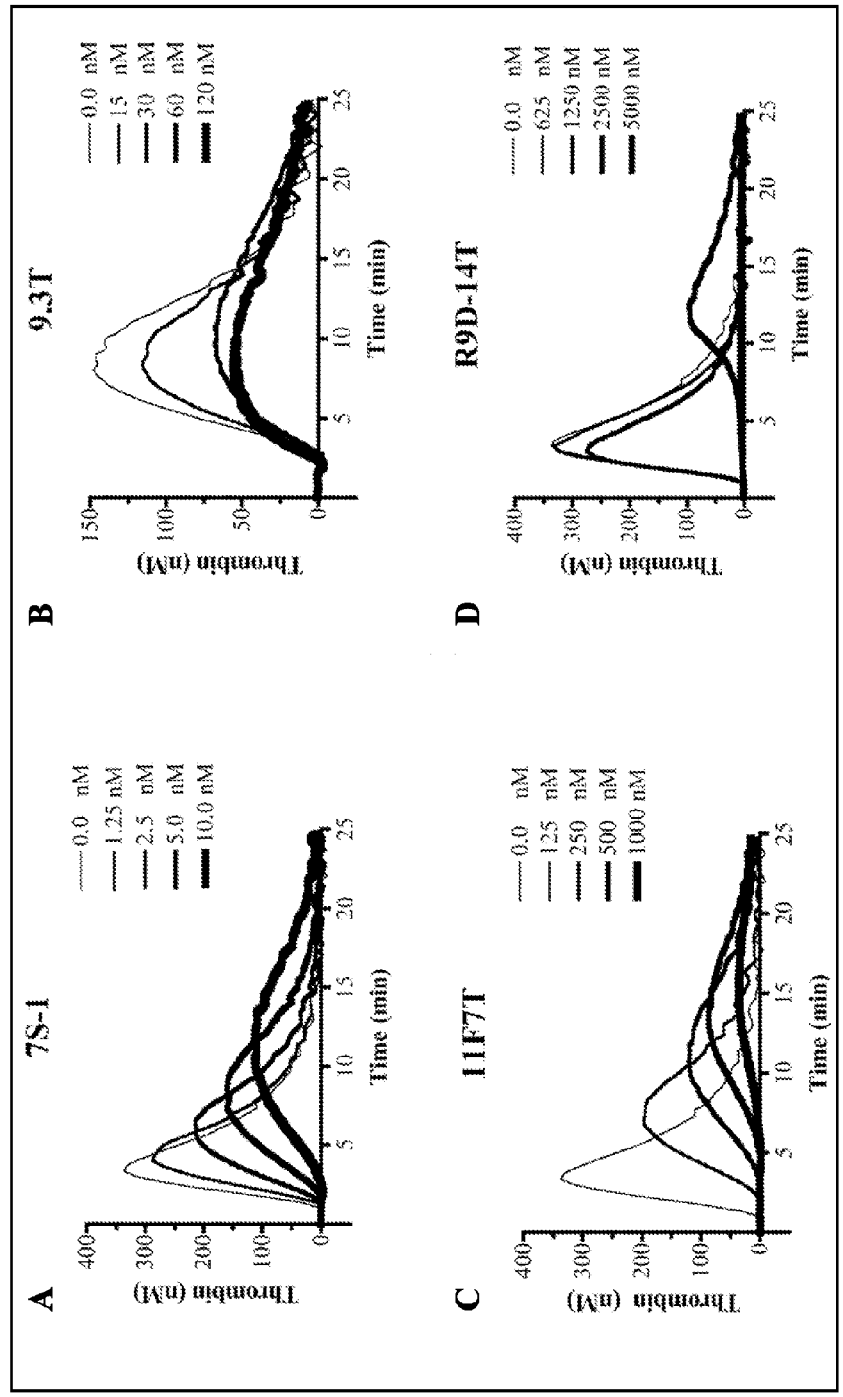

FIG. 21. Dose titrations with each of the four anticoagulant aptamers in calibrated automated thrombography. Thrombograms with various concentrations of A) 7S-1 with 5 pM TF; B) 9.3T with 1 pM TF; C) 11F7T with 5 pM TF; and D) R9D-14T with 5 pM TF. For 5,000 nM R9D-14T there was no thrombin generation detected. Platelet poor plasma (80 µL) was incubated with aptamer (10 µL) at 37°C for 5 min, TF was added (20 µL) and incubated at 37°C for another 5 min. The assay was initiated with the addition of FluCa substrate (10 µL) and thrombin generation was measured at 37°C for 1 hour. The data represent the mean of duplicates. 7S-1: Factor VIIa aptamer; 9.3T: Factor IXa aptamer; 11F7T: Factor Xa aptamer; and R9D-14T: prothrombin aptamer.

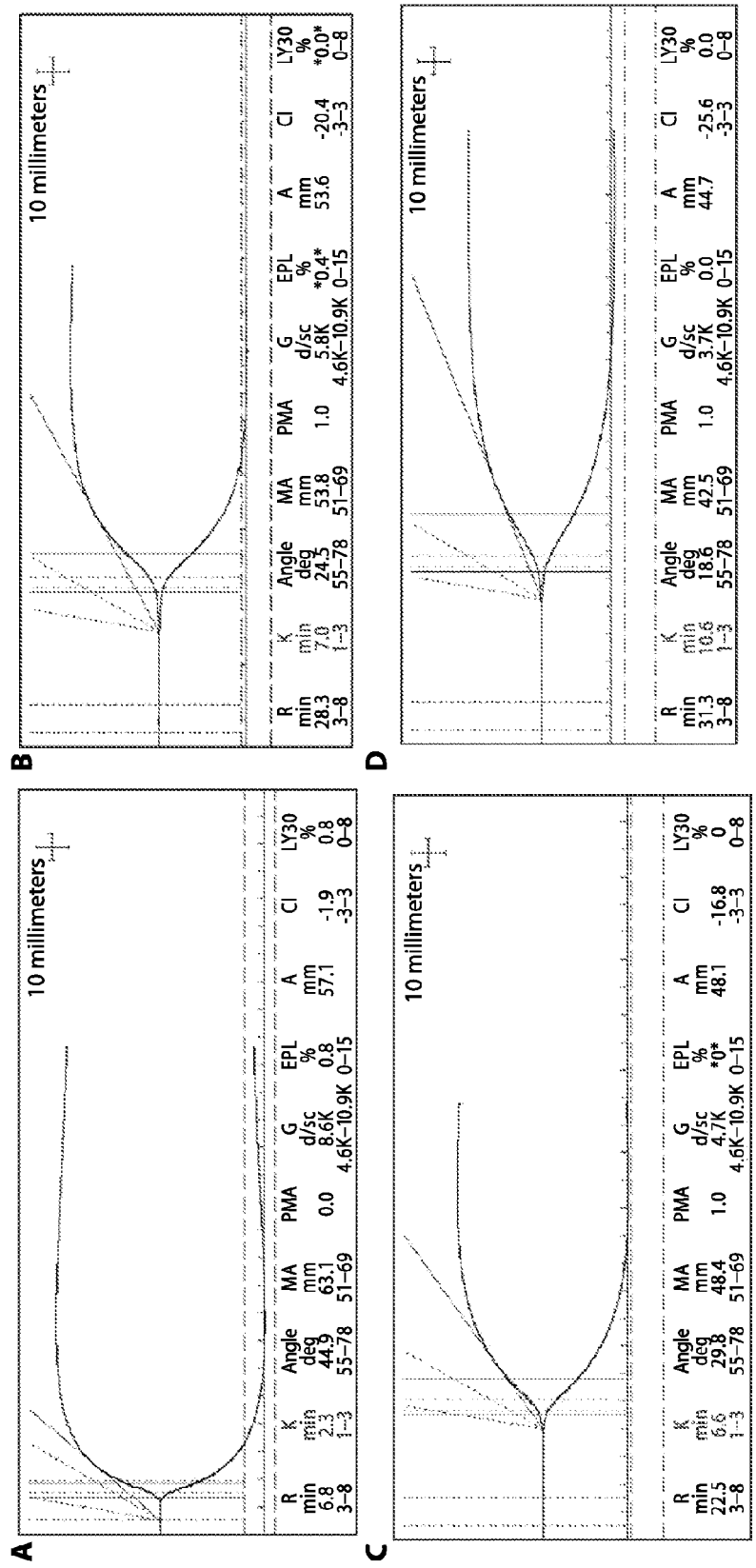

FIG. 22. Thromboelastography tracings for saturating concentrations of each of the four anticoagulant aptamers with either kaolin or tissue factor activation. Thromboelastography tracings for blood anticoagulated and activated with A) buffer control with kaolin, B) 9.3T (1 μM) and kaolin, C) 11F7T (2 μM) and kaolin, D) R9D-14T (5 μM) and kaolin, E) buffer with TF, F) 7S-1 (0.5 μM) and TF, G) 9.3T (1 μM) and TF, H) 11F7T (2 μM) and TF, and I) R9D-14T (5 μM) and TF. Blood was drawn from a healthy volunteer and citrated. Citrated blood (320 μL) was mixed with aptamer (10 μL) and either kaolin or TF (10 μL), and the assay was initiated by the addition of calcium chloride (20 μL). The data are representative of data for 3 different donors. 7S-1: Factor VIIa aptamer; 9.3T: Factor IXa aptamer; 11F7T: Factor Xa aptamer; and R9D-14T: prothrombin aptamer.

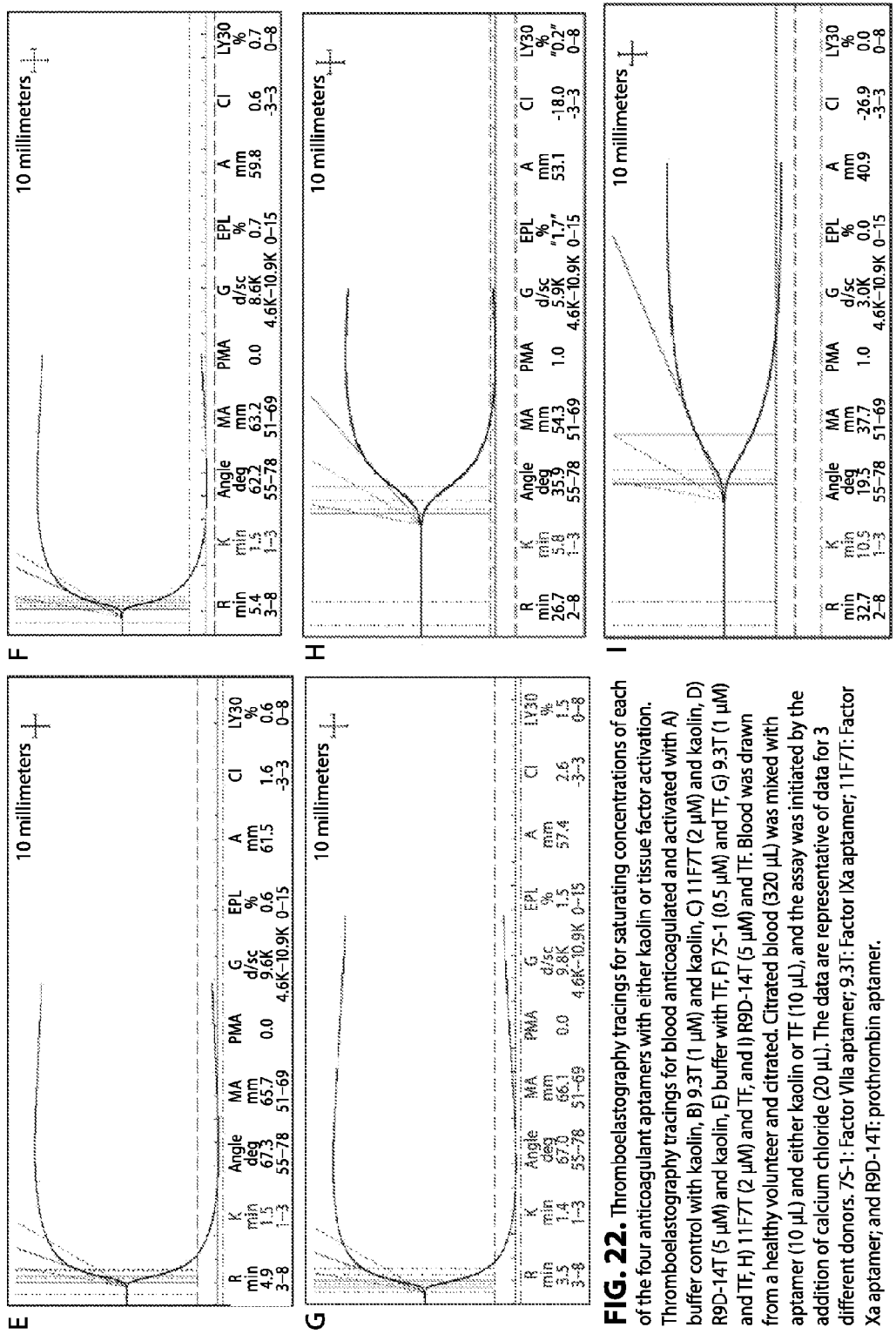

FIG. 22. Thromboelastography tracings for saturating concentrations of each of the four anticoagulant aptamers with either kaolin or tissue factor activation. Thromboelastography tracings for blood anticoagulated and activated with A) buffer control with kaolin, B) 9.3T (1 µM) and kaolin, C) 11F7T (2 µM) and kaolin, D) R9D-14T (5 µM) and kaolin, E) buffer with TF, F) 7S-1 (0.5 µM) and TF, G) 9.3T (1 µM) and TF, H) 11F7T (2 µM) and TF, and I) R9D-14T (5 µM) and TF. Blood was drawn from a healthy volunteer and citrated. Citrated blood (320 µL) was mixed with aptamer (10 µL) and either kaolin or TF (10 µL), and the assay was initiated by the addition of calcium chloride (20 µL). The data are representative of data for 3 different donors. 7S-1: Factor VIIa aptamer; 9.3T: Factor IXa aptamer; 11F7T: Factor Xa aptamer; and R9D-14T: prothrombin aptamer.

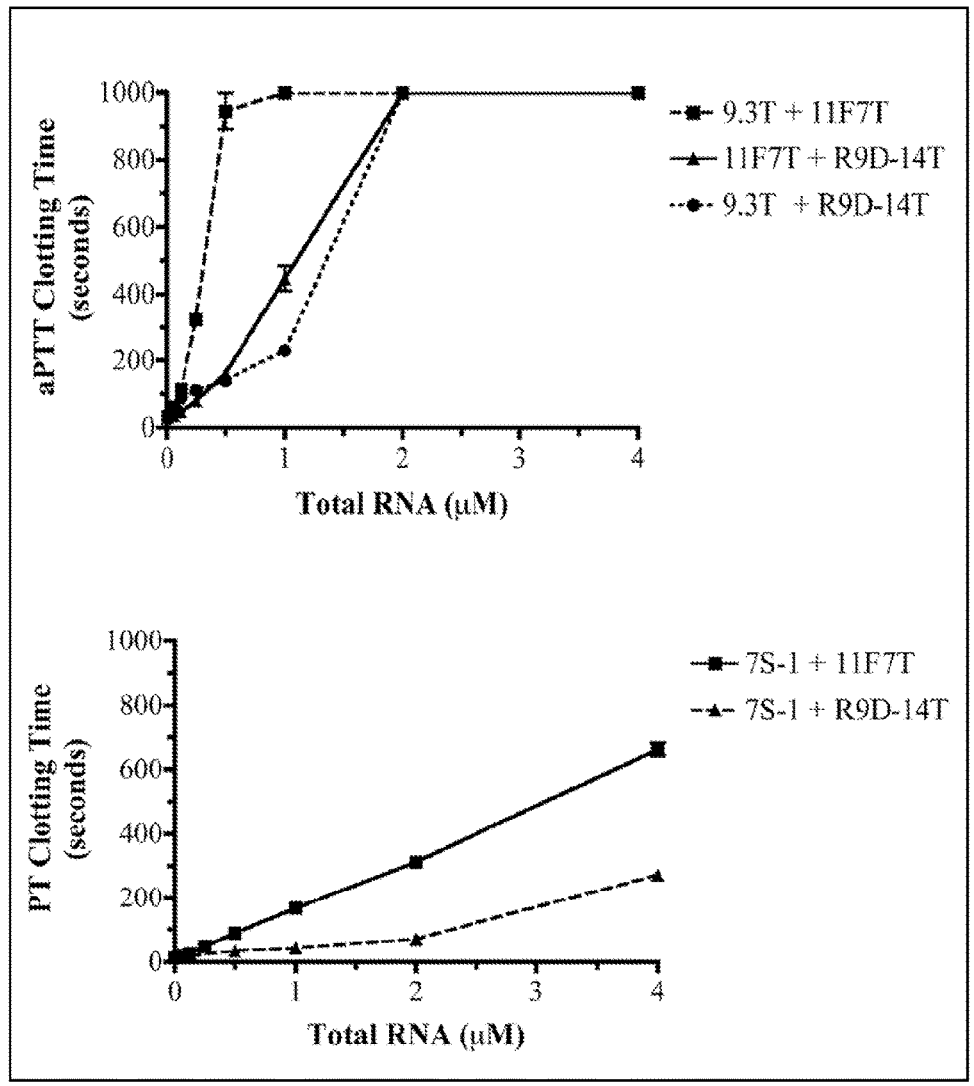

FIG. 23. Combinations of two anticoagulant aptamers in the clinical aPTT and PT plasma clotting assays. A) Dose titration for combinations of two aptamers in the aPTT assay. The x-axis represents the total RNA concentration, where each aptamer is present at an equimolar concentration. B) Dose titration for combinations of two aptamers in the PT assay. The x-axis represents the total RNA concentration, where each aptamer is present in an equimolar concentration. The data represent the mean ± SEM of duplicates; the lines were arbitrarily drawn. 7S-1: Factor VIIa aptamer; 9.3T: Factor IXa aptamer; 11F7T: Factor Xa aptamer; and R9D-14T: prothrombin aptamer.

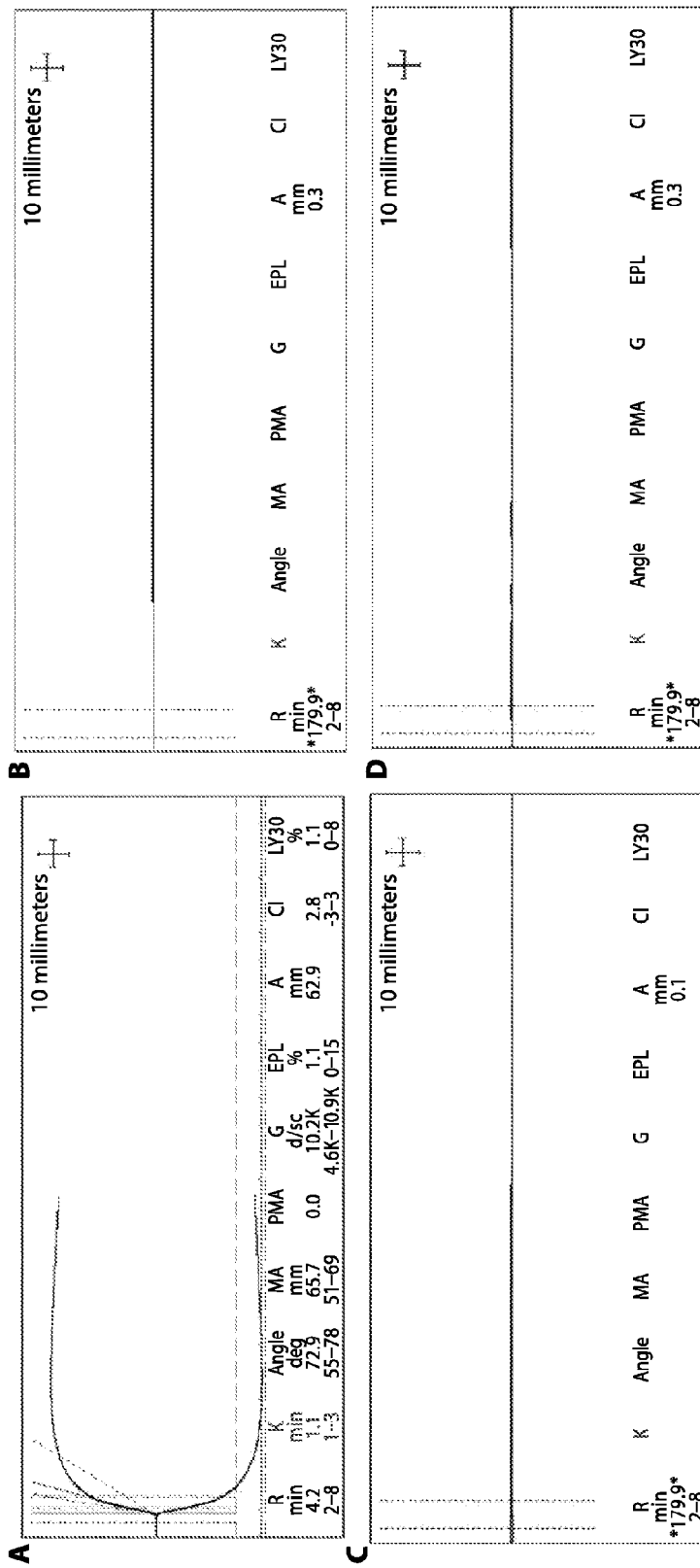

FIG. 24 Thromboelastography tracings for combinations of two anticoagulant aptamers with either kaolin or tissue factor activation. Thromboelastography tracings for blood anticoagulated and activated with A) buffer and kaolin, B) 9.3T (1 μM) + 11F7T (2 μM) and kaolin, C) 9.3T (1 μM) + R9D-14T (5 μM) and kaolin, D) 11F7T (0.5 μM) + R9D-14T (5 μM) and kaolin, E) buffer and TF, F) 7S-1 (0.5 μM) + 11F7T (2 μM) and TF, and G) 7S-1 (0.5 μM) + 9.3T (1 μM) and TF. Citrated blood (320 μL) was mixed with anticoagulant (10 μL) and kaolin or TF (10 μL), and the assay was initiated by the addition of calcium chloride (20 μL). The data are representative of data for 3 different donors. 7S-1: Factor VIIa aptamer; 9.3T: Factor IXa aptamer; 11F7T: Factor Xa aptamer; and R9D-14T: prothrombin aptamer.

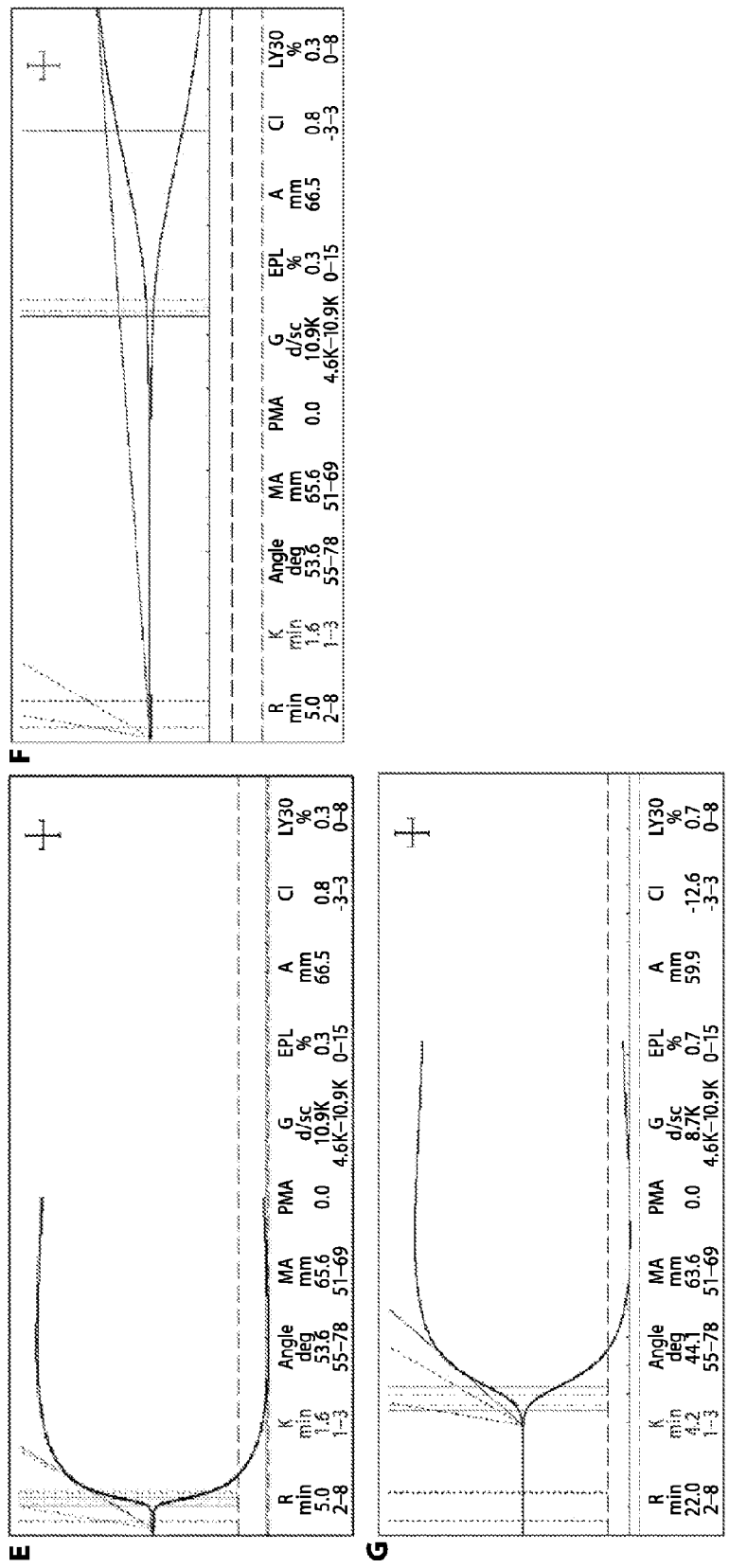

FIG. 24 Thromboelastography tracings for combinations of two anticoagulant aptamers with either kaolin or tissue factor activation. Thromboelastography tracings for blood anticoagulated and activated with A) buffer and kaolin, B) 9.3T (1 µM) + 11F7T (2 µM) and kaolin, C) 9.3T (1 µM) + R9D-14T (5 µM) and kaolin, D) 11F7T (0.5 µM) + R9D-14T (5 µM) and kaolin, E) buffer and TF, F) 7S-1 (0.5 µM) + 11F7T (2 µM) and TF, and G) 7S-1 (0.5 µM) + 9.3T (1 µM) and TF. Citrated blood (320 µL) was mixed with anticoagulant (10 µL) and kaolin or TF (10 µL), and the assay was initiated by the addition of calcium chloride (20 µL). The data are representative of data for 3 different donors. 7S-1: Factor VIIa aptamer; 9.3T: Factor IXa aptamer; 11F7T: Factor Xa aptamer; and R9D-14T: prothrombin aptamer.

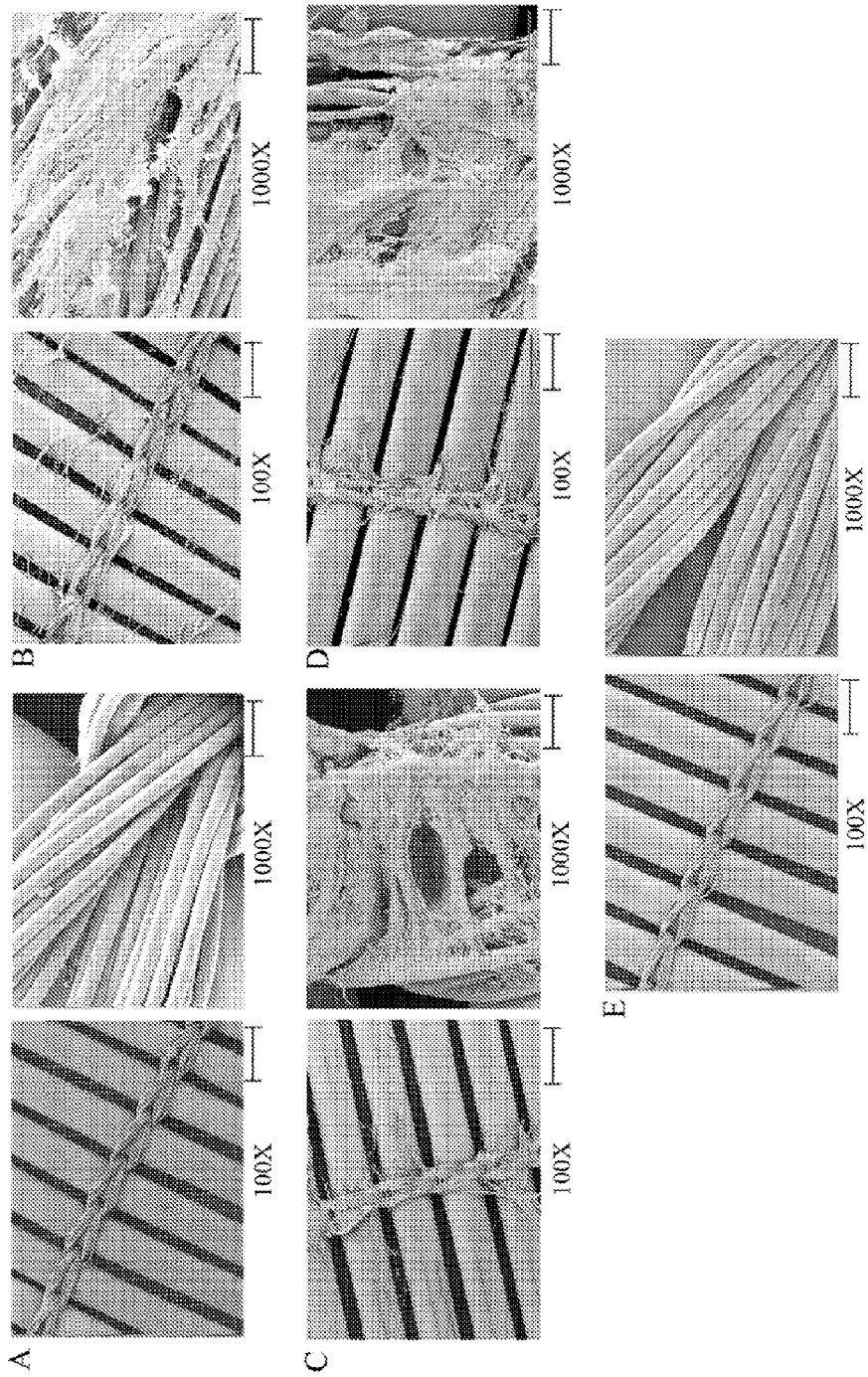

FIG. 25. Scanning electron micrographs of extracorporeal circuit oxygenator membranes from circuits with various anticoagulants. Micrograph of a membrane from an extracorporeal circuit anticoagulated with A) UFH (5 U/mL), B) 9.3T (1 μM), C) 11F7T (2 μM), D) R9D-14T (5 μM), and E) 11F7T (0.5 μM) + R9D-14T (5 μM). The images are representative of data obtained from three different areas of the membrane. Scale bar: 500 μm (100X) and 50 μm (1000X). 9.3T: Factor IXa aptamer; 11F7T: Factor Xa aptamer; and R9D-14T: prothrombin aptamer.

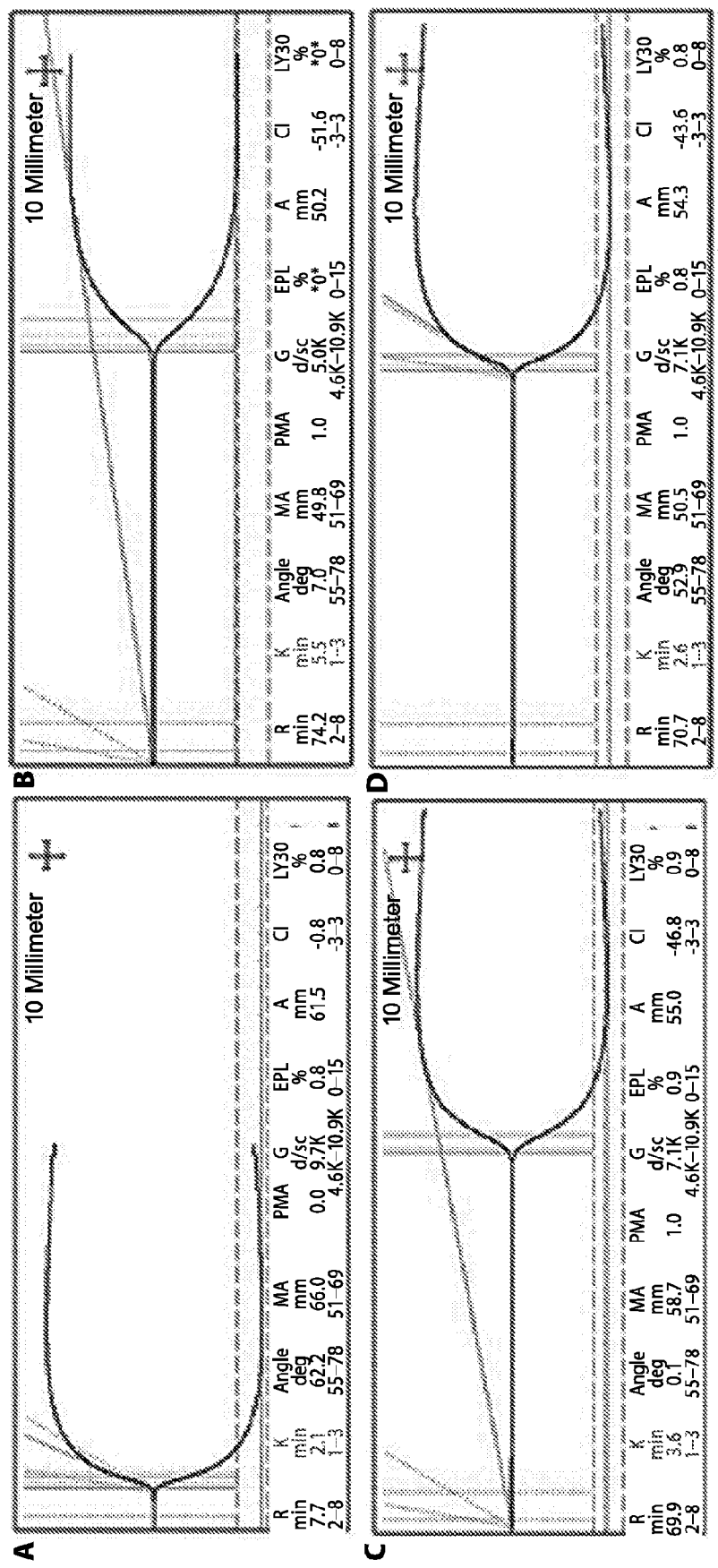

FIG. 26. Antidote reversal of the synergistic 11F7T + R9D-14T aptamer combination in thromboelastography. Thromboelastography tracings for blood stimulated with kaolin and anticoagulated with the FXa aptamer 11F7T (0.5 μM) + the prothrombin aptamer R9D-14T7 (5 μM), which was reversed with various antidotes after 1 hour of anticoagulation. A) Buffer control (no aptamer, no antidote), B) aptamers reversed with protamine (22 μM) at one hour, C) aptamers reversed with CDP universal antidote (50 μg) at one hour, D) aptamers reversed with 11F7T oligonucleotide antidote (1.5 μM) and R9D-14T oligonucleotide antidote (10 μM) at one hour, E) aptamers reversed with R9D-14T oligonucleotide antidote (10 μM) at one hour, and F) 11F7T oligonucleotide antidote (1.5 μM) at one hour. Citrated blood (320 μL) was mixed with 11F7T (5 μL) and R9D-14T (5 μL) and kaolin (10 μL), and the assay was initiated by the addition of calcium chloride (20 μL). At approximately 1 hour, antidote (10 μL) was added. The data are representative of data for 3 different donors.

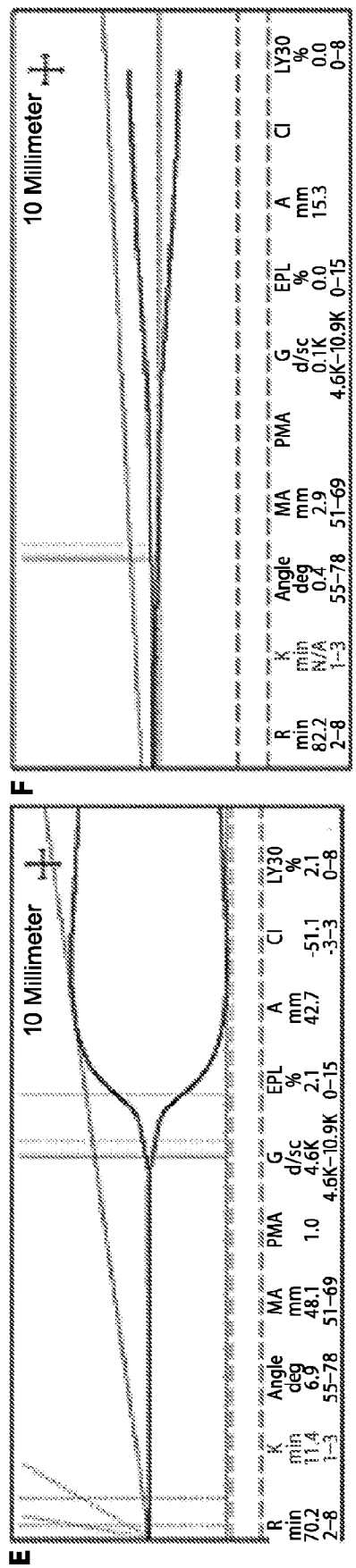

FIG. 26. Antidote reversal of the synergistic 11F7T + R9D-14T aptamer combination in thromboelastography. Thromboelastography tracings for blood stimulated with kaolin and anticoagulated with the FXa aptamer 11F7T (0.5 μM) + the prothrombin aptamer R9D-14T7 (5 μM), which was reversed with various antidotes after 1 hour of anticoagulation. A) Buffer control (no aptamer, no antidote), B) aptamers reversed with protamine (22 μM) at one hour, C) aptamers reversed with CDP universal antidote (50 μg) at one hour, D) aptamers reversed with 11F7T oligonucleotide antidote (1.5 μM) and R9D-14T oligonucleotide antidote (10 μM) at one hour, E) aptamers reversed with R9D-14T oligonucleotide antidote (10 μM) at one hour, and F) 11F7T oligonucleotide antidote (1.5 μM) at one hour. Citrated blood (320 μL) was mixed with 11F7T (5 μL) and R9D-14T (5 μL) and kaolin (10 μL), and the assay was initiated by the addition of calcium chloride (20 μL). At approximately 1 hour, antidote (10 μL) was added. The data are representative of data for 3 different donors.

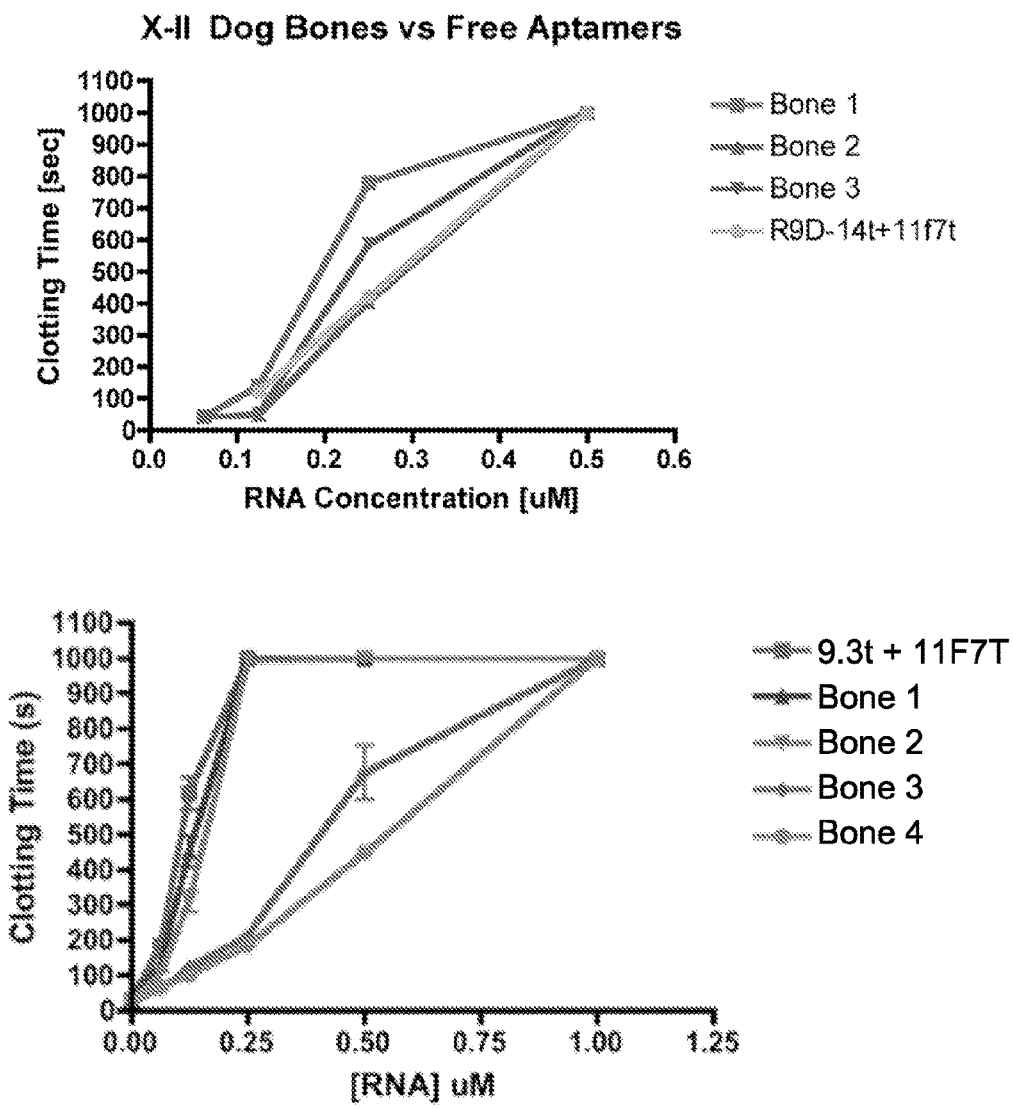
FIG. 28. Comparison of free aptamers to dogbones. Upper panel: FIX/FX dogbones versus free aptamers in an aPTT. Lower panel: FX/FII dogbones versus free aptamers in an aPTT.

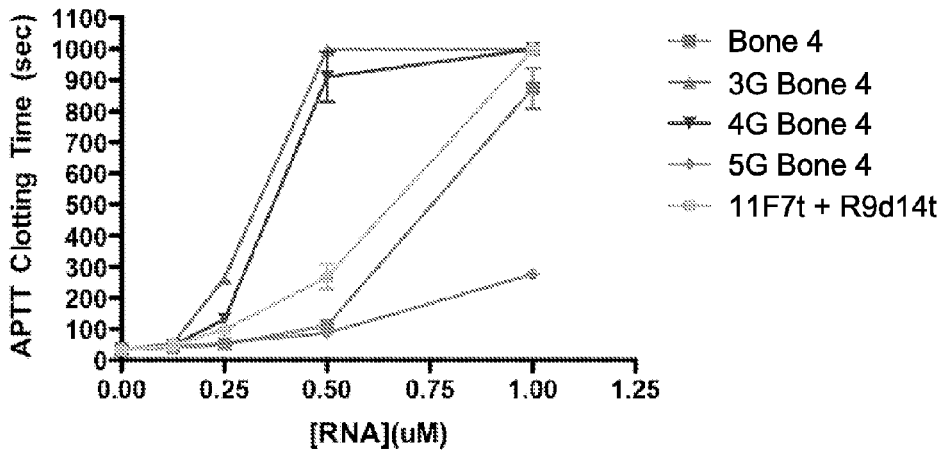

FIG. 30: a PTT data of FX/FII dogbone 4 and truncates. Clotting time of FX/FII dogbone 4 and truncates compared to the free combination of aptamers.

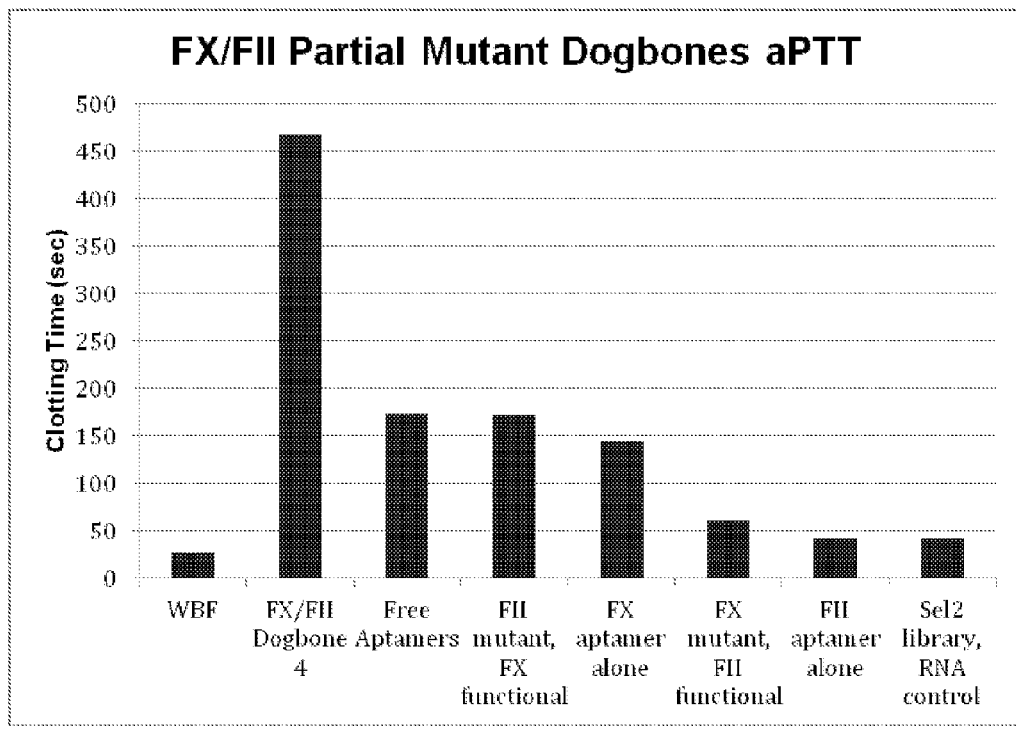

FIG. 31: Activity of partially mutated FX/FII dogbone 4 versus functional FX/FII dogbone 4 and free aptamers. Using an aPTT, we found that disrupting the activity of one aptamer in the dogbone structure does not affect the activity of the other aptamer.

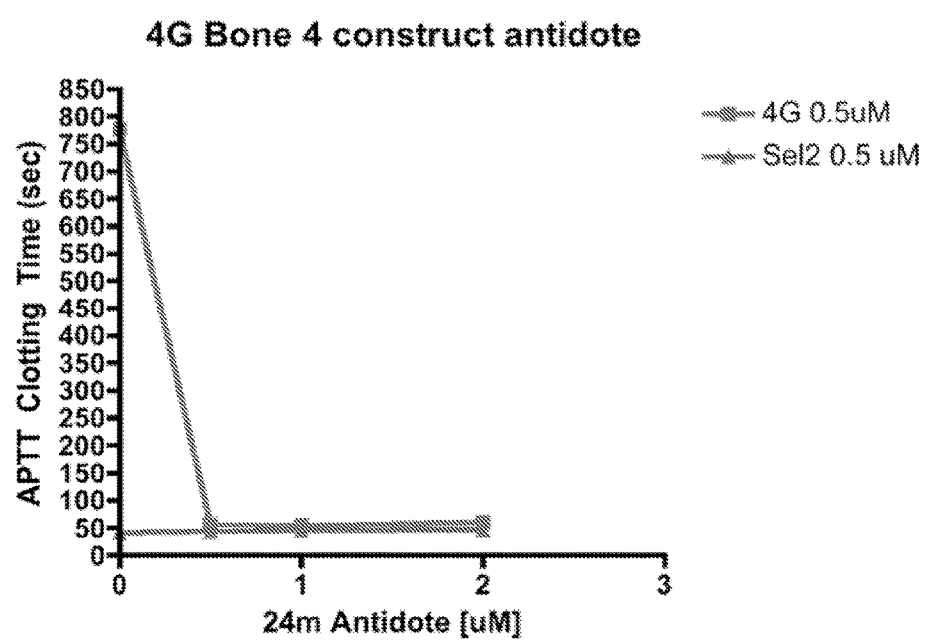
FIG. 32: Antidote Reversal of Dogbone Activity. Upper panel: sequence of 24mer antidote based on FX/FII original sequence. Lower panel: aPTT data showing reversal of the FX/FII 4G dogbone 4 anti-coagulant activity. Sel2 is a negative control of approximately the same size that should not extend clotting time.

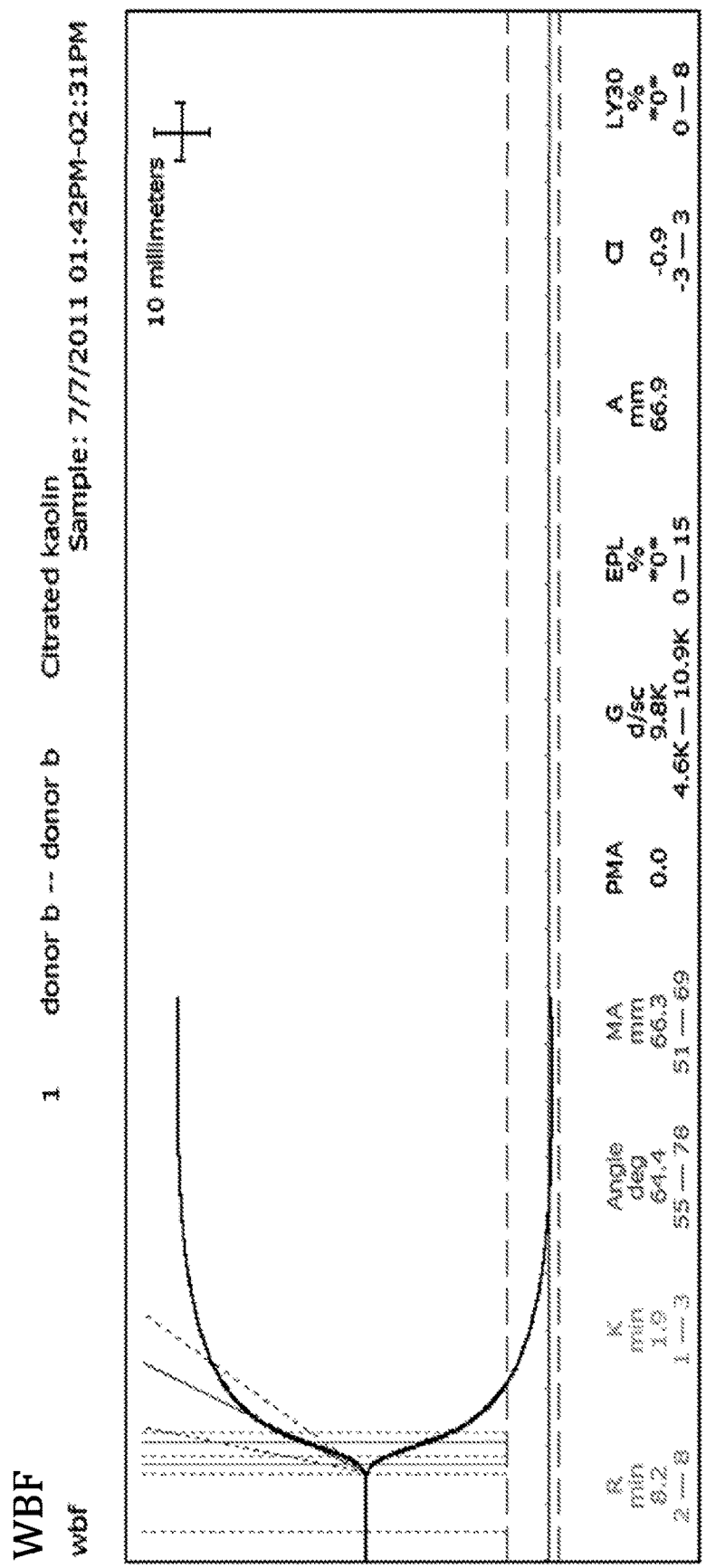
FIG. 33: TEG analysis demonstrating that Dogbone Aptamer 4 inhibits clot formation as well as the combination of individual Factor II (R9D-14T) and X (11f7T) aptamers in whole blood. WBF is whole blood without aptamer as a control.

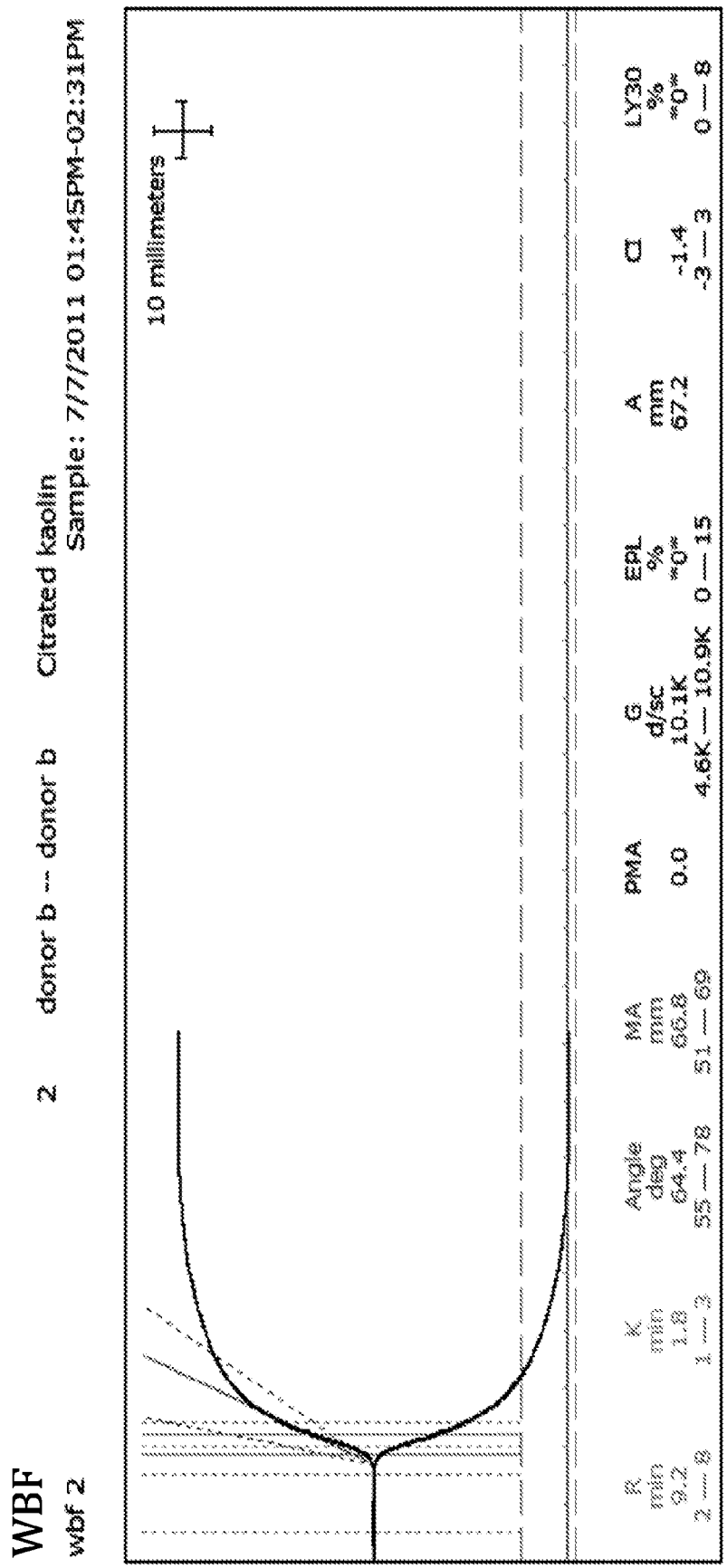
FIG. 33 cont'd-1: TEG analysis demonstrating that Dogbone Aptamer 4 inhibits clot formation as well as the combination of individual Factor II (R9D-14T) and X (11f7T) aptamers in whole blood. WBF is whole blood without aptamer as a control.

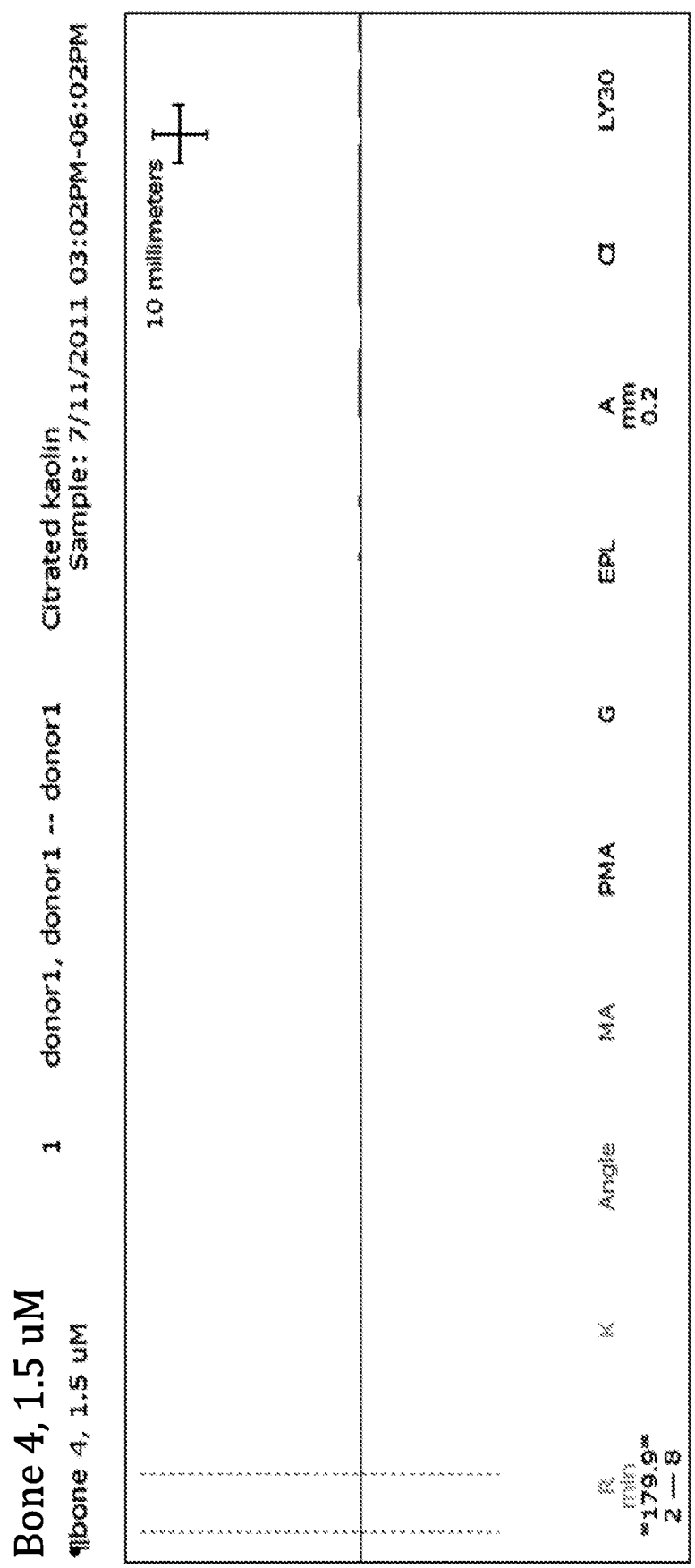
FIG. 33 cont'd-2: TEG analysis demonstrating that Dogbone Aptamer 4 inhibits clot formation as well as the combination of individual Factor II (R9D-14T) and X (11f7T) aptamers in whole blood. WBF is whole blood without aptamer as a control.

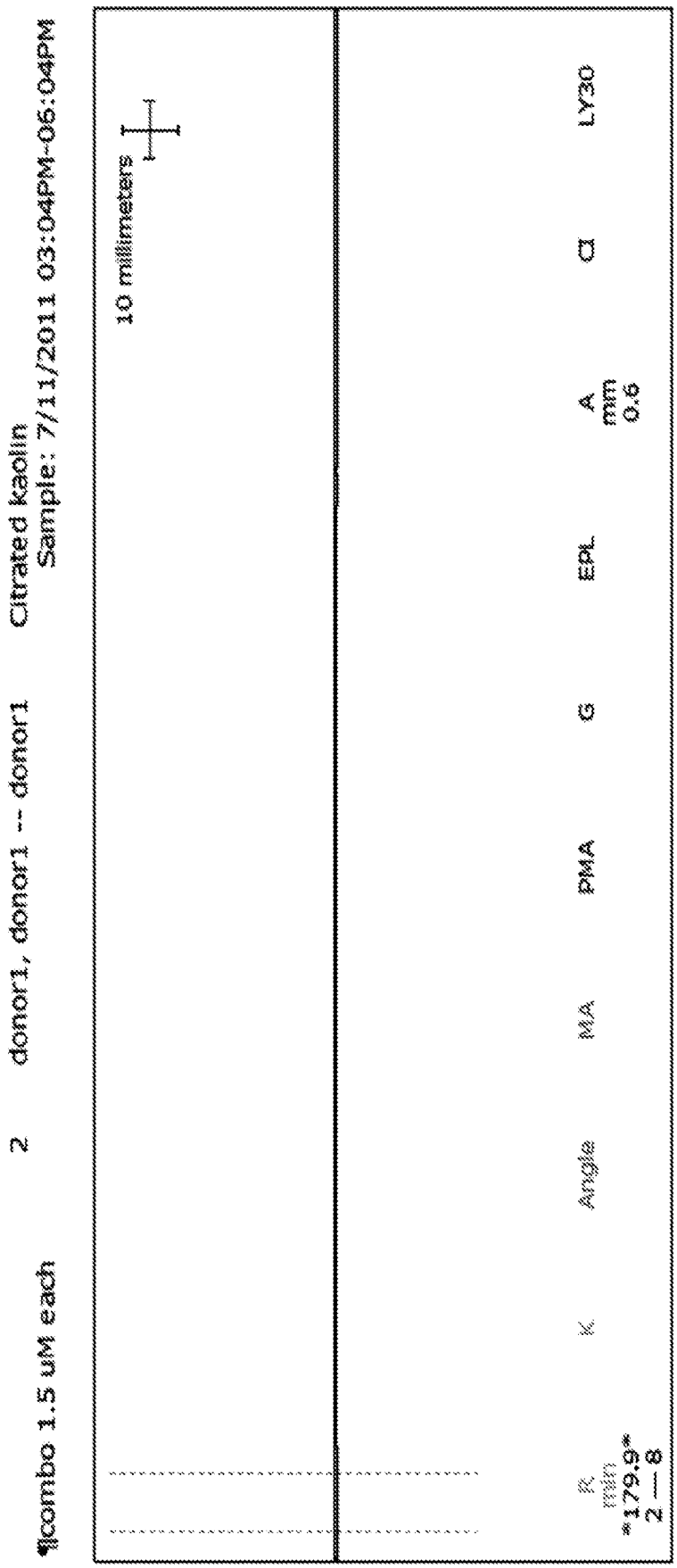
FIG. 33 cont'd-3: TEG analysis demonstrating that Dogbone Aptamer 4 inhibits clot formation as well as the combination of individual Factor II (R9D-14T) and X (11f7T) aptamers in whole blood. WBF is whole blood without aptamer as a control.

SEQUENCE LISTING

```
<160> NUMBER OF SEQ ID NOS: 24

<210> SEQ ID NO 1
<211> LENGTH: 34
<212> TYPE: RNA
<213> ORGANISM: Artificial sequence
<220> FEATURE:
<223> OTHER INFORMATION: Synthetic: 9.3T; (FIX/FIXa aptamer)

<400> SEQUENCE: 1
auggggacua uaccgcguaa ugcugccucc ccau                              34

<210> SEQ ID NO 2
<211> LENGTH: 36
<212> TYPE: RNA
<213> ORGANISM: Artificial sequence
<220> FEATURE:
<223> OTHER INFORMATION: Synthetic: 11F7T; (FX/Fxa aptamer)

<400> SEQUENCE: 2
gagagcccca gcgagauaau acuuggcccc gcucuu                            36

<210> SEQ ID NO 3
<211> LENGTH: 58
<212> TYPE: DNA
<213> ORGANISM: Artificial sequence
<220> FEATURE:
<223> OTHER INFORMATION: Synthetic: R9D-14T7; (FII/FIIa aptamer)

<400> SEQUENCE: 3
ggcggtcgat cacacagttc aaacgtaata agccaatgta cgaggcagac gactcgcc    58

<210> SEQ ID NO 4
<211> LENGTH: 34
<212> TYPE: RNA
<213> ORGANISM: Artificial sequence
<220> FEATURE:
<223> OTHER INFORMATION: Synthetic: 9.3Trnut; (FIX/FIXa aptamer)

<400> SEQUENCE: 4
auggggacug ugccgcguaa ugcugccucc ccau                              34

<210> SEQ ID NO 5
<211> LENGTH: 80
<212> TYPE: RNA
<213> ORGANISM: Artificial sequence
<220> FEATURE:
<223> OTHER INFORMATION: Synthetic: 7S-1; (FVII/FVIIa aptamer)

<400> SEQUENCE: 5
gggaggacga ugcggacucc uccaagcgac caacaucggu cccguuucag aucaacagac  60
gacucgcuga ggauccgaga                                              80

<210> SEQ ID NO 6
<211> LENGTH: 36
<212> TYPE: RNA
<213> ORGANISM: Artificial sequence
<220> FEATURE:
<223> OTHER INFORMATION: Synthetic: 11F7Trnut; (FX/Fxa aptamer)

<400> SEQUENCE: 6
gagagcccca gcgagauaau acuuguaccc gcucuu                            36

<210> SEQ ID NO 7
<211> LENGTH: 58
```

```
<212> TYPE: DNA
<213> ORGANISM: Artificial sequence
<220> FEATURE:
<223> OTHER INFORMATION: Synthetic: R9D-14Tmut  (FII/FIIa aptamer)

<400> SEQUENCE: 7
ggcggtcgat cacacagttc aaacgtaata agccggcgta cgaggcagac gactcgcc        58

<210> SEQ ID NO 8
<211> LENGTH: 80
<212> TYPE: RNA
<213> ORGANISM: Artificial sequence
<220> FEATURE:
<223> OTHER INFORMATION: Synthetic: 7S-1mut; (FVII/FVIIa aptamer)

<400> SEQUENCE: 8
gggaggacga ugcggacucc uccaagcgac caacaucggu cuuauuucag aucaacagac      60
gacucgcuga ggauccgaga                                                  80

<210> SEQ ID NO 9
<211> LENGTH: 15
<212> TYPE: DNA
<213> ORGANISM: Artificial sequence
<220> FEATURE:
<223> OTHER INFORMATION: Synthetic: 11F7T DNA antidote

<400> SEQUENCE: 9
tattatctcg ctggg                                                       15

<210> SEQ ID NO 10
<211> LENGTH: 20
<212> TYPE: DNA
<213> ORGANISM: Artificial sequence
<220> FEATURE:
<223> OTHER INFORMATION: Synthetic: R9D- 14T DNA antidote

<400> SEQUENCE: 10
gtctgcctcg tacattggct                                                  20

<210> SEQ ID NO 11
<211> LENGTH: 65
<212> TYPE: PRT
<213> ORGANISM: Artificial sequence
<220> FEATURE:
<223> OTHER INFORMATION: Synthetic: Lepirudin amino acid sequence

<400> SEQUENCE: 11

Leu Thr Tyr Thr Asp Cys Thr Glu Ser Gly Gln Asn Leu Cys Leu Cys
1               5                   10                  15

Glu Gly Ser Asn Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
        35                  40                  45

Gln Ser His Asn Asp Gly Asp Phe Glu Glu Ile Pro Glu Glu Tyr Leu
    50                  55                  60

Gln
65

<210> SEQ ID NO 12
<211> LENGTH: 20
<212> TYPE: PRT
<213> ORGANISM: Artificial sequence
<220> FEATURE:
<223> OTHER INFORMATION: Synthetic: Bivalirudin amino acid sequence
```

-continued

```
<400> SEQUENCE: 12

Phe Pro Arg Pro Gly Gly Gly Gly Asn Gly Asp Phe Glu Glu Ile Pro
1               5                   10                  15

Glu Glu Tyr Leu
            20

<210> SEQ ID NO 13
<211> LENGTH: 58
<212> TYPE: RNA
<213> ORGANISM: Artificial sequence
<220> FEATURE:
<223> OTHER INFORMATION: Synthetic: R9D-14T7 (FII/FIIa aptamer)

<400> SEQUENCE: 13
ggcggucgau cacacaguuc aaacguaaua agccaaugua cgaggcagac gacucgcc         58

<210> SEQ ID NO 14
<211> LENGTH: 58
<212> TYPE: RNA
<213> ORGANISM: Artificial sequence
<220> FEATURE:
<223> OTHER INFORMATION: Synthetic: R9D-14T7 mutant (FII/FIIa aptamer)

<400> SEQUENCE: 14
ggcggucgau cacacaguuc aaacguaaua agccggcgua cgaggcagac gacucgcc         58

<210> SEQ ID NO 15
<211> LENGTH: 101
<212> TYPE: RNA
<213> ORGANISM: Artificial sequence
<220> FEATURE:
<223> OTHER INFORMATION: Synthetic: 9.3T/11F7T Bone 1; 27A

<400> SEQUENCE: 15
gguggauggg gacuauaccg cguaaugcug ccuccccauc caccaaauag cacguagaga       60
gccccagcga gauaauacuu ggccccgcuc uuuacgugcu a                          101

<210> SEQ ID NO 16
<211> LENGTH: 87
<212> TYPE: RNA
<213> ORGANISM: Artificial sequence
<220> FEATURE:
<223> OTHER INFORMATION: Synthetic: 9.3T/11F7T Bone 2; 27B

<400> SEQUENCE: 16 ggaugggggac uauaccgcgu aaugcugccu ccccauccaa aacguagaga gccccagcga      60
gauaauacuu ggccccgcuc uuuacgu                                          87

<210> SEQ ID NO 17
<211> LENGTH: 73
<212> TYPE: RNA
<213> ORGANISM: Artificial sequence
<220> FEATURE:
<223> OTHER INFORMATION: Synthetic: 9.3T/11F7T Bone 3; 27C

<400> SEQUENCE: 17 gggggggacua uaccgcguaa ugcugccucc ccccaaagag agccccagcg agauaauacu      60
uggccccgcu cuu                                                         73

<210> SEQ ID NO 18
<211> LENGTH: 60
<212> TYPE: RNA
```

<213> ORGANISM: Artificial sequence
<220> FEATURE:
<223> OTHER INFORMATION: Synthetic: 9.3T/11F7T Bone 4;27D

<400> SEQUENCE: 18

```
ggacuauacc gcguaaugcu gccuccagag ccccagcgag auaauacuug gccccgcucu    60
```

<210> SEQ ID NO 19
<211> LENGTH: 111
<212> TYPE: RNA
<213> ORGANISM: Artificial sequence
<220> FEATURE:
<223> OTHER INFORMATION: Synthetic: R9D-14TT/11F7T Bone 1;27E

<400> SEQUENCE: 19

```
ggggcggucg aucacacagu ucaaacguaa uaagccaaug uacgaggcag acgacucgcc    60
ccaaaacgua gagagcccca gcgagauaau acuuggcccc gcucuuuacg u            111
```

<210> SEQ ID NO 20
<211> LENGTH: 97
<212> TYPE: RNA
<213> ORGANISM: Artificial sequence
<220> FEATURE:
<223> OTHER INFORMATION: Synthetic: R9D-14TT/11F7T Bone 2; 27F

<400> SEQUENCE: 20

```
ggcggucgau cacacaguuc aaacguaaua agccaaugua cgaggcagac gacucgccaa    60
agagagcccc agcgagauaa uacuuggccc cgcucuu                             97
```

<210> SEQ ID NO 21
<211> LENGTH: 87
<212> TYPE: RNA
<213> ORGANISM: Artificial sequence
<220> FEATURE:
<223> OTHER INFORMATION: Synthetic: R9D-14TT/11F7T Bone 3; 27G

<400> SEQUENCE: 21

```
gggucgauca cacaguucaa acguaauaag ccaauguacg aggcagacga cuccaaaagc    60
cccagcgaga uaauacuugg ccccgcu                                        87
```

<210> SEQ ID NO 22
<211> LENGTH: 81
<212> TYPE: RNA
<213> ORGANISM: Artificial sequence
<220> FEATURE:
<223> OTHER INFORMATION: Synthetic: R9D-14TT/11F7T Bone 4; 29A

<400> SEQUENCE: 22

```
gucgaucaca caguucaaac guaauaagcc aauguacgag gcagacgaca agccccagc     60 gagauaauac uuggccccgc u                                              81
```

<210> SEQ ID NO 23
<211> LENGTH: 85
<212> TYPE: RNA
<213> ORGANISM: Artificial sequence
<220> FEATURE:
<223> OTHER INFORMATION: Synthetic: R9D-14TT/11F7T Bone 4 3G;29B

<400> SEQUENCE: 23

```
gggucgauca cacaguucaa acguaauaag ccaauguacg aggcagacga cccaaagccc    60
cagcgagaua auacuuggcc ccgcu                                          85
```

```
<210> SEQ ID NO 24
<211> LENGTH: 81
<212> TYPE: RNA
<213> ORGANISM: Artificial sequence
<220> FEATURE:
<223> OTHER INFORMATION: Synthetic: R9D-14TT/11F7T Bone 4 4G; 29C

<400> SEQUENCE: 24
ggggaucaca caguucaaac guaauaagcc aauguacgag gcagacccca aagccccagc      60
gagauaauac uuggccccgc u                                               81
```

METHOD OF CONTROLLING COAGULATION

This application is a national stage application filed under 35 U.S.C. 371 of International Application No. PCT/2012/036783, filed May 7, 2012, which claims priority from U.S. Provisional Application No. 61/457,642, filed May 5, 2011, the entire content of both of which are incorporated herein by reference.

This invention was made with government support under Grant No. HL065222 awarded by the National Institutes of Health. The government has certain rights in the invention.

TECHNICAL FIELD

The present invention relates, in general, to methods of controlling coagulation, and in particular, to methods of effecting neutralizable rapid onset anticoagulation, and to compounds and compositions suitable for use in such methods.

BACKGROUND

Fibrin blood clot formation is mediated by a series of enzymatic reactions that occur on cellular and vascular surfaces. The coagulation proteins circulate in the blood as inactive proteins (zymogens) and upon stimulation are proteolyzed to generate active enzymes. Traditional coagulation models represent the series of reactions as a Y-shaped "cascade" with two separate pathways—the extrinsic and intrinsic pathway—that ultimately converge into a final common pathway (Macfarlane, Nature 202:498-9 (1964), Davie and Ratnoff, Science 145:1310-2 (1964)). Thrombin is the final enzyme formed in the coagulation cascade, and the rate of thrombin formation, as well as the amount of thrombin formed directly influences fibrin clot stability and structure (Wolberg, Blood Rev 21:131-42 (2007)).

Inappropriate thrombin generation can result in pathological blood clot formation, termed thrombosis. The treatment of patients with thrombosis almost always includes the administration of an anticoagulant therapeutic to impair procoagulant protein function and prevent blood coagulation. Researchers currently debate the optimal therapeutic target as the degree of anticoagulation required varies depending on the clinical indication. For example, lower levels of anticoagulation are desired for prophylactic treatment of high risk patients, while potent anticoagulation is required during surgical procedures, such as cardiopulmonary bypass (CPB), to treat thrombosis.

Genetic studies with knockout mice have been performed to study the role of each coagulation protein and pathway specific responses. Although Hemophilic mice (FVIII or FIX deficiency) have been extensively studied to discern the role of these proteins during in vivo coagulation, genetically null mice for TF, FVII, FX, and prothrombin are not viable, making similar studies unfeasible (Mackman, Arterioscler Thromb Vasc Biol 25: 2273-81 (2005)). Alternatively, inhibiting clotting proteins with currently available anticoagulant therapeutics can functionally remove the enzyme from the system and thereby clarify the role of these proteins in clot formation. Although small molecule anticoagulants have been generated toward a few coagulation enzymes (i.e., thrombin and FXa), it has been challenging to design similar compounds toward the upstream coagulation enzymes (i.e., FVIIa and FIXa). Thus, alternative classes of therapeutics that can be applied to inhibit all of the procoagulant proteins are needed to fully probe and directly compare the contributions of each pathway.

Aptamers, or single-stranded oligonucleotides, are nucleic acid ligands that bind specifically to their therapeutic targets with high affinity. Aptamers can be generated against target molecules, such as soluble coagulation proteins, by screening combinatorial oligonucleotide libraries for high affinity binding to the target (Ellington and Szostak, Nature 1990; 346: 8 18-22 (1990), Tuerk and Gold, Science 249: 505-10 (1990). This selection method has been employed to generate modified RNA aptamers that bind specifically to coagulation factor VIIa (FVIIa) (Layzer and Sullenger, Oligonucleotides 17:1-11 (2007)), factor IXa (FIXa) (Rusconi et al, Nature 419: 90-4 (2002)), factor X (FXa) (Buddai et al, J Biol Chem 285:52 12-23 (2010)), or prothrombin (Layzer and Sullenger, Oligonucleotides 17:1-11 (2007), Bompiani et al, J Thromb Haemost 10:870-80 (2012). All of the aptamers bind to both the zymogen and enzyme form of the protein, and mechanistic studies with the FIXa, FXa, and prothrombin aptamers indicate that the aptamers bind a large surface area on the zymogen/enzyme that is critical for procoagulant protein-protein interactions (Buddai et al, J Biol Chem 285:52 12-23 (2010), Bompiani et al, J Thromb Haemost 10:870-80 (2012), Long et al, RNA 14:1-9 (2008), Sullenger et al, J Biol Chem 287:12779-86 (2012)). Moreover, two independent types of antidotes have been developed that can rapidly modulate aptamer anticoagulant function, which increases the safety profile of these anticoagulants (Rusconi et al, Nature 419: 90-4 (2002), Oney et al, Nat Med 15:1224-8 (2009)). Currently, an optimized version of the FIXa aptamer and its antidote are in phase two clinical trials for thrombotic indications (Cohen et al, Circulation 122:614-22 (2010), Povsic et al, Eur Heart J 32:2412-9 (2011)). The phase one clinical data indicate that this aptamer is well tolerated, safe, and can be rapidly modulated with the antidote (Dyke et al, Circulation 2006; 114:2490-7 (2006), Chan et al, Circulation 117:2865-74 (2008), Chan et al, J Thromb Haemost 6: 789-96 (2008)).

The present invention results, at least in part, from studies designed to compare the effects of the FVIIa, FIXa, FXa, and prothrombin anticoagulant aptamers in several in vitro clotting assays to assess the impact of inhibiting coagulation proteins in the different pathways. Additionally, the effects of simultaneously inhibiting two proteins within the same or different pathways by combining two aptamers were analyzed. These anticoagulant aptamers were also tested in a clinically relevant model of ex vivo extracorporeal circulation and their ability to be controlled with an antidote was assessed. The results demonstrate that aptamers are a unique class of anticoagulants that can be used individually or in combination, yet still safely controlled with antidotes.

SUMMARY OF THE INVENTION

In general, the present invention relates to methods of controlling coagulation. More specifically, the invention relates to methods of effecting neutralizable rapid onset anticoagulation. The invention further relates to compounds and compositions suitable for use in such methods.

Objects and advantages of the present invention will be clear from the description that follows.

BRIEF DESCRIPTION OF THE DRAWINGS

FIGS. 14A-14D. Clot formation in whole blood added to the cup of a TEG analyzer was induced by the addition of TF. The blood was pretreated with either no anticoagulant (FIG. 14A) (buffer), or with (FIG. 14B) factor VIIa (FVIIa) aptamer, (FIG. 14C) FIXa aptamer, or (FIG. 14D) FXa aptamer, at the concentrations indicated.

FIGS. 15A-15D. Clot formation in whole blood added to the cup of a TEG analyzer was induced by the addition of kaolin. The blood was pretreated with either no anticoagulant (FIG. 15A) (buffer), (FIG. 15B) FIXa aptamer, (FIG. 15C) FXa aptamer, or (FIG. 15D) thrombin aptamer, at the concentrations indicated.

FIGS. 16A-16E. Clot formation in whole blood added to the cup of a TEG analyzer was induced by the addition of kaolin. The blood was pretreated with either (FIG. 16A) no anticoagulant (buffer), (FIG. 16B) FIXa aptamer+FXa aptamer, (FIG. 16C) FIXa aptamer+thrombin aptamer, or (FIG. 16D) FXa aptamer+thrombin aptamer, at the concentrations indicated. For comparison, a TEG assay was also performed on whole blood pretreated with (FIG. 16E) 5 U/mL UFH, the approximate UFH concentration recommended for CPB anticoagulation.

FIGS. 17A-17C. Clot formation in whole blood added to the cup of a TEG analyzer was induced by the addition of kaolin. The blood was pretreated with either (FIG. 17A) FIXa aptamer 0.5 micromolar, (FIG. 17B) lepirudin 6.4 micrograms/mL (0.860 micromolar), or (FIG. 17C) FIXa aptamer 0.5 micromolar+lepirudin 1.6 micrograms/mL (0.215 micromolar).

FIG. 19. The M-fold predicted secondary structures of the four modified RNA anticoagulant aptamers and their point mutants. FIG. 19 shows the sequence and structures for 7S-1 (FVII/FVIIa) aptamer (SEQ ID NO: 5); 9.3T (FIX/FIXa) aptamer (SEQ ID NO: 1); 11F7T (FX/FXa) aptamer (SEQ ID NO: 2); and R9D-14T (prothrombin/thrombin) aptamer (SEQ ID NO: 3).

FIGS. 20A and 20B. Dose titrations with each of the four anticoagulant aptamers in clinical aPTT and PT plasma clotting assays. FIG. 20A) Dose titration response with individual aptamers in the activated partial thromboplastin time (aPTT) assay. FIG. 20B) Dose titration response with the individual aptamers in the prothrombin time (PT) assay. The data represent the mean±SEM of duplicates; the lines were arbitrarily drawn. 7S-1: FVIIa aptamer; 9.3T: FIXa aptamer; 11F7T: FXa aptamer; and R9D-14T: prothrombin aptamer.

FIGS. 21A-21D. Dose titrations with each of the four anticoagulant aptamers in calibrated automated thrombography. Thrombograms with various concentrations of FIG. 21A) 7S-1 with 5 pM TF; FIG. 21B) 9.3T with 1 pM TF; FIG. 21C) 11F7T with 5 pM TF; and FIG. 21D) R9D-14T with 5 pM TF. For 5,000 nM R9D-14T there was no thrombin generation detected. Platelet poor plasma (80 µL) was incubated with aptamer (10 µL) at 37° C. for 5 min, TF was added (20 µL) and incubated at 37° C. for another 5 min. The assay was initiated with the addition of FluCa substrate (10 µL) and thrombin generation was measured at 37° C. for 1 hour. The data represent the mean of duplicates. 7S-1: Factor VIIa aptamer; 9.3T: Factor IXa aptamer; 11F7T: Factor Xa aptamer; and R9D-14T: prothrombin aptamer.

FIGS. 22A-22I. Thromboelastography tracings for saturating concentrations of each of the four anticoagulant aptamers with either kaolin or tissue factor activation. Thromboelastography tracings for blood anticoagulated and activated with FIG. 22A) buffer control with kaolin, FIG. 22B) 9.3T (1 µM) and kaolin, FIG. 22C) 11F7T (2 µM) and kaolin, FIG. 22D) R9D-14T (5 µM) and kaolin, FIG. 22E) buffer with TF, FIG. 22F) 7S-1 (0.5 µM) and TF, FIG. 22G) 9.3T (1 µM) and TF, FIG. 22H) 11F7T (2 µM) and TF, and FIG. 22I) R9D-14T (5 µM) and TF. Blood was drawn from a healthy volunteer and citrated. Citrated blood (320 µL) was mixed with aptamer (10 µL) and either kaolin or TF (10 µL), and the assay was initiated by the addition of calcium chloride (20 µL). The data are representative of data for 3 different donors. 7S-1: Factor VIIa aptamer; 9.3T: Factor IXa aptamer; 11F7T: Factor Xa aptamer; and R9D-14T: prothrombin aptamer.

FIGS. 23A and 23B. Combinations of two anticoagulant aptamers in the clinical aPTT and PT plasma clotting assays. FIG. 23A) Dose titration for combinations of two aptamers in the aPTT assay. The x-axis represents the total RNA concentration, where each aptamer is present at an equimolar concentration. FIG. 23B) Dose titration for combinations of two aptamers in the PT assay. The x-axis represents the total RNA concentration, where each aptamer is present in an equimolar concentration. The data represent the mean±SEM of duplicates; the lines were arbitrarily drawn. 7S-1: Factor VIIa aptamer; 9.3T: Factor IXa aptamer; 11F7T: Factor Xa aptamer; and R9D-14T: prothrombin aptamer.

FIGS. 24A-24G. Thromboelastography tracings for combinations of two anticoagulant aptamers with either kaolin or tissue factor activation. Thromboelastography tracings for blood anticoagulated and activated with FIG. 24A) buffer and kaolin, FIG. 24B) 9.3T (1 µM)+11F7T (2 µM) and kaolin, FIG. 24C) 9.3T (1 µM)+R9D-14T (5 µM) and kaolin, FIG. 24D) 11F7T (0.5 µM)+R9D-14T (5 µM) and kaolin, FIG. 24E) buffer and TF; FIG. 24F) 7S-1 (0.5 µM)+11F7T (2 µM) and TF, and FIG. 24G) 7S-1 (0.5 µM)+9.3T (1 µM) and TF. Citrated blood (320 µL) was mixed with anticoagulant (10 µL) and kaolin or TF (10 µL), and the assay was initiated by the addition of calcium chloride (20 µL). The data are representative of data for 3 different donors. 7S-1: Factor VIIa aptamer; 9.3T: Factor IXa aptamer; 11F7T: Factor Xa aptamer; and R9D-14T: prothrombin aptamer.

FIGS. 25A-25E. Scanning electron micrographs of extracorporeal circuit oxygenator membranes from circuits with various anticoagulants. Micrograph of a membrane from an extracorporeal circuit anticoagulated with FIG. 25A) UFH (5 U/mL), FIG. 25B) 9.3T (1 µM), FIG. 25C) 11F7T (2 µM), FIG. 25D) R9D-14T (5 µM), and FIG. 25E) 11F7T (0.5 µM)+R9D-14T (5 µM). The images are representative of data obtained from three different areas of the membrane. Scale bar: 500 µm (100×) and 50 µm (1000×). 9.3T: Factor IXa aptamer; 11F7T: Factor Xa aptamer; and R9D-14T: prothrombin aptamer.

FIGS. 26A-26F. Antidote reversal of the synergistic 11F7T+R9D-14T aptamer combination in thromboelastography. Thromboelastography tracings for blood stimulated with kaolin and anticoagulated with the FXa aptamer 11F7T (0.5 μM)+the prothrombin aptamer R9D-14T7 (5 μM), which was reversed with various antidotes after 1 hour of anticoagulation. FIG. 26A) Buffer control (no aptamer, no antidote), FIG. 26B) aptamers reversed with protamine (22 μM) at one hour, FIG. 26C) aptamers reversed with CDP universal antidote (50 μg) at one hour, FIG. 26D) aptamers reversed with 11F7T oligonucleotide antidote (1.5 μM) and R9D-14T oligonucleotide antidote (10 μM) at one hour, FIG. 26E) aptamers reversed with R9D-14T oligonucleotide antidote (10 μM) at one hour, and FIG. 26F) 11F7T oligonucleotide antidote (1.5 μM) at one hour. Citrated blood (320 μL) was mixed with 11F7T (5 μL) and R9D-14T (5 μL) and kaolin (10 μL), and the assay was initiated by the addition of calcium chloride (20 μL). At approximately 1 hour, antidote (10 μL) was added. The data are representative of data for 3 different donors.

FIGS. 27A-27D show mFold prediction of FIX/FX dogbones. FIG. 27A: 9.3T/11F7T Bone 1 structure and sequence (SEQ ID NO: 15). FIG. 27B: 9.3T/11F7T Bone 2 structure and sequence (SEQ ID NO: 16). FIG. 27C: 9.3T/11F7T Bone 3 structure and sequence (SEQ ID NO: 17). FIG. 27D: 9.3T/11F7T Bone 4 structure and sequence (SEQ ID NO: 18). FIGS. 27E-27G show mFold prediction of FX/FII dogbones. FIG. 27E: R9D-14TT/11F7T Bone 1 structure and sequence (SEQ ID NO: 19). FIG. 27F: R9D-14TT/11F7T Bone 2 structure and sequence (SEQ ID NO: 20). FIG. 27G: R9D-14TT/11F7T Bone 3 structure and sequence (SEQ ID NO: 21).

FIG. 28: Comparison of free aptamers to dogbones. Upper panel: FIX/FX dogbones versus free aptamers in an aPTT. Lower panel: FX/FII dogbones versus free aptamers in an aPTT.

FIG. 29A: original dogbone 4 structure and sequence (SEQ ID NO: 22). FIG. 29B: 3G dogbone 4 structure and sequence (SEQ ID NO: 23). FIG. 29C: 4G dogbone 4 structure and sequence (SEQ ID NO: 24). Not pictured: 5G dogbone 4 structure and sequence.

FIG. 30: aPTT data of FX/FII dogbone 4 and truncates. Clotting time of FX/FII dogbone 4 and truncates compared to the free combination of aptamers.

FIG. 31: Activity of partially mutated FX/FII dogbone 4 versus functional FX/FII dogbone 4 and free aptamers. Using an aPTT, we found that disrupting the activity of one aptamer in the dogbone structure does not affect the activity of the other aptamer.

FIG. 32: Antidote Reversal of Dogbone Activity. Upper panel: sequence of 24mer antidote based on FX/FII original sequence. Lower panel: aPTT data showing reversal of the FX/FII 4G dogbone 4 anti-coagulant activity. Sel2 is a negative control of approximately the same size that should not extend clotting time.

FIG. 33: TEG analysis demonstrating that Dogbone Aptamer 4 inhibits clot formation as well as the combination of individual Factor II (R9D-14T) and X (11f7T) aptamers in whole blood. WBF is whole blood without aptamer as a control.

DETAILED DESCRIPTION OF THE INVENTION

Figure 1:
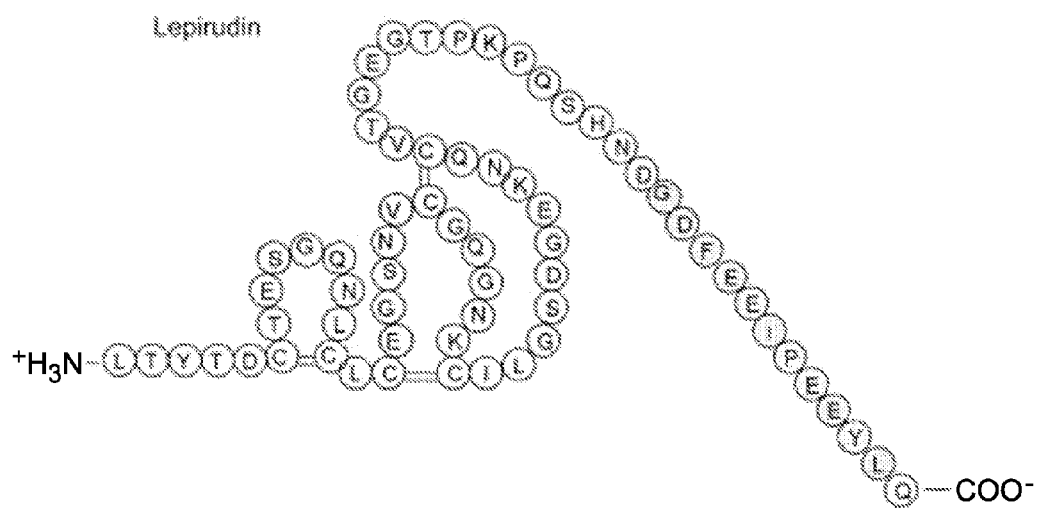
FIG. 1. Amino acid sequence of lepirudin (SEQ ID NO: 11).

Each year in the U. S. an estimated 12 million in-patients require a rapid onset anticoagulant (ROA), a drug that effects systemic anticoagulation within two minutes of its intravenous infusion. Four ROAs have received FDA approval: unfractionated heparin (UFH) in 1939, lepirudin in 1998, bivalirudin in 2000, and argatroban in 2000. UFH effects anticoagulation via several indirect mechanisms. Its principal mechanism becomes initiated when it binds antithrombin (AT), a constitutive circulating serine protease inhibitor. UFH to AT binding induces in AT a conformational change that accelerates AT's inhibition of thrombin and several other procoagulant proteases. In contrast to UFH, each of the other three ROAs effects anticoagulation via a single direct mechanism—the inhibition of thrombin through the direct and specific binding of thrombin.

Each approved ROA has important disadvantages. UFH cannot inhibit clot-bound thrombin, it has unpredictable pharmacologic activity and can cause heparin-induced thrombocytopenia, a complication that can result in limb loss and organ failure. UFH's interaction with its antidote, protamine, triggers systemic inflammation by activating the classical complement and cyclooxygenase pathways. At concentrations recommended for cardiopulmonary bypass, the most thrombogenic indication for rapid onset anticoagulation, each direct thrombin inhibitor (DTI) effects less intense anticoagulation than UFH. As important, each DTI also lacks an antidote.

A neutralizable non-UFH anticoagulation strategy that can achieve the intensity of UFH-induced anticoagulation remains an important unmet medical need. The present invention relates to methods of effecting rapid onset anticoagulation that meet that need.

Aptamers

In certain embodiments, the present method of effecting neutralizable rapid onset anticoagulation involves the administration (e.g., intravenous (IV) administration) to a subject (e.g., a human or non-human mammal) of at least one aptamer. Aptamers can be identified from recombinant oligonucleotide libraries with an in vitro selection technique called SELEX (Tuerk and Gold, Science 249:505-510 (1990)). SELEX has facilitated the identification of several anticoagulant aptamers, each of which inhibits the catalytic activity of its target procoagulant protease by directly binding that protease with high affinity and specificity. Used as single agents, anticoagulant aptamers effect varying intensities of in vitro and in vivo anticoagulation.

An antidote oligonucleotide (AO), the base sequence of which is complementary to all or part of an aptamer's base sequence, can neutralize an aptamer's anticoagulant effect. Several polyamines, including protamine, can effect nonspecific neutralization of aptamers. (See also U.S. application Ser. No. 12/588,016.)

Anticoagulant aptamers suitable for use in the present invention include, but are not restricted to, aptamers that bind and inhibit FIXa (Rusconi et al, Nature 419:90-94 (2002)) and FXa (Buddai et al, J. Biol. Chem. 285:5212-5223 (2010)), and aptamers that bind prothrombin (factor II, FII) (Layzer and Sullenger, Oligonucleotides 17(1):1-11 (2007); Bompiani and Sullenger, unpublished). The latter aptamer also inhibits the catalytic action of thrombin. Details of certain aptamers, and aptamer combinations, suitable for use in the invention (and antidotes therefore) are provided in the Examples that follow.

FIXa Aptamer

FIXa aptamer designated RNA9.3t is a 35-base RNA oligonucleotide that inhibits the catalytic cleavage of factor X (FX) by FIXa and by the factor VIIIa (FVIIIa)-FIXa complex known as intrinsic factor Xase (FXase). (See U.S. Pat. No. 7,300,922.) FIXa aptamer also binds factor IX (FIX) and inhibits the cleavage of FIX by factor VIIa (FVIIa) but not by factor XIa (FXIa) (Gopinath et al, Thromb. Haemost. 95:767-771 (2006)). A pegylated 31-base modification of 9.3t, the base sequence of which includes multiple 2'-fluoropyrimidines, is manufactured by Regado Biosciences, Inc., Durham, N.C. The pegylated 31-base modification, originally designated RB006 by Regado and since named pegnivacogin, has undergone successful phase 1 trials in human subjects (Dyke et al, Circulation 114:2490-2497 (2006), Chan et al, Circulation 117:2865-2874 (2008), Chan et al, Journal of Thrombosis & Haemostasis 6:789-796 (2008)) and is currently being tested in Phase II trials in patients undergoing percutaneous transluminal coronary angioplasty (PTCA) procedures (Povsic et al, Circulation 122:A13255 (2010)).

An AO for pegnivacogin is a 15-base RNA oligonucleotide the 3' to 5' sequence of which is complementary to the 15-base sequence beginning at the 5' end of pegnivacogin (Dyke et al, Circulation 114:2490-2497 (2006)). That antidote, originally designated RB007 by Regado and since named animaversen, neutralizes the anti-FIXa activity of pegnivacogin.

FXa Aptamer

FXa aptamer designated $RNA_{11F7t}$ is a 37-base RNA oligonucleotide (Buddai et al, J. Biol. Chem. 285:5212-5223 (2010)). The base sequence of that aptamer includes multiple 2'-fluoropyrimidines, and its 3' terminal base is an inverted deoxythymidine. $RNA_{11F7t}$ inhibits thrombin formation catalyzed by prothrombinase, the complex of FXa, factor Va (FVa), and calcium ions assembled on a phospholipid surface, by inhibiting the interaction between FXa and FVa (Buddai et al, J. Biol. Chem. 285:5212-5223 (2010)). $RNA_{11F7t}$ binds FX as well as FXa (Buddai et al, J. Biol. Chem. 285:5212-5223 (2010)). An AO specific for $RNA_{11F7t}$ has been synthesized and tested.

Thrombin Aptamer

Prothrombin aptamer, designated R9D-147T, is a 58-base truncation of an 82-base RNA oligonucleotide RNA9D-14, the sequence of which was published in 2007 (Layzer and Sullenger, Oligonucleotides 17(1):1-11 (2007) (see also PCT/US06/36109)). In addition to inhibiting the catalytic activity of thrombin on fibrinogen, this aptamer also binds prothrombin and inhibits its cleavage by FXa. An AO specific for this aptamer has been synthesized and tested.

FIXa aptamer is a ROA. (Nimjee et al, Molecular Therapy 14:408-415 (2006); Dyke et al, Circulation 114: 2490-2497 (2006); Chan et al, Circulation 117: 2865-2874 (2008); Chan et al, Journal of Thrombosis & Haemostasis 6: 789-796 (2008)). The ability of prothrombin aptamer and FXa aptamer to prolong the prothrombin time, the partial thromboplastin time, and the thromboelastographic lag time of whole blood within minutes following the addition of either of those aptamers strongly suggests that both of those aptamers, like FIXa aptamer, will also be in vivo ROAs.

Lepirudin (Recombinant Hirudin, r-Hirudin, Desulfatohirudin)

The present approach of effecting neutralizable rapid onset anticoagulation, in certain embodiments, involves the administration to a subject of lepirudin, a 65 amino acid polypeptide direct thrombin inhibitor (DTI) having a molecular weight of 6979.5. The amino acid sequence of lepirudin, shown in FIG. 1, resembles that of natural hirudin, the ROA found in leech saliva. Y63 of natural hirudin, but not lepirudin, is sulfated. The 12 amino acid C-terminal sequence binds the fibrinogen binding site of thrombin, exosite I. The N-terminal sequence forms a steric blockade of thrombin's catalytic site by occupying that site. Because it interacts with two thrombin sites, lepirudin has been termed a bivalent DTI. Since the $K_d$ of lepirudin for thrombin is approximately 0.2 picomolar, the binding and inhibition of thrombin are regarded as irreversible. The in vivo half-life of lepirudin is approximately 80 minutes in humans with normal renal function. The drug can remain in the circulation longer than 120 hours in a patient with renal failure.

As shown in FIG. 17, lepirudin alone added to whole blood at a concentration of 6.4 micrograms/mL prolongs the lag phase of a TEG tracing from the normal range to approximately 19 minutes, while the combination of lepirudin and FIXa aptamer added to whole blood at concentrations of 1.6 micrograms/mL and 0.5 micromolar, respectively, prolongs the lag phase to >180 minutes. In other words, a TEG tracing obtained on whole blood anticoagulated with the combination of lepirudin and FIXa aptamer at the aforementioned concentrations resembles a TEG tracing obtained on whole blood anticoagulated with UFH 5 U/mL.

Bivalirudin

Figure 2:
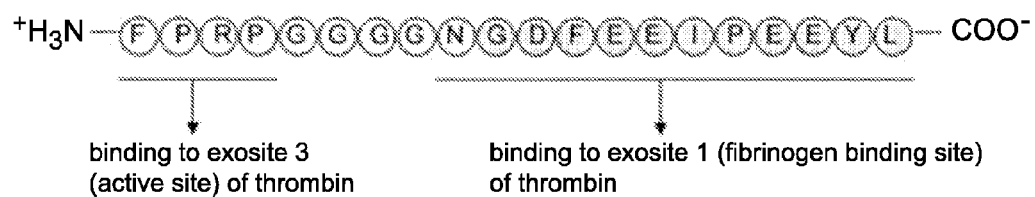
FIG. 2. Amino acid sequence of bivalirudin (SEQ ID NO: 12).

In certain embodiments, the present approach for effecting rapid onset anticoagulation in a subject involves the use of bivalirudin (see FIG. 2), a reversible 20-amino acid peptide bivalent DTI, molecular weight 2180 Daltons, that received FDA approval in 2000. The 12 amino acid C-terminal sequence mimics the corresponding C-terminal sequence of lepirudin and similarly binds the fibrinogen binding site of thrombin. Linked to the C-terminal sequence of bivalirudin via a tetraglycine spacer is the tetrapeptide sequence FPRP, which engages the catalytic site of thrombin. Bivalirudin binds thrombin with $K_d$ of approximately 1.9 nanomolar. It inhibits thrombin until thrombin's cleavage of the terminal R—P bond reduces the affinity of the C-terminal sequence for the fibrinogen site. The combination of proteolytic cleavage and renal excretion of the unchanged peptide results in an in vivo half-life for bivalirudin of about 30 minutes.

Fondaparinux

In certain embodiments, the present approach for effecting rapid onset anticoagulation involves the use of fondaparinux, a linear heavily sulfated polydisaccharide anticoagulant, molecular weight 1728 Daltons, that effects indirect and specific inhibition of FXa. In 2001, the FDA approved the use of subcutaneous fondaparinux for prophylaxis against deep vein thrombosis following several lower extremity orthopedic operations. Because the drug undergoes renal excretion and lacks an approved antidote, it is contraindicated in renal failure patients. A TEG tracing of whole blood anticoagulated with a combination of fondaparinux and FIXa aptamer resembles a TEG tracing of whole blood anticoagulated with UFH.

Figure 3:
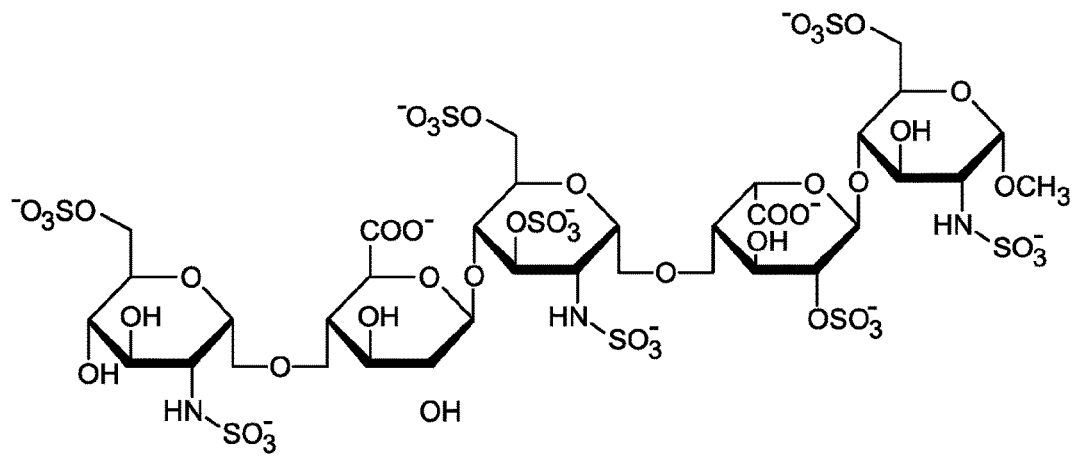
FIG. 3. Structure of fondaparinux.

UFH is a poydisperse mixture of linear heavily sulfated linear polydisaccharide chains (Lindahl, Biosynthesis of heparin and related polysaccharides, In: Lane, Lindahl, eds. Heparin, Boca Raton: CRC Press, pp. 159-189 (1989)) the repeating disaccharide unit of which consists of N-acetylglucosamine and hexuronic acid joined in 1→4 glycosidic linkage. Since the average molecular weight of UFH is 12,000 to 15,000 Daltons, the average UFH chain has 40 to 50 monosaccharide units. Approximately one third of UFH chains contain a pentasaccharide sequence the specific sulfation pattern of which enables it to bind antithrombin (AT) (Nadler, Natural occurrence and possible biological role of heparin, In: Lane and Lindahl, eds. Heparin. Boca Raton: CRC Press, pp. 81-96 (1989)), a constitutive circulating serine protease inhibitor. UFH-AT binding initiates a principal anticoagulation mechanism (Damus et al, Nature 246:

355-357 (1973), Olson et al, J. Biol. Chem. 256:11073-11079 (1981)) by inducing a conformational change in AT that accelerates the inhibition by AT of thrombin and several other procoagulant proteases. Thus, the principal anticoagulation mechanism of UFH is indirect. Chains lacking the catalytic pentasaccharide sequence (CPS), i. e., about two thirds of the UFH chains present in commercial UFH, do not bind AT and do not produce its principal anticoagulation mechanism. The structure of fondaparinux shown in FIG. 3, effectively duplicates the structure of UFH's CPS and produces a conformational change in AT identical to the conformational change in AT produced by CPS-containing UFH chains.

The identical conformational changes produced in AT by UFH and fondaparinux do not produce identical anticoagulant effects. The reason is that the anticoagulant effect of a UFH-AT complex depends not only on the presence of the CPS in the UFH chain, but also on the remaining length of the UFH chain. A UFH-AT complex, in which the UFH chain has a total of 18 or more monosaccharide units, inhibits thrombin, FXa, FIXa, and, to lesser degrees, factor XIa (FXIa), factor XIIa (FXIIa), and factor VIIa (FVIIa). A UFH-AT complex, in which the UFH chain has a total of 17 or fewer monosaccharide units, inhibits only FXa. Since a fondaparinux-AT complex is essentially a UFH-AT complex the chain of which has a total of 5 monosaccharide units, fondaparinux-AT complexes inhibit only FXa.

In 2009, investigators at Portola Pharmaceuticals, Inc. synthesized an antidote that can neutralize the anticoagulant effect of several FXa inhibitors, including fondaparinux and small molecule FXa inhibitors (see below). That antidote is a mutant FXa polypeptide, the structure and amino acid sequence of which are similar to those of FXa, except that the γ-carboxyglutamic acid (Gla) domain is absent and the catalytic site serine is replaced by alanine. That Gla-less S→A mutant, currently designated PRT064445, possesses no pro- or anticoagulant activity. The antidote effects of PRT064445 have been published in abstract form (Abstract OC-TH-107, "Reconstructed recombinant factor Xa as an antidote to reverse anticoagulation by factor Xa inhibitors" by G Lu, P Luan, S J Hollenbach, K Abe, F R DeGuzman, G Siu, A Hutchaleelaha, M Inagaki, P B Conley, D R Phillips, and U Sinha. Abstracts from XXII International Society of Thrombosis and Haemostasis Congress, Journal of Thrombosis and Haemostasis, Volume 7, Supplement 2, Jul. 11-16, 2009, page 309).

More recently, Bianchini et al developed a mutant antithrombin that can neutralize both fondaparinux and other heparin derivatives (Bianchini et al, Blood DOI 101182/blood-2010-06-288522 2010; Prepublished on-line:1-29). In that mutant antithrombin, a P insertion between R393 and S394 of the non-mutant peptide prevents protease cleavage of the mutant's reactive center loop by FXa, and an N135G mutation increases the binding affinity of the mutant for fondaparinux. PolyMedix investigators also have synthesized a fondaparinux neutralizing agent.

Small Molecule FXa Inhibitors

In certain embodiments, the methodology of the present invention involves the use of "small molecule" FXa inhibitors. As used herein, the term "small molecule" refers to a non-natural non-polymer organic molecule having a molecular weight of less than 800 Daltons. Direct binding of the small molecule to a biopolymer, such as a protein, nucleic acid, or polysaccharide, alters the function of that biopolymer.

Small molecule specific FXa inhibitors that are currently under investigation include otamixaban, apixaban, rivaroxaban, betrixaban, and edoxaban. Each of those agents inhibits FXa-induced cleavage of prothrombin by directly, but non-covalently, binding the catalytic site of FXa with a $K_d$ in the low- or sub-nanomolar range.

Otamixaban (Sabatine et al, Lancet 374:787-795 (2009)) is formulated and intended for IV administration. Rivaroxaban has received approval in Canada and in Europe for prophylaxis against venous thromboembolism in patients who have undergone knee or hip joint replacement operations.

Figure 4:
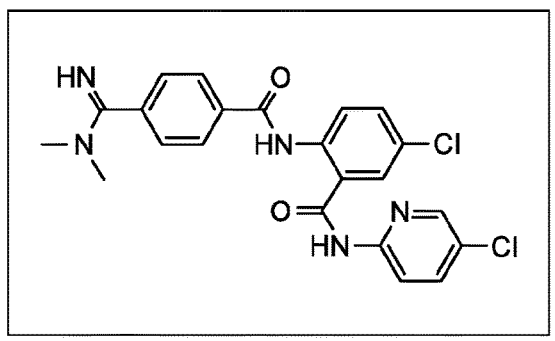
FIG. 4. Structure of PRT 54004.
Figure 5:
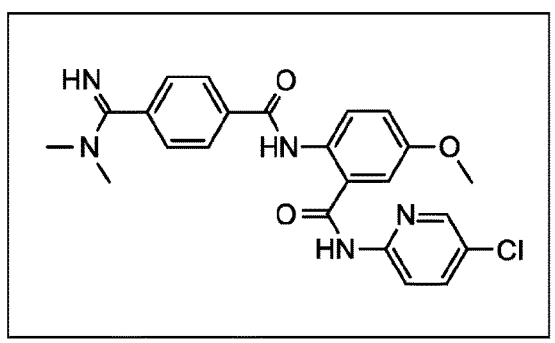
FIG. 5. Structure of betrixaban.

TEG experiments have shown that PRT 54004, molecular weight 447 Daltons, a small molecule FXa inhibitor that binds FXa with a $K_d$ lower than that of betrixaban, can serve as one component of an effective rapid anticoagulation strategy. PRT 54004 and betrixaban, molecular weight 452 Daltons, share similar structures (see FIGS. 4 and 5), as well as similar FXa binding and inhibitory capability. A TEG tracing of whole blood anticoagulated with FIXa aptamer plus PRT 54004 resembles a TEG tracing of whole blood anticoagulated with UFH. While potential ion channel toxicity may preclude further development of PRT 54004 as a human anticoagulant, the ability of solubilized PRT 54004 plus FIXa aptamer to achieve UFH-like anticoagulation in TEG experiments strongly suggests that solubilized preparations of most small molecule FXa inhibitors having a $K_d$ for FXa binding that is appropriately low would also function in similar synergy with FIXa aptamer.

The FXa inhibitory component of an anticoagulation strategy, effected by either a small molecule inhibitor or by fondaparinux, can be expected to be neutralizable.

Bivalent Aptamers

In certain embodiments, the reversible anticoagulant methodology of the invention comprises administering a bivalent aptamer.

Preferred embodiments of the present invention include the use of the following combinations:

(1) a selective factor IXa (FIXa) inhibitor plus a selective factor Xa (FXa) inhibitor, both of which have a $K_d$ for their target molecule of, advantageously, <10 nanomolar, wherein one or both is neutralizable;

(2) a selective FIXa inhibitor plus a selective thrombin (factor IIa, FIIa) inhibitor, both of which have a $K_d$ for their target molecule of, advantageously, <10 nanomolar, wherein one or both is neutralizable;

(3) a selective FXa inhibitor plus a selective thrombin inhibitor, both of which have a $K_d$ for their target molecule of, advantageously, <10 nanomolar, wherein one or both is neutralizable;

(4) a bivalent aptamer the structure of which incorporates FIXa aptamer and FXa aptamer, FIXa aptamer and thrombin aptamer, or FXa aptamer and thrombin aptamer moieties, each of which have a $K_d$ for their target molecule of, advantageously, <10 nanomolar.

Figure 27A:
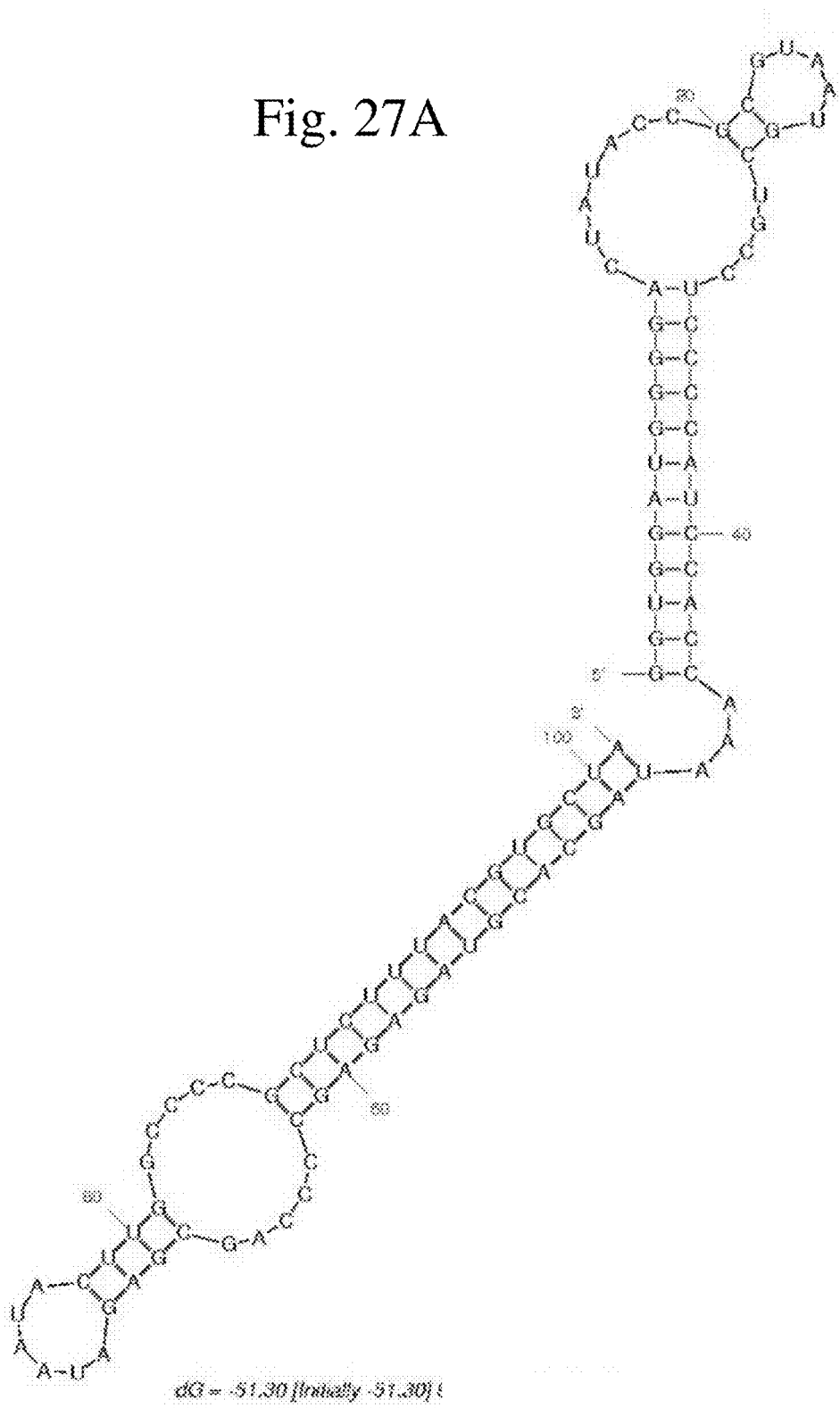
FIGS. 27A-27G: Predicted Structures of FIX/FX and FX/FII dogbone aptamers.
Figure 27B:
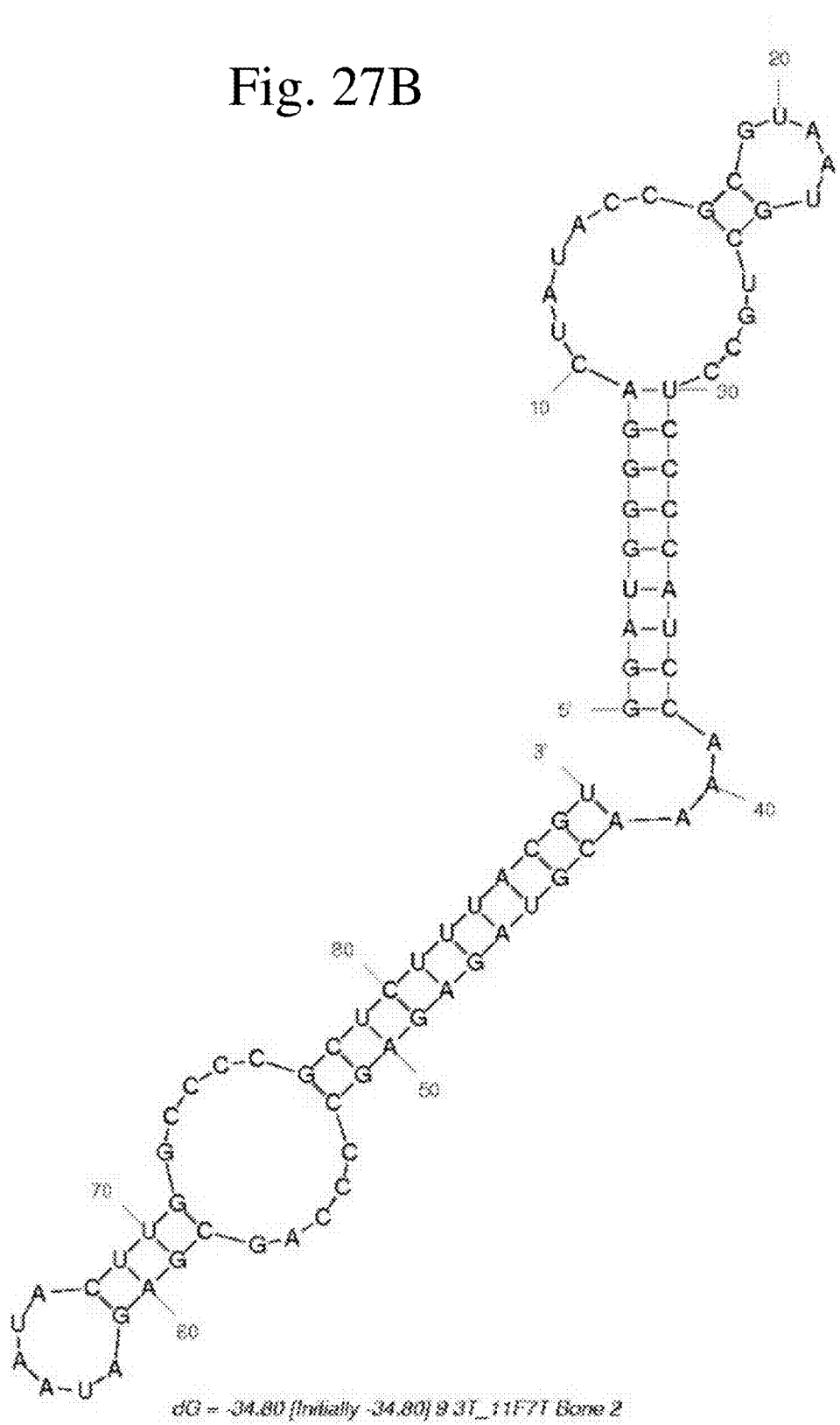
Figure 27C:
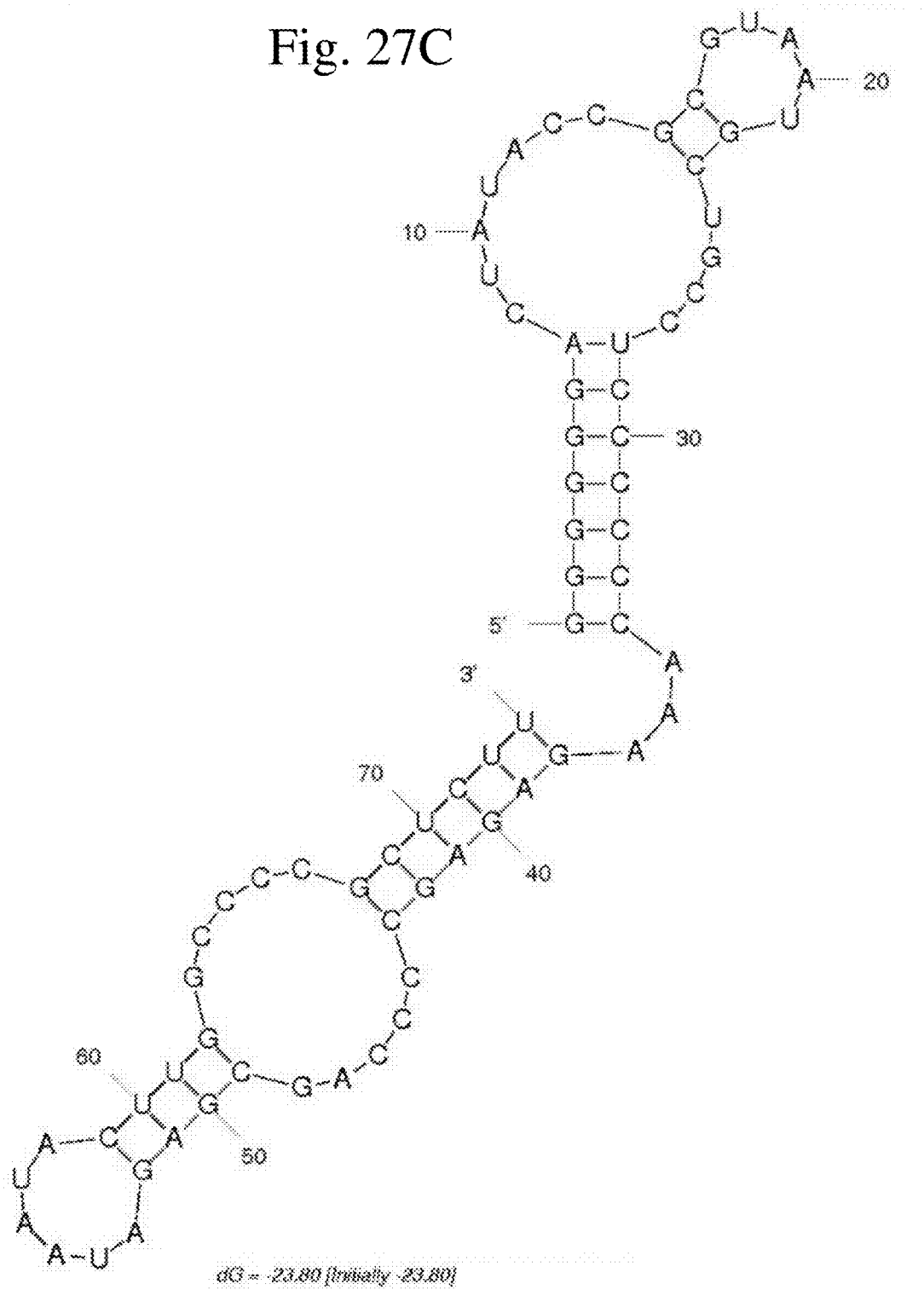
Figure 27D:
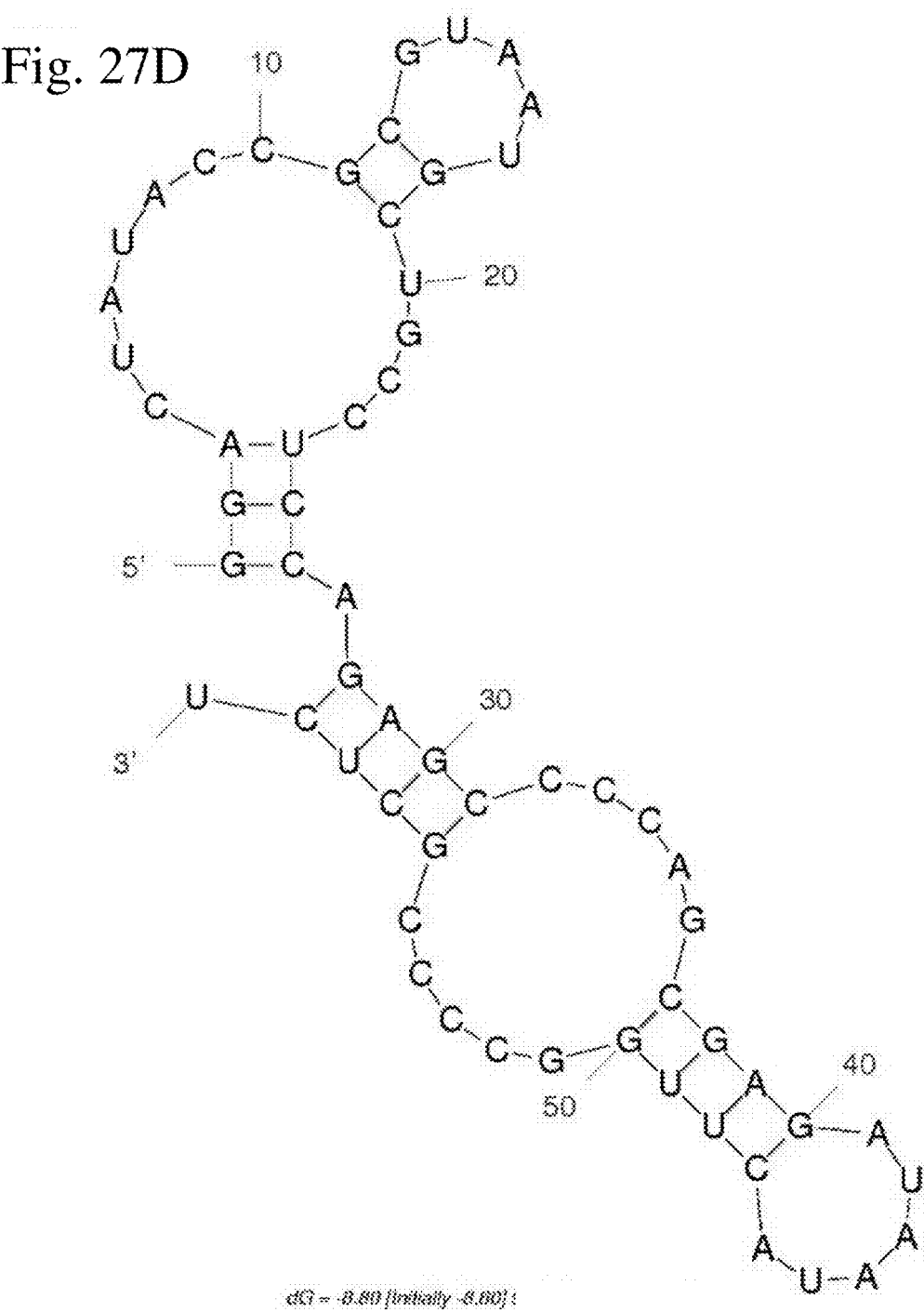
Figure 27E:
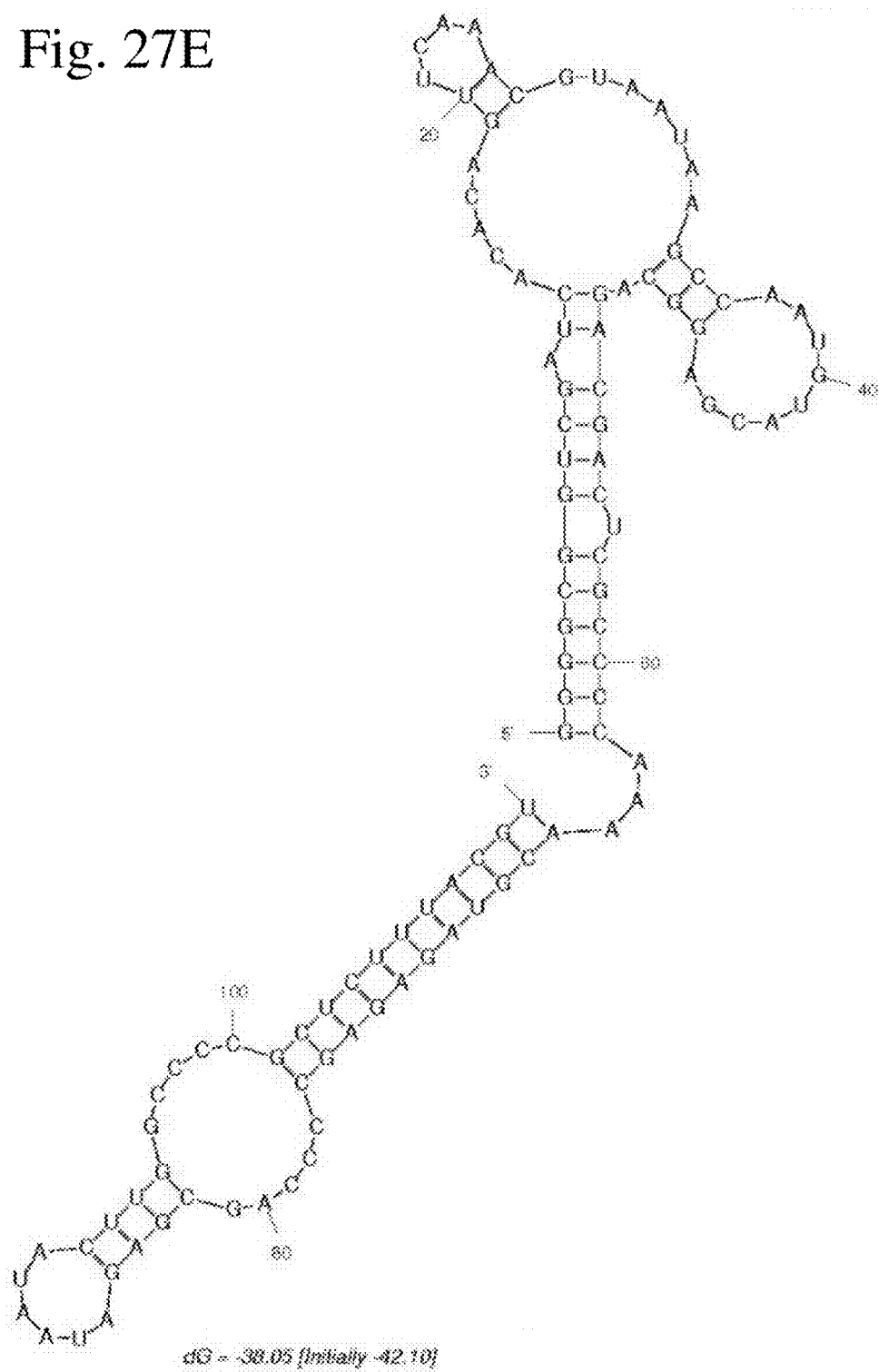
Figure 27F:
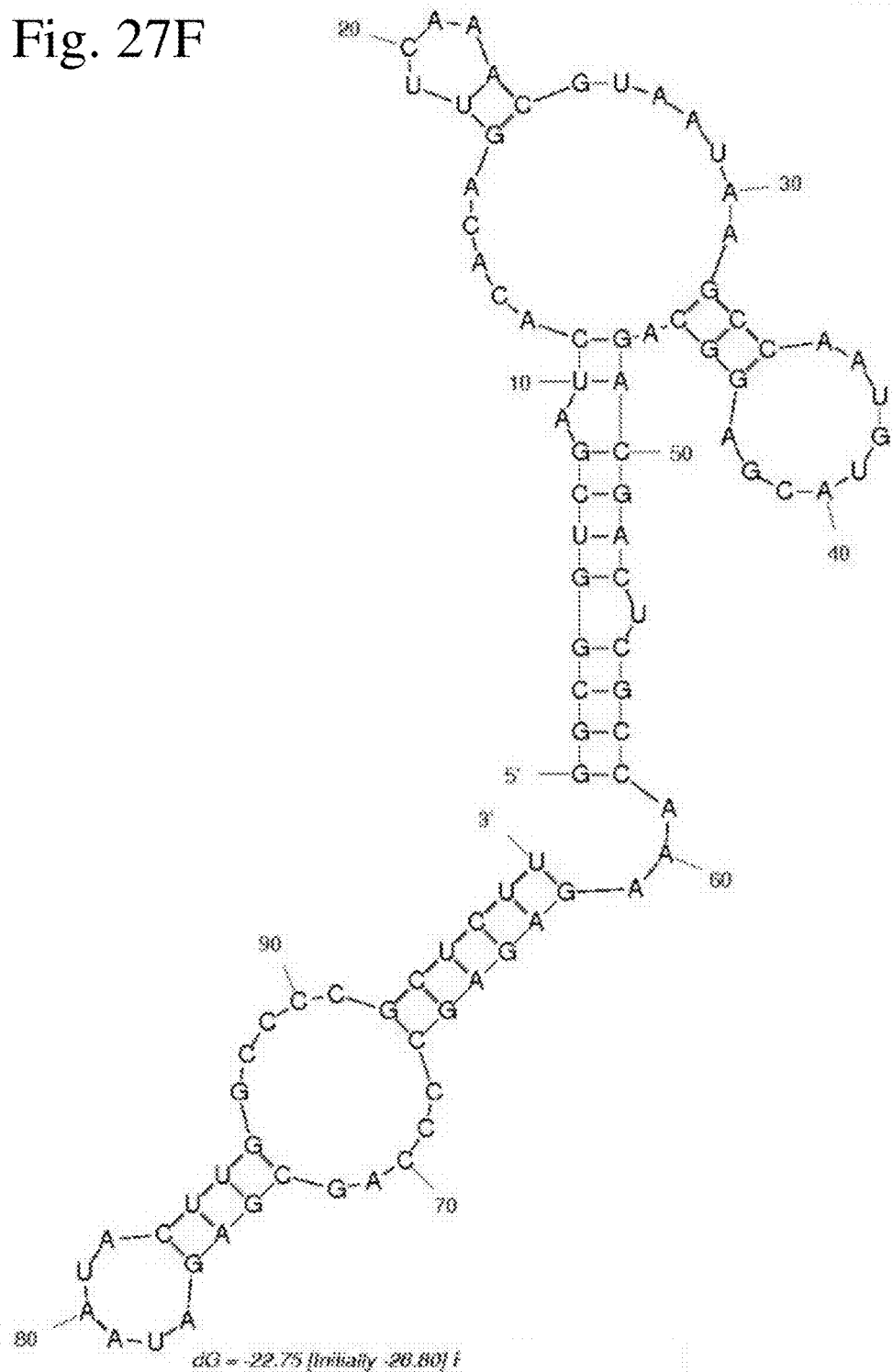
Figure 27G:
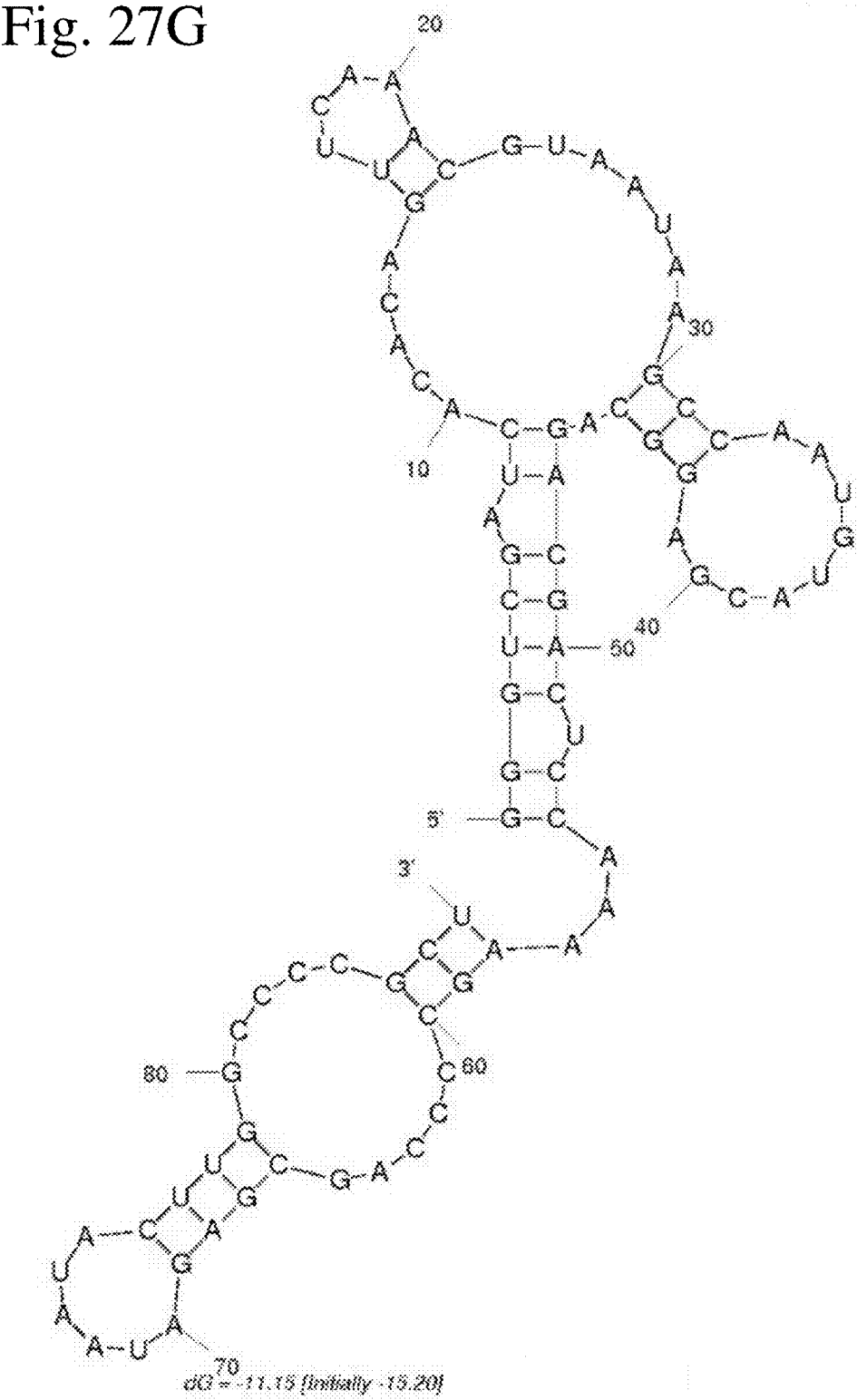

The invention includes, but is not limited to, the use of the following specific pairs of anticoagulant molecules in effecting neutralizable rapid onset anticoagulation in a subject (e.g., a human or non-human mammal):

1. FIXa aptamer plus FXa aptamer
2. FIXa aptamer plus fondaparinux
3. FIXa aptamer plus a small molecule FXa inhibitor (e. g., otamixaban, rivaroxaban, betrixaban, apixaban, or edoxaban)
4. FIXa aptamer plus thrombin (factor IIa, FIIa) aptamer
5. FIXa aptamer plus lepirudin
6. FIXa aptamer plus bivalirudin
7. FXa aptamer plus thrombin aptamer
8. FXa aptamer plus lepirudin 9. FXa aptamer plus bivalirudin
10. Fondaparinux plus thrombin aptamer
11. Fondaparinux plus bivalirudin
12. Fondaparinux plus lepirudin
13. Small molecule FXa inhibitor plus thrombin aptamer
14. Small molecule FXa inhibitor plus lepirudin
15. Small molecule FXa inhibitor plus bivalirudin The invention also includes use of dual action aptamers (such as those below), in which the aptamer moieties can be bound either directly to each other (see, for example, FIG. 27D) or indirectly via a "linker", e.g., a polymer linker, such as polyethylene glycol (PEG) or a polypurine such as polyadenosine (polyA):

FIXa aptamer-FXa aptamer or FIXa aptamer-linker-FXa aptamer

FIXa aptamer-FIIa aptamer or FIXa aptamer-linker-FIIa aptamer

FXa aptamer-FIIa aptamer or FXa aptamer-linker-FIIa aptamer

In whole blood subjected to a TEG assay, embodiments of the present invention can effect anticoagulation intense enough to reduce the "α" angle, a TEG variable that reflects the rate of clot formation, and the "maximum amplitude" (MA), a TEG variable that reflects the magnitude of clot strength, to ranges similar to the ranges to which UFH reduces those TEG variables. (See Example I.) Inhibition of each member of the targeted pair of procoagulant proteases can be accomplished by the concomitant use of 2 different inhibitor molecules, each of which specifically inhibits a different member of the pair, or by the use of 1 inhibitor molecule that specifically inhibits both members of the pair. A TEG assay obtained on whole blood anticoagulated with embodiments of the invention, in which the effective concentration of each procoagulant protease inhibitor is less than 6.0 micromolar, resembles a TEG assay obtained on whole blood anticoagulated with UFH 5 U/mL. In a preferred embodiment, anticoagulant effects are achieved using two aptamers or one bivalent aptamer, as described above, that are/is neutralizable by administering either aptamer-specific antidote oligonucleotides or certain nucleic acid binding polymers, such as cyclodextrin-containing polycation (CDP) or protamine (Oney, Nature Medicine 15:1224-1228 (2009); see also U.S. application Ser. No. 12/588,016).

The rapid onset anticoagulants of the invention, and antidotes therefore, can be formulated into pharmaceutical compositions that can include, in addition to the anticoagulant or antidote, a pharmaceutically acceptable carrier, diluent or excipient. The precise nature of the composition will depend, at least in part, on the nature of the anticoagulant or antidote and the route of administration. Optimum dosing regimens can be readily established by one skilled in the art and can vary with the anticoagulant or antidote, the patient and the effect sought. (Data from experimental animal (Nimjee et al, Molecular Therapy 14:408-415 (2006)) and human (Dyke et al, Circulation 114: 2490-2497 (2006); Chan et al, Circulation 117: 2865-2874 (2008)) studies suggest that the complete in vivo reversal of FIXa aptamer's anticoagulant effect requires the IV administration of a 2-10-fold molar excess of its antidote oligonucleotide. In certain situations, partial reversal of the anticoagulant effect may be preferred.)

Generally, the anticoagulant and antidote is administered IV (e.g., via IV infusion), IM, IP, SC, orally or topically, as appropriate.

The method of the present invention finds application in a number of clinical settings. The instant approach can be used, for example, as a primary therapy to prevent thrombosis or to prevent further thrombosis, for example, in acute coronary syndromes, in cases of proven or suspected pulmonary thromboembolism, or in cases of proven or suspected arterial or deep vein thrombosis. The instant approach can also be used as an adjunct therapy to prevent procedure-induced thrombosis, for example, in patients undergoing cardiac catheterization and coronary angiography, percutaneous transluminal coronary angioplasty (PTCA) or percutaneous coronary intervention (PCI), percutaneous intracardiac catheter-based procedures (e.g., ablation of an arrhythmogenic focus, "clam shell" closure of an atrial septal defect, or catheter-facilitated valve implantation), peripheral arterial angioplasty and stent implantation, open vascular operations, endovascular graft implantation operations, solid organ (e. g., liver, kidney, pancreas) transplantation operations, hemodialysis, extracorporeal membrane oxygenation (ECMO) or cardiopulmonary bypass (CPB).

The approach described herein retains the advantages UFH (e.g., in CPB), which advantages include: immediate anticoagulation measurable by a point-of-care clot-based assay, a plasma half-life long enough to obviate the need for continuous infusion, neutralizability, and the ability to reproduce anticoagulation following neutralization, if necessary. The approach described herein avoids the disadvantages of UFH, for example, the components used in accordance with the invention circulate without inducing platelet activation, attenuate the generation of thrombin and FXa, and undergo neutralization without activating complement or causing any other pro-inflammatory sequel.

Most patients who require rapid onset anticoagulation do not require CPB and should not be exposed to the intensity of anticoagulation required to perform CPB. However, the rapid onset anticoagulation strategy of the invention may, at lower concentrations of its component anticoagulant(s), provide safe and effective non-CPB anticoagulation. The instant strategy may, for example, help to suppress thrombin generation in patients with acute coronary syndromes (Merlini et al, Arterio. Throm. Vasc. Biol. 17:1325-1330 (1997)) and the systemic inflammatory response in patients undergoing coronary angioplasty (Azar et al, Am. J. Cariol 80:1476-1478 (1997)). In addition, although neutralizability is mandatory for a standard CPB anticoagulation strategy, neutralizability increases the safety of administering any anticoagulation strategy for any indication. Thus, the present invention provides potential advantages for many indications for rapid onset anticoagulation besides CPB anticoagulation.

Figure 6:
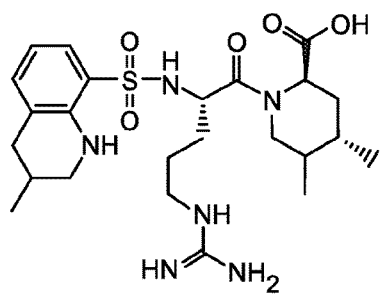
FIG. 6. Molecular structure of argatroban.

In addition to UFH, lepirudin, and bivalirudin, the FDA has approved one other ROA, argatroban, molecular weight 509 Daltons, a small molecule monovalent DTI having a Kd for thrombin of approximately 40 nanomolar. Argatroban, the structure of which is shown in FIG. 6, inhibits thrombin by reversibly binding to the catalytic site of thrombin. The present invention differs from currently approved ROA in at least the following ways.

First, the invention includes either (1) the concomitant use of two procoagulant protease inhibitors, each of which effects the specific inhibition of FIXa, FXa, or thrombin; or (2) the use of a dual action aptamer the structure of which incorporates aptamer moieties that inhibit FIXa and FXa, FIXa and FIIa, or FXa and FIIa. In contrast, UFH effects rapid onset anticoagulation through the indirect inhibition of multiple procoagulant proteases. Each DTI approved for IV use effects rapid onset anticoagulation through the direct and specific inhibition of thrombin. Otamixaban, the only IV FXa inhibitor currently under clinical investigation, effects rapid onset anticoagulation through the direct and specific inhibition of FXa.

Secondly, each pair of procoagulant protease inhibitors described above includes at least one neutralizable inhibitor. Advantageously, the pairs include two neutralizable protease inhibitors. In contrast, except for UFH, none of the currently approved ROAs is neutralizable.

Thirdly, several embodiments of the invention achieve anticoagulation without the specific inhibition of thrombin. In contrast, the currently approved ROAs either indirectly inhibit thrombin plus several other procoagulant proteases, or directly inhibits thrombin alone.

Figure 7:
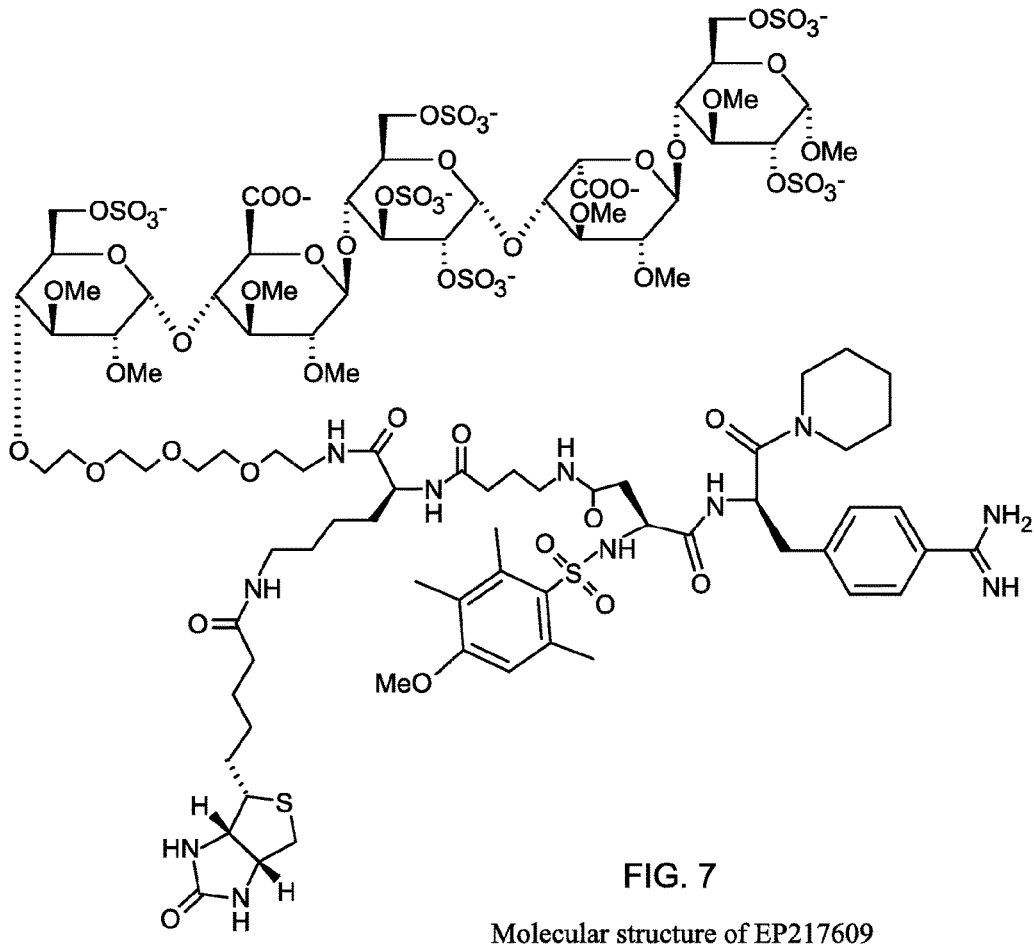
FIG. 7. Molecular structure of EP217609.
Figure 8:
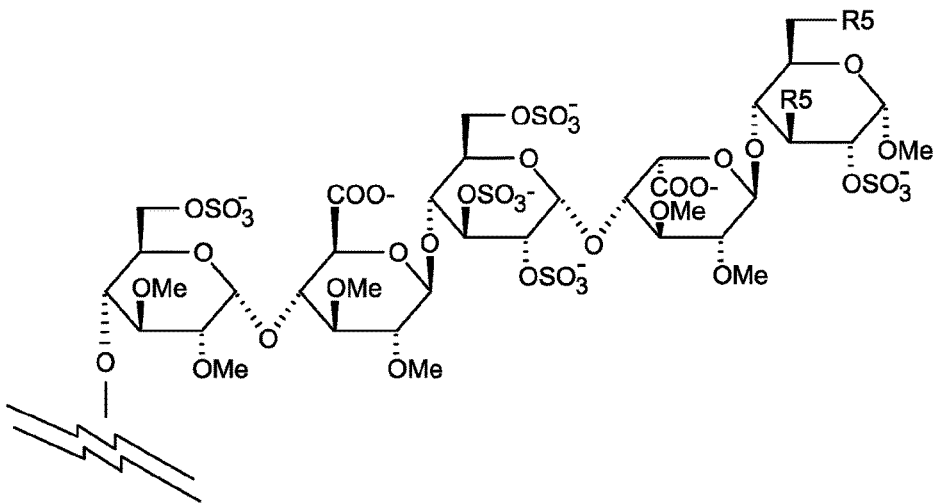
FIG. 8. Structure of a pentasaccharide anticoagulant moiety of EP217609. R5 on C3 is OMe and R5 on C6 is $OSO_3^-$.
Figure 9:
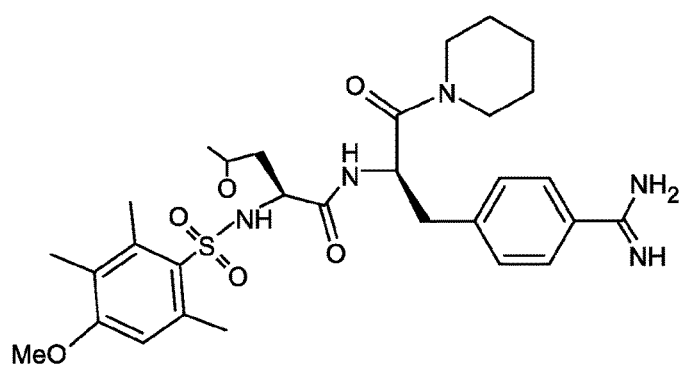
FIG. 9. DTI residue of EP217609.
Figure 10:
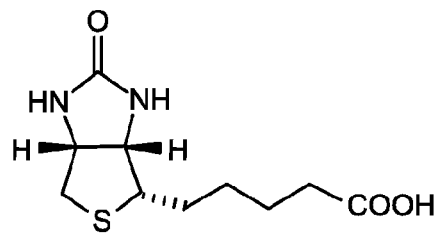
FIG. 10. Molecular structure of biotin.

The present invention also differs from the investigational dual action parenteral ROA, EP217609, molecular weight 2910, the structural formula of which is shown in FIG. 7 (see WO2006067173). In 2010, an early in-human evaluation of that ROA was reported (Gueret et al, Twenty-first International Congress on Thrombosis 2010, Poster 177, November 2010). EP217609 has two anticoagulant moieties that are covalently linked to each other by non-anticoagulant spacers through a lysine residue. A peptide bond covalently links the carboxy terminal of a biotin residue to the ϵ-amino group of the lysine residue. One of the anticoagulant moieties (see FIG. 8) is a pentasaccharide residue the structure and anticoagulation mechanism of which mimic those of the investigational anticoagulant pentasaccharide idraparinux (Harenberg, Thromb. Haemost. 102:811-815 (2009)). FIG. 9 shows the structure of the other anticoagulant moiety, a residue of the DTI molecule designated compound (12) by de Kort et al (Drug Discovery Today 10:769-779 (2005)). Compound (12) is a derivative of β-naphthylsulfonylglycyl-D,L-4-amidino-phenylanlylpiperidide (NAPAP), a DTI first synthesized in the early 1980s. The structure of biotin, a water soluble B complex vitamin, is shown in FIG. 10. It will be appreciated that the structure of EP217609 differs from the structure of the anticoagulant components of the present invention.

Certain aspects of the invention can be described in greater detail in the non-limiting Examples that follows. (See also Hirsh et al, Chest 126:188S-203S (2004), Hobbhahn et al, J Appl Physiol 71:1415-21 (1991), Edmunds and Colman, The Annals of Thoracic Surgery 82:2315-22 (2006), Edmunds, Jr, Ann Thorac Surg 66:S12-6 (1998); discussion S25-8, Levi et al, Circulation 109:2698-704 (2004), Esmon, Br J Haematol 131:417-30 (2005), Reilly aand Bulkley, Crit Care Med 21:S55-68 (1993), Koster et al, Journal of Thoracic & Cardiovascular Surgery 126:906-7 (2003), Hayashi et al, Asaio J 46:334-7 (2000), Cremer et alm Ann Thorac Surg 61:1714-20 (1996), Drouet et al, American Heart Journal 158:177-84 (2009), Nimjee et al, Mol Ther 14:408-15 (2006), Zelenkofske et al, Circulation 2010; 122:A14661 (2010), Rusconi et al, Circulation 122: A12822 (2010).)

Example I

As described in greater detail below, TEG experiments can be used to identify preferred pairs of anticoagulants suitable for use in the invention and optimum concentrations of each anticoagulant (e.g., which pairs/concentrations effect anticoagulation as intense as UFH-induced anticoagulation in whole blood). The anticoagulant efficacy of the preferred pairs of anticoagulants identified by TEG can then be tested in blood that is circulated continuously for 2 hours in an isolated 25-mL oxygenator circuit. The more preferred anticoagulants can then be tested for their ability to provide satisfactory anticoagulation during CPB with circulatory arrest in a large animal. CPB is a form of extracorporeal circulation without which many cardiac operations that have become standard treatments for many congenital and acquired cardiac defects could not be performed.

TEG Assessment of Anticoagulation Strategies

TEG is a waveform generated from serial measurements of the torque transmitted from a small oscillating cup to the tip of a metal pin inserted into the cup by a 360 microliter sample of blood or plasma added to the cup.

Figure 11:
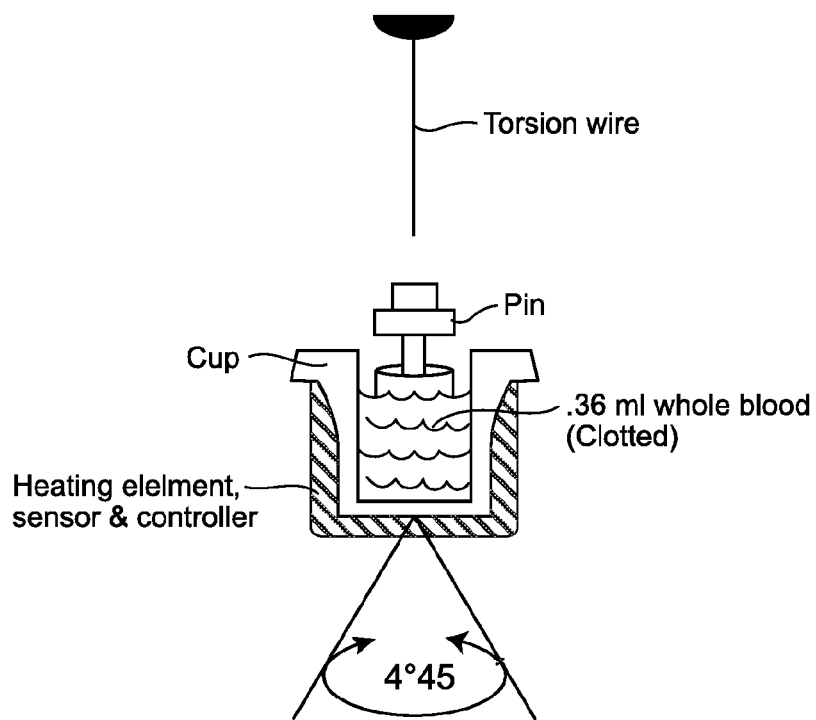
FIG. 11. Mechanical components of a TEG analyzer (TEG 5000 User Manual, pp 3-4, 1999-2007).

Several mechanical components of a TEG analyzer are shown in FIG. 11. A 360 microliter blood sample has been added to the cup. For 180 minutes after the sample is added, the cup oscillates alternatively clockwise and counterclockwise through an arc of 4° 45' at a frequency of one oscillation cycle—i. e., one clockwise rotation and one counterclockwise rotation—every 10 seconds. The lower end of the pin is immersed by the sample; the upper end is suspended from a torsion wire. The TEG analyzer records a single measurement of rotation-induced torque after each clockwise rotation and after each counterclockwise rotation of the cup. "The torque of the rotating cup is transmitted to the immersed pin only after fibrin-platelet bonding has linked the cup and [the] pin together. The strength of these fibrin-platelet bonds affects the magnitude of the pin motion, such that strong clots move the pin directly in phase with the cup motion. Thus, the magnitude of the output is directly related to the strength of the formed clot . . . . [If] the clot retracts or lyses, these bonds are broken and the transfer of cup motion is diminished. The rotation movement of the pin is converted by a mechanical-electrical transducer to an electrical signal which can be monitored by a computer" (TEG 5000 User Manual, pp 3-4, 1999-2007)). The computer converts the series of electrical signals into the TEG tracing.

Figure 12:
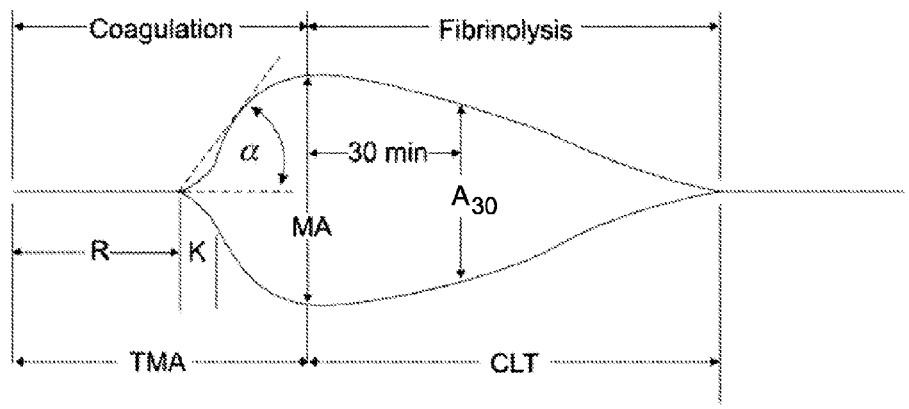
FIG. 12. TEG tracing (TEG 5000 User Manual, pp 3-4, 1999-2007).

FIG. 12 provides a diagram of a TEG tracing that has been drawn to illustrate several variables that the computer of a TEG analyzer can display. The vertical axis displays "amplitude" in millimeters; the horizontal axis displays time in minutes. The initial "rotation movement of the pin" (TEG 5000 User Manual, pp 3-4, 1999-2007) is always zero, because blood transmits no torque from the cup's rotation to the pin before clot formation begins. Hence, the initial portion of a TEG tracing is a horizontal line, "R", whose zero amplitude indicates zero initial transmission of rotation-induced torque. When clot formation begins, the TEG tracing bifurcates, indicating the onset of torque transmission. "Amplitude", defined as the vertical distance between the evolving upper and lower segments of the bifurcated tracing, is directly proportional to the torque transmitted from the cup to the pin as the cup alternately rotates through clockwise and counterclockwise arcs. The stronger the clot, the greater will be the MA (the maximum amplitude, or distance between the upper and lower segments of the tracing), and vice versa. The more stable the clot, the longer the upper and lower segments will remain widely separated. Other abbreviations that appear in FIG. 12 are:

R (reaction time): "the period of time of latency from the time that the blood was placed in the . . . analyzer until the initial fibrin formation."

K (kinetics): the time between the time the bifurcation occurs and the time the amplitude reaches 20 mm. K is undefined for a TEG whose amplitude does not reach 20 mm.

α (angle): the angle formed between the initial horizontal portion of the TEG tracing and a line that originates from the bifurcation site and is tangential to the upper segment of TEG tracing at the point at which that segment's second derivative with respect to time is zero.

TMA (time to MA): the time from the initiation of coagulation to the time MA occurs.

CLT (clot lysis time): the time from the time at which MA is reached until the time at which the clot has undergone complete lysis, i. e., the time at which the clot is no longer able to transfer torque from the rotating cup to the pin.

$A_{30}$ (amplitude at 30 minutes): the amplitude 30 minutes after MA occurs.

In its User Manual, the manufacturer of the TEG analyzer, Haemoscope Corporation, Niles, Ill., states: "The resulting hemostasis profile [indicated by the TEG tracing] is a measure of the time it takes for the first fibrin strand to be formed, the kinetics of clot formation, the strength of the clot . . . and dissolution of clot (TEG 5000 User Manual, pp 3-4, 1999-2007))." (FIG. 7) The User Manual adds: R represents the "enzymatic portion of coagulation". K "is a measure of the speed to reach a certain level of clot strength . . . [and] represents clot kinetics". The angle α "measures the rapidity of fibrin build-up and cross-linking (clot-strengthening). This represents fibrinogen level. MA " . . . represents the ultimate strength of the fibrin clot" (TEG 5000 User Manual, pp 3-4, 1999-2007).

Figure 13:
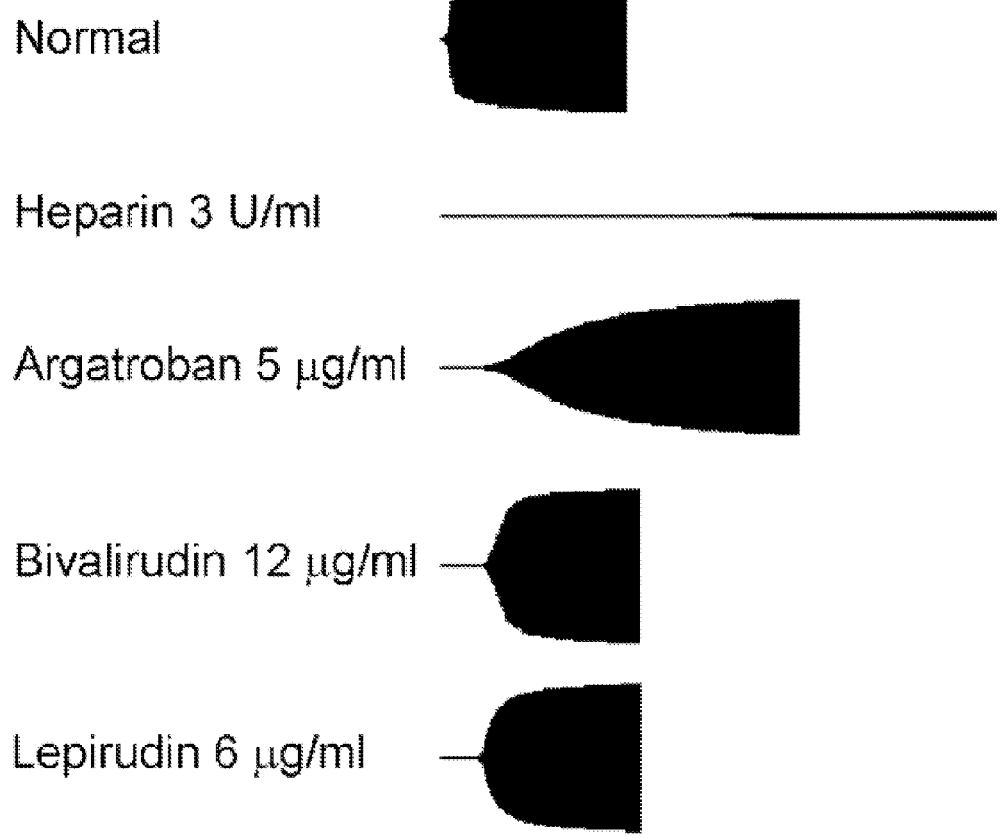
FIG. 13. TEG tracings (Nielsen et al, J. Heart Lung Transplant. 25:653-663 (2006)).

Nielsen et al (J. Heart Lung Transplant. 25:653-663 (2006)) performed TEG tracings on normal plasma and on plasma containing UFH (heparin), argatroban, bivalirudin, or lepirudin at the concentrations indicated. The DTI concentrations studied are the concentrations recommended for CPB anticoagulation if UFH cannot be used. The nanomolar concentrations of argatroban, bivalirudin, and lepirudin corresponding to the microgram per mL concentrations listed are, respectively, 9500, 5500, and 860 nanomolar. In contrast to the TEG diagram in FIG. 12 and the TEG tracings in FIGS. 14 through 17, the area between the upper and lower segments of each TEG tracing in FIG. 13 is filled instead of open.

Nielsen et al (J. Heart Lung Transplant. 25:653-663 (2006)) demonstrated the usefulness of TEG to compare the efficacies of different anticoagulation strategies in plasma. They obtained TEG tracings, shown in FIG. 13, on a non-anticoagulated plasma sample (normal) and on 4 other plasma samples, each of which was anticoagulated with one of the approved ROAs at concentrations recommended for CPB. Coagulation was activated in each sample by the addition of tissue factor (TF)/kaolin. UFH and each DTI prolonged R. However, while UFH reduced a angle and MA enough to eliminate the bifurcation, none of the DTIs did so.

From those TEG tracings and from their calculations of maximum rate of thrombin generation and total thrombus generation, Nielsen et al determined that UFH, but not the DTIs at concentrations recommended for CPB, significantly reduced clot propagation and strength (Nielsen et al, J. Heart Lung Transplant. 25:653-663 (2006)). Nielsen et al proposed "that if an anticoagulant regimen results in prolongation of clot initiation and suppression of propagation and strength to an extent similar clinically to heparin-activated antithrombin, then the regimen is likely 'safe' for the conduct of CPB." They also cautioned that "Our data indicate that DTIs as the only method of anticoagulation should not be considered safe for the conduct of CPB" (Nielsen et al, J. Heart Lung Transplant. 25:653-663 (2006)).

Nielsen et al found that a lepirudin concentration of 10 micrograms/mL, approximately 1.4 micromolar, would significantly reduce clot propagation and strength to an extent similar to that seen with UFH-activated AT. In contrast, a concentration of either bivalirudin or argatroban that was ten-fold higher than the concentration recommended for CPB did not significantly reduce clot propagation and strength. Lepirudin may achieve more intense anticoagulation than either of the other two DTIs because lepirudin's $K_d$ for thrombin is approximately 5 orders of magnitude lower than the $K_d$ of either of the other two DTIs. However, as Nielsen et al pointed out, " . . . because of a circulating half-life of 80 minutes, supratherapeutic lepirudin concentrations could cause prolonged, uncontrollable, life-threatening bleeding after CPB" (Nielsen et al, J. Heart Lung Transplant. 25:653-663 (2006)).

FIG. 14 shows the effect on TEG of adding (FIG. 14A) no anticoagulant, i. e., buffer alone, (FIG. 14B) 0.5 micromolar factor VIIa (FVIIa) aptamer, (FIG. 14C) 1.0 micromolar FIXa aptamer, or (FIG. 14D) 1.0 micromolar FXa aptamer to whole blood in which coagulation was triggered by tissue factor (TF). That none of those aptamers prevented clot formation is indicated by the fact that none prevented development of a bifurcated TEG tracing. FXa aptamer (FIG. 14 [D]) prolonged R, lag time, from 4.4 minutes to 17.8 minutes, reduced MA from 69.7 mm to 59.5 mm, and reduced a from about 55 degrees to 24 degrees. However, FXa aptamer did not prevent the ultimate development of clot.

FIG. 15 shows the effect on TEG of adding (FIG. 15A) no anticoagulant, i. e., buffer alone, (FIG. 15B) 2.0 micromolar FIXa aptamer, (FIG. 15C) 2.0 micromolar FXa aptamer, or (FIG. 15D) 5.0 micromolar prothrombin aptamer to 360 microliters of whole blood in which coagulation was triggered by the addition of kaolin instead of TF. In the absence of an anticoagulant (A), R was 6.8 minutes, α was 44.9 degrees, and MA was 63.1 mm. In the presence of FIXa, FXa, and prothrombin aptamers (FIGS. 15B-15D, respectively), R increased to 29.2, 22.5, and 31.3 minutes respectively; α fell to 36.6, 29.8, and 18.6 degrees, respectively; and MA fell to 58.6, 48.4, and 42.5 mm, respectively. Thus, each aptamer, to varying degrees, prolonged the time to clot formation, reduced the rate of clot strengthening, and reduced the ultimate strength of the clot. However, as was true in the previous experiment, no aptamer acting alone at the concentrations tested prevented clot formation.

FIG. 16 shows the effect on TEG of adding (FIG. 16A) no anticoagulant, i. e., buffer alone, (FIG. 16B) FIXa aptamer and FXa aptamer, (FIG. 16C) FIXa aptamer and prothrombin aptamer, (FIG. 16D) FXa aptamer and thrombin aptamer, and (FIG. 16E) UFH to 360 microliters of whole blood in which coagulation was triggered by the addition of kaolin. The expected TEG pattern produced by normal whole blood (A) indicates normal coagulation. The TEG patterns produced in normal blood anticoagulated with pairs of aptamers, (FIG. 16B), (FIG. 16C), and (FIG. 16D) at the concentrations indicated, indicate the absence of coagulation during the 180 minutes the tracings were recorded. No bifurcation appears in any of those tracings. For comparison, a TEG tracing (FIG. 16E) was also obtained on blood anticoagulated with UFH at a concentration near that recommended for CPB anticoagulation. A comparison of TEG tracings shown in FIG. 16B, FIG. 16C, and FIG. 16 D with the TEG tracing in FIG. 16E reveals that the aptamer combinations at the indicated concentrations achieve UFH-like anticoagulation in normal whole blood.

FIG. 17 shows that TEG assays performed in the presence of an aptamer inhibitor of FIXa and a non-aptamer inhibitor of thrombin can also induce UFH-like anticoagulation. The bifurcations in the TEG tracings shown in FIG. 17A and FIG. 17B indicate that clot formation occurred in blood containing FIXa aptamer 0.5 micromolar at 22.1 minutes and in blood containing lepirudin 6.4 micrograms/mL (0.860 micromolar) at 18.7 minutes after coagulation was triggered with kaolin. Thus, FIXa aptamer and lepirudin, when given alone at the concentrations indicated, delayed but did not prevent coagulation. In contrast, the absence of a bifurcation in the TEG tracing shown in FIG. 17C shows that the same concentration of FIXa aptamer plus an even lower concentration of lepirudin, 1.6 micrograms/mL (0.215 micromolar), can prevent clot formation for 180 minutes. Those results indicate that FIXa aptamer and lepirudin produce synergistic, rather than merely additive, anticoagulant effects.

The small molecule direct and specific FXa inhibitor PRT 54004, and the indirect specific FXa inhibitor fondaparinux, like FXa aptamer, delay, but do not prevent clot formation in TEG assays (data not shown). However, (1) the combination of FIXa aptamer and PRT 54004, and (2) the combination of FIXa aptamer and fondaparinux prevent in vitro clot formation in TEG assays for 180 minutes through synergistic anticoagulant effects (data not shown).

Synergistic anticoagulant effects produced by argatroban and either of two small molecule direct FXa inhibitors (Gould et al, Journal of Thrombosis & Haemostasis 4:834-841 (2006), Giardino et al, Blood Coagulation & Fibrinolysis 21:128-134 (2010)) have also been demonstrated both in vivo and in non-TEG in vitro studies performed on blood and plasma. In addition, the synergy due to the simultaneous FXa inhibition and thrombin inhibition produced by EP217609 may, at least in part, contribute to the anticoagulant efficacy of that investigational drug.

In summary, several whole blood TEG assays reveal that several anticoagulation regimens that comprise combined FIXa and FXa inhibition, FIXa and thrombin inhibition, or FXa and thrombin inhibition result " . . . in prolongation of clot initiation and suppression of propagation and strength to an extent similar clinically to heparin-activated antithrombin . . . ." Hence, according to Nielsen et al, one or more of those regimens are " . . . likely 'safe' for the conduct of CPB. (Nielsen et al, J. Heart Lung Transplant. 25:653-663 (2006))" (emphasis added)

Example II

Figure 18:
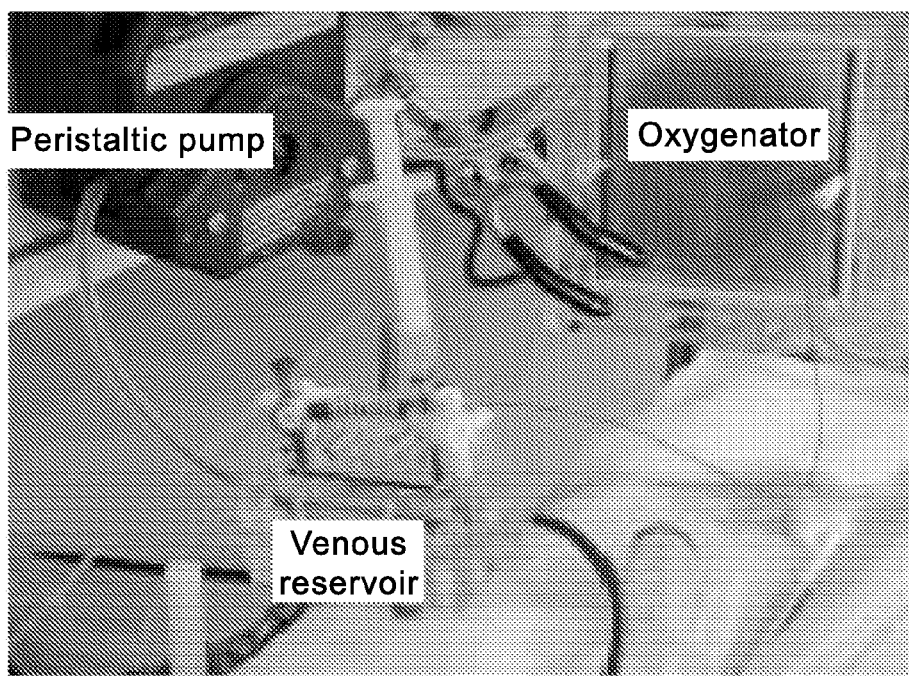
FIG. 18. Isolated oxygenator circuit.

FIG. 18 is a photograph of the isolated 25-mL oxygenator circuit, the principal components of which are a 5-mL venous reservoir, a custom-designed polypropylene membrane oxygenator, segments of 1.6 mm internal diameter silicone tubing that connect the oxygenator with the reservoir, and a small roller pump. The oxygenator is constructed of two 10 cm×10 cm rectangular Plexiglas® shells that surround and hold a 9.5 cm×9.5 cm×1 mm polypropylene membrane. Its priming volume is 4 mL. The pump circulates the blood continuously from the reservoir through the oxygenator and back to the reservoir.

Unpublished experiments have shown that the thrombogenicity of the isolated 25-mL oxygenator circuit resembles the thrombogenicity of a CPB circuit. For example, FIXa aptamer alone at a concentration of 2 micromolar failed to prevent clot formation in whole blood circulated within the isolated oxygenator circuit. Clot formation occurred approximately 30 minutes after circulation was started. FIXa aptamer also failed to effect satisfactory anticoagulation during a 3-hr period of CPB performed on a juvenile pig. In contrast, UFH 5, U/mL, as well as the combination of RNA9.3t, $RNA_{11F7t}$, and thrombin aptamer both prevented clot formation in blood circulated for 2 hours in the isolated circuit.

As shown in Example I, TEG studies of (1) each combination of 2 of those 3 aptamer anticoagulants and (2) several combinations of one aptamer anticoagulant plus one non-aptamer anticoagulant suggest that several of those pair combinations will also effect satisfactory anticoagulation in an isolated oxygenator circuit.

Anticoagulation strategies that have effected satisfactory anticoagulation in both TEG assays and in small circuit experiments can be further tested as CPB anticoagulants in large animal experiments.

Example III

Experimental Details
Materials:

Normal pooled platelet poor plasma was purchased from George King Biomedical (Overland Park, Kans.). Phosphate buffered saline (PBS), tetramethylsilane (TMS), and formaldehyde were purchased from Sigma-Aldrich, (St. Louis, Mo.). Ethanol was purchased from EMD (Darmstadt, Germany) and glutaraldehyde was purchased from TCI America (Portland, Oreg.). UFH and protamine sulfate were purchased from APP Pharmaceuticals, LLC (Schaumburg, Ill.). CDP was a generous gift from Jeremy Heidel at Calando Pharmaceuticals.
Modified RNA Aptamers and DNA Antidotes:

The FIXa aptamer (Rusconi et al, Nature 419: 90-4 (2002)) (9.3T; 5'-AUGGGGACUAUAC-CGCGUAAUGCUGCCUCCCCAU-3' (SEQ ID NO: 1)), FXa aptamer (Buddai et al, J Biol Chem 285:52 12-23 (2010)) (11F7T; 5'-GAGAGCCCCAGCGAGAUAAUAC-UUGGCCCCGCUCUU-3' (SEQ ID NO: 2)), prothrombin aptamer (R9D-14T7; 5'-GGCGGTCGATCACACAGT-TCAAACGTAATAAGCCAATGTACGAGGCAGACGA CTCGCC-3' (SEQ ID NO: 3)) (Bompiani et al, J Thromb Haemost 10:870-80 (2012)), and 9.3T mutant control (Rusconi et al, Nature 419: 90-4 (2002)) (9.3Tmut; 5'-AUGGGGACUGUGCCGCGUAAUGCUGCCUC-CCCAU-3' (SEQ ID NO: 4)) were purchased from ST Pharm Co., Ltd. (Seoul, Korea). The FVIIa aptamer (Layzer and Sullenger, Oligonucleotides 17:1-11 (2007)) (7S-1; 5'-GGGAGGACGAUGCGGACUCCUCCAAGCGAC-CAACAUCGGUCCCGUUUCAGA UCAACAGACGA-CUCGCUGAGGAUCCGAGA-3' (SEQ ID NO: 5)), 11F7T mutant control (Buddai et al, J Biol Chem 285:52 12-23 (2010)) (11F7Tmut; 5'-GAGAGCCCCAGCGA-GAUAAUACUUGUACCCGCUCUU-3' (SEQ ID NO: 6)), R9D-14T mutant control (R9D-14Tmut 5'-GGCGGTCGAT-CACACAGTTCAAACGTAATAAGCCGGCGTACGAG-GCAGACGA CTCGCC-3' (SEQ ID NO: 7)) (Bompiani et al, J Thromb Haemost 10:870-80 (2012)) and 7S-1 mutant control (7S-1mut; 5'-GGGAGGACGAUGCGGACUC-CUCCAAGCGACCAACAUCGGUCUUAUUUCAGA UCAA CAGACGACUCGCUGAGGAUCCGAGA-3' (SEQ ID NO: 8)) (unpublished) were transcribed and purified using in vitro methods previously described (Layzer and Sullenger, Oligonucleotides 17:1-11 (2007)). For all of the RNA aptamers the pyrimidines are modified ribonucleotides, where "C" denotes a 2'Fluorocytosine and "U" denotes a 2'Fluorouracil. Prior to all functional assays, the aptamers were diluted in Hepes/saline buffer (20 mM Hepes, pH 7.4, 150 mM NaCl, and 2 mM $CaCl_2$), heated to 65° C. for 5 min, and cooled to ambient temperature for 3 min to re-nature the RNA. For combinations of two aptamers, the aptamers were diluted and heated/cooled separately and then combined on ice to prevent potential inter-molecular interactions.

The 11F7T DNA antidote (5'-TATTATCTCGCTGGG-3' (SEQ ID NO: 9)) and the R9D-14T DNA antidote (5'-GTCTGCCTCGTACATTGGCT-3' (SEQ ID NO: 10)) were designed via Watson-Crick base pairing as previously described (Bompiani et al, J Thromb Haemost 10:870-80 (2012)) and synthesized by Integrated DNA Technologies, Inc. (Coralville, Iowa).

Plasma Clotting Assays:

The activated partial thromboplastin time (aPTT) and prothrombin time (PT) assays were performed on a model ST4 mechanical coagulometer (Diagnostica Stago, Parsippany, N.J.) as previously described (Bompiani et al, J Thromb Haemost 10:870-80 (2012)). For the aPTT, 50 μL of normal human platelet poor plasma (PPP) was incubated with 50 μL TriniClot aPTT S (Trinity BioTech, Bray, Co Wicklow, Ireland) at 37° C. for 5 min. Aptamer(s) (5 μL) was added, and the mixture was incubated at 37° C. for another 5 min, and $CaCl_2$ (50 μL) was added to initiate the assay. For the PT, 50 μL of normal human PPP was incubated with 5 μL of aptamer(s) at 37° C. for 5 min. TriniClot PT Excel reagent (Trinity BioTech, Bray, Co Wicklow, Ireland) (100 μL) was added to initiate the reaction. Assays with a combination of two aptamers contain an equimolar concentration of each individual aptamer, and the data shown are the total RNA concentration.

Calibrated Automated Thrombography:

Normal human platelet poor plasma (80 μL) was mixed with aptamer(s) (10 μL) in an Immunolon 2HB U Bottom Mictrotiter 96-well plate (Thermo Labsystems, Franklin, Mass.) and incubated at 37° C. for 5 min. PPP reagent (Diagnostica Stago, Parsippany, N.J.) (either 1 ρM or 5 ρM TF, 20 μL, Diagnostica Stago) was added, and the mixture was incubated at 37° C. for another 5 min. FluCa (Diagnostica Stago) (10 μL) was added to initiate the assay and thrombin generation was measured for 60 minutes at 37° C. with a Fluoroskan Ascent fluorometer (ThermoLabsystem, Helsinki, Finland) according to the manufacturer's instructions. The amount of thrombin generated was quantified by comparison to an assay with thrombin calibrator reagent (Diagnostica Stago) that has a known activity toward the fluorogenic substrate. The lag time, peak amount of thrombin generated, and endogenous thrombin potential (ETP) were automatically calculated by the Thrombinoscope software (Thrombinoscope BV, the Netherlands).

Thromboelastography:

Blood was drawn from healthy, consented volunteers under a Duke University Institutional Review Board approved protocol and anticoagulated with 3.2% sodium citrate. Whole blood (320 μL) was mixed with anticoagulant (heparin or aptamers) (10 μL) and kaolin (Haemonetics, Niles, Ill.) (10 μL) or CAT PRP reagent (Diagnostica Stago, 0.33 ρM TF final) (10 μL) was added to stimulate clotting. $CaCl_2$ (20 μL) was immediately added to overcome the citrate, the mixture was added to a plain disposable plastic TEG cup (Haemonetics), and the assay was run according to the manufacturer's instructions. Clot formation at 37° C. was measured with a Thromboelastograph Analyzer (Haemonetics, Niles, Ill.) until a stable clot was formed (i.e., a maximum amplitude was reached) or for three hours with the aptamer combinations. The time lag time, α-angle, and maximum amplitude were automatically calculated by the TEG® Analytical Software version 4.2.3 (Haemonetics).

For the antidote reversal TEGs, whole blood was anticoagulated with a combination of the FXa (0.5 μM) and prothrombin (5 μM) aptamers for 1 hour as described, antidote (10 μL) was added, and the assay was continued until a stable clot was formed. For complete antidote reversal at one hour a 4-fold molar excess of protamine (22 μM) was added, 50 μg of CDP was added, or a 2-fold molar excess of the R9D-14T oligonucleotide (10 μM) in combination with a 3-fold molar excess of the 11F7T antidote oligonucleotide (1.5 μM) was added.

Extracorporeal Membrane Circuit Oxygenation:

The extracorporeal minicircuit consisted of a sample line, custom-designed 8 mL Plexiglas® venous reservoir, a mechanical roller pump (MasterFlex®; Cole-Parmer Instrument Co., Vernon Hills, Ill.), and a custom-designed small-volume oxygenator that are all connected by MasterFlex precision silicone tubing (Cole-Parmer Instrument Co.) (de Lange et al, Br J Anaesth 99:177-83 (2007), de Lange et al, J Cardiothorac Surg 3:51 (2008). The 4 mL priming volume oxygenator is comprised of two Plexiglas® shells (12.8 cm×12.8 cm×2.7 cm) that cover a disposable three layer artificial diffusion membrane comprised of hollow polypropylene fibers glued together in a crosswise fashion. The surface area available for gas exchange is 558 $cm^2$. To prevent heat loss, one of the shells has an integrated heat exchanger, and the temperature was maintained at approximately 33° C. with a circulating water bath system (Gaymar Industries, Orchard Park, N.Y.). A MEAS reusable temperature probe (Model 451, Measurement Specialties Inc., Dayton, Ohio) was inserted into the reservoir to continuously measure the temperature, and an in-line flow probe (2N806 flow probe and T208 volume flowmeter; Transonics Systems, Inc., Ithaca, N.Y.) was used to continuously measure the blood flow. The circuit blood $O_2$ level was maintained at 95% and the $CO_2$ was maintained at 5%.

The minicircuit was primed with phosphate buffered saline (PBS) at a flow rate of 50 mL/min for approximately 30 min. Blood was drawn from healthy, consented volunteers and anticoagulated with 3.2% sodium citrate. Approximately 25 mL of citrated blood was incubated with 500 μL of anticoagulant (i.e., UFH or aptamer) at 37° C. for 5 min. The PBS was drained from the minicircuit, and the blood was added and circulated at a rate of 50 mL/min with 95% $O_2$/5% $CO_2$ at approximately 33° C. $CaCl_2$ (660 μL, 6.45 mM final) was added to overcome the citrate and initiate the experiment. Blood samples (~1.5 mL) were withdrawn from the baseline citrated blood (no aptamer) and from the circuit reservoir at 5, 30, 60, 90, and 120 min post circuit initiation, or until visible clot formation. aPTT, PT, ACT-LR, and ACT+ assays (ITC, Edison, N.J.) were immediately run with a Hemochron Jr. signature point of care device (ITC Nexus Dx, Edison, N.J.). To analyze the citrated baseline aPTT, PT, ACT-LR, and ACT+ values, 6.45 mM $CaCl_2$ was added to approximately 100 μL of blood, the mixture was incubated for 30 sec at ambient temperature, and the assay was run according to the manufacturer's instructions. The venous blood gases were analyzed with a GEM Premier 3000 blood gas/electrolyte analyzer (model 5700; Instrumentation Laboratories, Inc, Lexington, Mass.) to determine the hematocrit, $CaCl_2$, $O_2$, and $CO_2$ levels.

Oxygenator Membrane Scanning Electron Microscopy:

After 2 hours of circulation (or until there was visible clot formation), the minicircuit was washed with three volumes (approximately 60 mL) of PBS at a flow rate of 50 mL/min. The oxygenator membrane was removed with forceps, washed with gentle rocking in PBS for approximately 30 sec, then removed and blotted. Three pieces approximately 10 mm×10 mm were excised from different areas of the membrane with a clean razor blade. The membrane pieces were fixed overnight in PBS with 4% formaldehyde and 2% glutaraldehyde, washed two times with PBS, then dehydrated in an ethanol gradient (30% to 100%). The membranes were subsequently submerged in tetramethylsilane (TMS) for 10 min, then removed and placed in a desiccator overnight. Desiccated membrane specimens measuring approximately 10 mm×7 mm were affixed with double sided tape to circular metal stubs approximately 14 mm in diameter. The specimens were gold sputter coated in a Denton Vacuum Desk IV® (Denton Vacuum LLC, Moorestown, N.J.) according to the manufacturer's instructions. The scanning electron microscopic (SEM) images were obtained with a FEI XL 30 FE SEM (FEI, Hillsboro, Oreg.).

Aptamer Synergy Calculations:

Drug synergy for aptamer combinations in the aPTT and PT was assessed with the algebraic method described by Berenbaum (Berenbaum, Clin Exp Immunol 28:1-18 (1977)). Drug synergy was calculated according to the following equation:

$$\frac{\text{dose of } A}{A_e} + \frac{\text{dose of } B}{B_e} = 1$$

where $A_e$ and $B_e$ are concentrations of the individual aptamers that produce equivalent clotting times, and "dose of A" and "dose of B" are the respective concentrations of aptamers when tested in combination that produce the same clotting time as $A_e$ and $B_e$. Additive aptamer combinations were defined as combinations that have a sum of fractions equal to one, while synergistic aptamer combinations were defined as combinations that have a sum less than one.

Results

Individual Aptamers Uniquely Impair Thrombin Generation and Produce Varying Levels of Anticoagulation:

The anticoagulant effects of the FVII (7S-1) (Layzer and Sullenger, Oligonucleotides 17:1-11 (2007)), FIX (9.3T) (Rusconi et al, Nature 419: 90-4 (2002)), FX (11F7T) (Buddai et al, J Biol Chem 285:52 12-23 (2010)), and prothrombin (R9D-14T) (Bompiani et al, J Thromb Haemost 10:870-80 (2012)) aptamers, which are all 2'-Fluoro modified single-stranded RNAs that vary in size from 34-80 nucleotides (FIG. 19). Previous mechanistic studies with several of these aptamers indicate that the aptamers bind to macromolecular binding sites present on both the zymogen and enzyme form of the protein and thereby inhibit protein-protein interactions that are essential for coagulation (Buddai et al, J Biol Chem 285:52 12-23 (2010), Bompiani et al, J Thromb Haemost 10:870-80 (2012), Sullenger et al, J Biol Chem 287:12779-86 (2012)). Unlike small molecule anticoagulants that only inhibit enzyme activity, aptamer binding impairs both enzyme generation (zymogen cleavage) and enzyme function.

To compare the anticoagulant effect of these four aptamers, dose-response titrations were performed in several clinical plasma-based clotting assays. The activated partial thromboplastin time (aPTT) and prothrombin time (PT) are plasma clotting assays that are clinically used to probe for abnormalities in the intrinsic and extrinsic coagulation pathways, respectively (Van Cott et al, editors. Jacobs & DeMott laboratory test handbook. 5th ed. Hudson Ohio: Lexi-Comp. p. 327-58 (2001)). These relatively simple assays measure the time until clot formation in platelet poor plasma (PPP) in response to either robust tissue factor (TF), or contact stimulation via negatively charged surfaces (i.e., silica, kaolin, celite). Titrations with the individual aptamers in the respective clotting assays show that all of the aptamers dose-dependently anticoagulate the plasma and prolong the aPTT and PT clotting time to varying degrees. At high concentrations, the prothrombin aptamer (R9D-14T) was the most robust anticoagulant and inhibited greater than 96% of prothrombin activity in the aPTT and PT. At 4 µM, R9D-14T increased the aPTT clotting time approximately 18-fold and the PT clotting time greater than 80-fold (exceeded the assay limit of 999 sec). The FXa aptamer (11F7T) was also a robust anticoagulant, and at high concentrations (4 µM) it inhibited greater than 99% of FXa activity by increasing the aPTT clotting time approximately 11-fold; however, 11F7T had a diminished effect in the PT and only increased the clotting time approximately 8-fold. At the same dose, the FIXa aptamer (9.3T) inhibited greater than 99% of FIX activity and increased the aPTT clotting time approximately 5.5-fold, while the FVIIa aptamer (7S-1) increased the PT clotting time 3-fold and inhibited greater than 99% of FVII activity (FIGS. 20A and 20B). Thus, the data indicate that all of the aptamers inhibit their target proteins extremely well in vitro. The prothrombin and FX aptamers are the most robust anticoagulants at high concentrations, while the FVII and FIX aptamers are superior anticoagulants at low concentrations in these clinical assays.

Thrombin is the final protease formed in the coagulation cascade, and the rate of thrombin generation and the total amount of thrombin generated is associated with blood clot formation and stability (Wolberg, Blood Rev 21:131-42 (2007)). To gain more information about the impact of aptamer anticoagulation on the kinetics of thrombin generation, the individual aptamers were analyzed with calibrated automated thrombography (CAT). The CAT assay measures real-time thrombin generation in plasma by monitoring cleavage of a thrombin-specific fluorogenic substrate in response to TF stimulation (Heruker et al, Pathophysiol Haemost Thromb 33: 4-15 (2003)). The parameters of thrombin generation analyzed include: the lag time (time until thrombin generation begins), the peak (the maximal amount of thrombin generated at a given time) and the endogenous thrombin potential (ETP, the total amount of thrombin generated). Similar to the aPTT and PT clotting assays, all of the individual aptamers dose-dependently impacted the various parameters of thrombin generation (FIG. 21 and Table 1). 7S-1 dose-dependently increased the lag time, decreased the peak thrombin concentration, and slightly decreased the total amount of thrombin generated with a high concentration of TF (5 pM TF and 4 µM lipid PPP reagent) (FIG. 21A and Table 1). However, this aptamer was only able to partially decrease thrombin generation, as super-saturating concentrations greater than 30 nM did not produce an additional anticoagulant effect (Table 1). 9.3T minorly impacted all parameters of thrombin generation with the high TF reagent; however, because high concentrations of TF may bypass FIX activity by directly generating FXa, the manufacturer recommends low concentrations of TF for analyzing FIX deficient (i.e, Hemophilia B) plasma in the CAT. 9.3T had a dose-dependent effect with low TF (1 pM TF and 4 µM lipid PPP reagent) and decreased the peak thrombin generation, but only had a small impact on the lag time and the total amount of thrombin generated (FIG. 21B). However, even with low TF conditions 9.3T was only able to partially decrease thrombin generation, as concentrations greater than 120 nM did not provide additional anticoagulation (data not shown). In contrast, 11F7T and R9D-14T both had a dose-dependent effect with high TF and severely impaired all parameters of thrombin generation at high aptamer concentrations (FIGS. 21C and 212D, respectively). Strikingly, 5 µM of R9D-14T completely inhibited thrombin generation in three independent experiments (FIG. 21D and Table 1).

TABLE 1

Calibrated automated thrombography parameters with various concentrations of individual aptamers and various concentrations of tissue factor.

| Aptamer | RNA (nM) | TF (pM) | Lag-time (min) | Peak (nM) | ETP (nM*min) | TTP (min) |
|---|---|---|---|---|---|---|
| None | — | 1 | 2.95 ± 0.06 | 221.56 ± 5.88 | 1497.25 ± 96.75 | 6.84 ± 0.10 |
|  | — | 5 | 1.69 ± 0.09 | 325.43 ± 11.15 | 1721.90 ± 61.35 | 4.15 ± 0.13 |
| 7S-1 | 1.25 | 5 | 1.67 ± 0.19 | 314.56 ± 14.17 | 1657.33 ± 42.72 | 4.28 ± 0.20 |
|  | 2.5 |  | 2.00 ± 0.17 | 274.39 ± 29.71 | 1603.50 ± 28.00 | 5.29 ± 0.55 |
|  | 5 |  | 3.17 ± 0.19 | 238.68 ± 31.03 | 1656.20 ± 96.89 | 7.34 ± 0.55 |
|  | 10 |  | 4.51 ± 0.42 | 130.54 ± 14.06 | 1339.50 ± 21.15 | 11.01 ± 0.79 |
|  | 30 |  | 6.01 ± 0.44 | 199.25 ± 41.13 | 1523.50 ± 160.63 | 10.80 ± 1.03 |
| 9.3T | 15 | 1 | 3.06 ± 0.15 | 195.04 ± 6.91 | 1463.50 ± 19.59 | 7.34 ± 0.26 |
|  | 30 |  | 3.00 ± 0.10 | 147.88 ± 4.28 | 1350.17 ± 28.02 | 8.12 ± 0.34 |
|  | 60 |  | 2.89 ± 0.15 | 110.65 ± 6.70 | 1261.50 ± 64.85 | 8.95 ± 0.15 |
|  | 120 |  | 2.72 ± 0.05 | 86.13 ± 3.02 | 1125.00 ± 31.79 | 9.34 ± 0.19 |
| 9.3T | 15 | 5 | 1.72 ± 0.20 | 341.90 ± 12.54 | 1812.50 ± 81.01 | 4.23 ± 0.24 |
|  | 30 |  | 1.56 ± 0.20 | 316.98 ± 3.28 | 1723.67 ± 57.51 | 4.28 ± 0.40 |
|  | 60 |  | 1.70 ± 0.11 | 283.76 ± 3.20 | 1741.10 ± 78.84 | 4.90 ± 0.31 |
|  | 120 |  | 1.60 ± 0.15 | 272.90 ± 9.97 | 1674.50 ± 56.02 | 4.74 ± 0.37 |
| 11F7T | 125 | 5 | 3.00 ± 0.22 | 227.75 ± 43.47 | 1612.90 ± 142.40 | 7.24 ± 0.77 |
|  | 250 |  | 4.94 ± 0.38 | 120.68 ± 21.79 | 1220.50 ± 182.02 | 11.70 ± 1.13 |
|  | 500 |  | 7.97 ± 0.93 | 65.56 ± 14.57 | 738.60 ± 202.92 | 16.47 ± 1.83 |
|  | 1,000 |  | 9.50 ± 1.00 | 36.84 ± 14.42 | 459.40 ± 199.39 | 20.10 ± 2.96 |
| R9D-14T | 625 | 5 | 1.55 ± 0.08 | 314.82 ± 25.02 | 1492.50 ± 54.94 | 3.88 ± 0.18 |
|  | 1,250 |  | 1.55 ± 0.08 | 269.45 ± 13.17 | 1293.00 ± 67.66 | 3.67 ± 0.18 |
|  | 2,500 |  | 4.37 ± 0.71 | 192.66 ± 31.04 | 1170.90 ± 90.47 | 7.64 ± 1.31 |
|  | 5,000 |  | No thrombin generation |  |  |  |
| 7S-1mut | 30 | 5 | 1.73 ± 0.06 | 357.63 ± 7.76 | 1890.67 ± 23.55 | 4.45 ± 0.06 |
| R9D-14Tmut | 5,000 | 5 | 1.44 ± 0.06 | 312.12 ± 8.89 | 1564.33 ± 121.22 | 3.66 ± 0.17 |
| 11F7Tmut | 1,000 | 5 | 1.39 ± 0.06 | 391.12 ± 13.27 | 1902.67 ± 87.44 | 3.73 ± 0.06 |
| 9.3Tmut | 120 | 1 | 3.11 ± 0.20 | 219.57 ± 33.93 | 1446.83 ± 59.97 | 7.17 ± 0.59 |
|  |  | 5 | 1.89 ± 0.06 | 355.41 ± 17.21 | 1820.83 ± 80.77 | 4.34 ± 0.10 |

*TF = tissue factor; ETP = endogenous thrombin potential; TTP = time to peak. The data represent the mean ± SEM of three independent experiments run in duplicate.

To show that inhibition of thrombin generation is specific for aptamer RNA sequence/folding, point mutant control RNAs were designed and tested. Rusconi et al. showed that mutating two conserved nucleotides with the family of FIXa aptamers generated via SELEX completely abolished 9.3T activity, indicating that these nucleotides are crucial for RNA folding and/or protein binding (Rusconi et al, Nature 419: 90-4 (2002)). Similar point mutant controls were also designed for 11F7T, R9D-14T, and 7S-1 (FIG. 19). Parallel CAT experiments were performed with the point mutant control RNA sequences at the same concentrations to show that aptamer anticoagulation is specific and not engendered by high concentrations of modified RNA. As was expected, none of the point mutant control RNAs had an appreciable impact on thrombin generation (Table 1).

Although the aPTT, PT, and CAT assays provide basic information about dose-dependent anticoagulation, these assays are performed in an environment that lacks platelets. Platelets play a crucial role in clot formation by providing a membrane surface upon which the clotting factors assemble, by aggregating and becoming physically incorporated into the blood clot, and by releasing internal stores of agonists that amplify coagulation (Monroe et al, Arterioscler Thromb Vasc Biol 22:138 1-9 (2002)). Therefore, a study was made of aptamer anticoagulation with thromboelastography (TEG), which provides real-time information about the kinetics of clot formation in whole blood (Reikvam et al, Transfus Apher Sci; 40:119-23 (2009). The TEG assay uses mechanical motion to quantify the physical properties of clot formation, including the lag time (the time until clot formation), the α-angle (the rate of clot formation), and the maximum amplitude (the mechanical strength of the clot formed).

When blood was stimulated via the intrinsic pathway with kaolin, the 9.3T, 11F7T, and R9D-14T aptamers all produced a dose dependent effect and impaired clot formation (FIG. 22 and Table 2). At a saturating concentration, 9.3T increased the lag-time (6.9 vs. 25.5 min), decreased the α-angle (62.4 vs. 37.6°), and decreased the maximum amplitude (63.5 vs. 55.4 mm) (FIG. 22B). 11F7T at a saturating concentration had a more robust effect and increased the lag-time (6.9 vs. 39.6 min), decreased the α-angle (62.4 vs. 18°), and decreased the maximum amplitude to (63.5 vs. 39.6 mm) (FIG. 22C). Finally, R9D-14T at a high concentration increased the lag time to (6.9 vs. 21.5 min), decreased the α-angle to (62.4 vs. 30°), and decreased the maximum amplitude (63.5 vs. 49.6 mm) (FIG. 22D and Table 2).

TABLE 2

Thromboelastography clot formation parameters for whole blood anticoagulated with various individual aptamers and stimulated with kaolin.

| Aptamer | RNA (µM) | Lag-time (min) | Angle (deg) | Max. Amplitude (mm) |
|---|---|---|---|---|
| None | — | 6.9 ± 0.8 | 62.4 ± 1.6 | 63.5 ± 0.9 |
| 9.3T | 0.5 | 22.8 ± 2.0 | 41.4 ± 0.5 | 55.4 ± 3.2 |
|  | 1.0 | 25.5 ± 1.8 | 37.6 ± 7.1 | 55.4 ± 2.6 |
|  | 2.0 | 29.9 ± 1.4 | 36.9 ± 2.9 | 55.9 ± 3.4 |
| 11F7T | 0.5 | 15.6 ± 0.8 | 40.3 ± 1.4 | 52.4 ± 1.6 |
|  | 1.0 | 20.6 ± 3.0 | 28.7 ± 5.0 | 48.2 ± 3.7 |
|  | 2.0 | 39.6 ± 9.1 | 18.0 ± 5.9 | 39.6 ± 4.4 |
| R9D-14T | 1.25 | 7.1 ± 1.4 | 60.4 ± 2.4 | 62.0 ± 3.0 |
|  | 2.0 | 8.3 ± 2.0 | 48.1 ± 9.7 | 56.0 ± 6.3 |
|  | 5.0 | 21.5 ± 4.9 | 30.0 ± 5.7 | 49.6 ± 3.6 |

TABLE 2-continued

Thromboelastography clot formation parameters for whole blood anticoagulated with various individual aptamers and stimulated with kaolin.

| Aptamer | RNA (μM) | Lag-time (min) | Angle (deg) | Max. Amplitude (mm) |
|---|---|---|---|---|
| 9.3Tmut | 2.0 | 7.3 ± 2.1 | 58.6 ± 7.8 | 60.1 ± 5.8 |
| 11F7Tmut | 2.0 | 5.1 ± 0.6 | 69.7 ± 1.2 | 65.8 ± 0.8 |
| R9D-14Tmut | 5.0 | 6.5 ± 0.4 | 56.0 ± 4.8 | 61.9 ± 4.0 |

The data represent the mean ± SEM of three independent experiments with blood from three different healthy donors.
min = minutes;
deg = degrees;
mm = millimeters;
max. amplitude = maximum amplitude Because kaolin stimulates blood via the intrinsic pathway, it is unlikely that 7S-1 (FVIIa aptamer) would impair clot formation with this type of stimulation; thus, this aptamer was tested in a modified TEG with TF stimulation. CAT platelet rich plasma (PRP) reagent (TF) was diluted to a final concentration of 0.33 pM TF to stimulate clotting. Control baseline assays that were simulated with TF produced lag-times, α-angles, and maximum amplitudes that are comparable to the normal kaolin baseline parameters (FIG. 22E). At a saturating concentration, 7S-1 slightly increased the lag-time (4.6 vs. 6.6 min), but did not appreciably impact the α-angle (65.2 vs. 61.9°) or maximum amplitude (67.8 vs. 63.1 mm) with TF stimulation (FIG. 22F and Table 3). A saturating concentration of 9.3T did not increase the lag time (4.6 vs. 4.5 min), the α-angle (65.2 vs. 66.3°), or the maximum amplitude (67.8 vs. 69.1 mm) with TF stimulation (FIG. 22G). In contrast, 11F7T at a saturating concentration increased the lag time (4.6 vs. 51.1 min), decreased the α-angle (65.2 vs. 21.4°), and decreased the maximum amplitude (67.8 vs. 51.1 mm) (FIG. 22H). Finally, a high concentration of R9D-14T (5 μM) increased the lag time (4.6 vs. 39.4 min), decreased the α-angle (65.2 vs. 15.2°), and decreased the maximum amplitude (67.8 vs. 36.8 mm) in a TF-stimulated TEG (FIG. 22I and Table 3). Similar to the plasma CAT assays, the point mutant control aptamers did not impair TEG whole blood clot formation with either kaolin or TF stimulation (Tables 2 and 3).

TABLE 3

Thromboelastography clot formation parameters for whole blood anticoagulated with various individual aptamers and stimulated with tissue factor.

| Aptamer | RNA (μM) | Lag-time (min) | Angle (deg) | Max. Amplitude (mm) |
|---|---|---|---|---|
| None | — | 4.6 ± 0.2 | 65.2 ± 2.4 | 67.8 ± 1.2 |
| 7S-1 | 0.12 | 4.5 ± 0.6 | 65.2 ± 5.2 | 63.0 ± 3.7 |
|  | 0.25 | 5.1 ± 1.2 | 62.4 ± 3.7 | 64.0 ± 2.8 |
|  | 0.50 | 6.6 ± 0.8 | 61.9 ± 3.3 | 63.1 ± 2.0 |
| 9.3T | 1.00 | 4.5 ± 0.5 | 66.3 ± 1.3 | 69.1 ± 1.5 |
| 11F7T | 2.00 | 51.1 ± 12.2 | 21.4 ± 7.3 | 51.1 ± 1.6 |
| R9D-14T | 5.00 | 39.4 ± 5.0 | 15.2 ± 2.5 | 36.8 ± 1.4 |
| 9.3Tmut | 1.00 | 2.7 ± 0.4 | 69.0 ± 4.8 | 67.2 ± 1.6 |
| 11F7Tmut | 2.00 | 3.9 ± 0.2 | 68.5 ± 0.5 | 67.9 ± 0.7 |
| R9D-14Tmut | 5.00 | 2.7 ± 0.2 | 72.3 ± 0.7 | 66.1 ± 1.4 |
| 7S-1mut | 0.50 | 3.1 ± 0.1 | 67.8 ± 3.8 | 67.2 ± 0.7 |

The data represent the mean ± SEM of three independent experiments with blood from three different healthy donors.
min = minutes;
deg = degrees;
mm = millimeters;
max. amplitude = maximum amplitude.

Several Combinations of Two Anticoagulant Aptamers Synergistically Impair Thrombin Generation and Fibrin Clot Formation:

To determine the effect of inhibiting multiple proteins within the same or different pathways in the coagulation cascade, combinations of two aptamers were also analyzed. Combinations of drugs that inhibit several enzymes within a biological pathway may synergize; that is, their combined inhibitory effect may exceed the additive inhibitory effects produced by each inhibitor alone (Berenbaum, Clin Exp Immunol 28:1-18 (1977)). Combinations of two different aptamers at equimolar concentrations were tested in the plasma clot-based assays to determine the effect on plasma clotting time and assess drug synergy. At high concentrations (≥1 μM total RNA), all of the aptamer combinations tested in the aPTT assay (i.e., 9.3T+11F7T, 9.3T+R9D-14T, and 11F7T+R9D-14T) synergistically prolonged the clotting time to greater than 999 sec, which is the assay maximum (FIG. 23A). Similarly, the 7S-1+11F7T combination at high concentrations synergistically prolonged the PT clotting time, and at 4 μM total RNA increased the clotting time approximately 50-fold; however, the 7S-1+R9D-14T aptamer combination did not synergistically increase the PT clotting time, and at 4 μM total RNA only increased the clotting time approximately 28-fold (FIG. 23B). Thus, several combinations of two anticoagulant aptamers result in synergistic anticoagulation that severely impairs clot formation in human plasma.

Combinations of two aptamers were also tested in the CAT assay to determine the effect on thrombin formation. When stimulated with 5 pM TF, several aptamer combinations markedly inhibited thrombin formation (Table 4). The 7S-1+9.3T aptamer combination only slightly increased the lag-time and ETP, but decreased the peak by greater than 70% compared to 7S-1 anticoagulation alone. The 7S-1+11F7T aptamer combination had a minor impact on all 3 parameters of thrombin generation compared to 7S-1 alone. This combination may be more effective at higher doses of 11F7T; however, high doses of 11F7T are difficult to analyze with CAT because high concentrations of 11F7T alone can severely impair thrombin generation. Thus, it may be difficult to analyze synergy with 11F7T in this environment.

TABLE 4

Calibrated automated thrombography parameters with various aptamer combinations and 5 pM tissue factor.

| Aptamer 1 (nM) | Aptamer 2 (nM) | Lag-time (min) | Peak (nM) | ETP (nM*min) |
|---|---|---|---|---|
| 7S-1 (5 nM) | 9.3T (60 nM) | 2.39 ± 0.24 | 146.79 ± 2.94 | 1501.83 ± 53.75 |
| 7S-1 (30 nM) | 9.3T (60 nM) | 6.92 ± 0.40 | 89.33 ± 17.67 | 1186.75 ± 66.18 |
| 7S-1 (30 nM) | 9.3T (120 nM) | 7.17 ± 0.50 | 54.48 ± 1.46 | 966.67 ± 37.29 |
| 7S-1 (5 nM) | 11F7T (125 nM) | 4.09 ± 0.24 | 192.85 ± 6.26 | 1599.63 ± 64.19 |
| 7S-1 (30 nM) | 11F7T (125 nM) | 7.09 ± 0.44 | 161.55 ± 38.63 | 1420.13 ± 141.24 |
| 7S-1 (5 nM) | R9D-14T (2,500 nM) | 4.21 ± 0.87 | 222.91 ± 13.05 | 1223.50 ± 26.77 |
| 7S-1 (30 nM) | R9D-14T (2,500 nM) | 12.78 ± 3.59 | 91.10 ± 25.65 | 610.2 ± 175.03 |
| 9.3T (60 nM) | 11F7T (125 nM) | 3.08 ± 0.45 | 146.32 ± 33.12 | 1312.50 ± 111.40 |
| 9.3T (120 nM) | 11F7T (125 nM) | 2.63 ± 0.36 | 196.93 ± 28.49 | 1546.50 ± 16.93 |
| 9.3T (60 nM) | R9D-14T (2,500 nM) | 3.17 ± 0.40 | 86.01 ± 26.94 | 723.88 ± 118.97 |
| 9.3T (120 nM) | R9D-14T (2,500 nM) | 2.00 ± 0.15 | 68.89 ± 21.28 | 471.63 ± 191.73 |
| 11F7T (125 nM) | R9D-14T (2,500 nM) | 5.36 ± 0.46 | 140.71 ± 32.32 | 819.25 ± 187.55 |
| 7S-1 (30 nM) | 9.3Tmut (120 nM) | 5.63 ± 0.37 | 167.65 ± 37.80 | 1430.00 ± 96.80 |
| 7S-1 (30 nM) | 11F7Tmut (125 nM) | 4.78 ± 0.05 | 204.57 ± 11.04 | 1494.17 ± 5.42 |
| 7S-1 (30 nM) | R9D-14Tmut (2,500 nM) | 4.27 ± 0.36 | 203.31 ± 41.16 | 1514.20 ± 70.90 |
| 11F7T (125 nM) | 9.3Tmut (120 nM) | 2.63 ± 0.32 | 273.03 ± 31.75 | 1591.63 ± 75.95 |
| 9.3T (120 nM) | R9D-14Tmut (2,500 nM) | 1.28 ± 0.05 | 323.17 ± 23.85 | 1680.83 ± 131.88 |
| 11F7T (125 nM) | R9D-14Tmut (2,500 nM) | 2.72 ± 0.15 | 247.52 ± 18.02 | 1445.00 ± 84.26 |

*TF = tissue factor; ETP = endogenous thrombin potential.
The data represent the mean ± SEM of three independent experiments run in duplicate.

In contrast to the PT assay data, the 7S-1+R9D-14T combination markedly impaired all 3 parameters of thrombin generation. Compared to 7S-1 anticoagulation alone, a saturating concentration of 7S-1 in combination with a sub-saturating concentration of R9D-14T doubled the lag time, decreased the peak by greater than 50%, and decreased the ETP by approximately 60%. Interestingly, the 9.3T+11F7T combination did not appear as powerful as other aptamer combinations in the CAT; this combination had a negligible impact on the lag time and ETP, although it did slightly decrease the peak thrombin concentration.

9.3T+R9D-14T had little impact on the lag-time, but drastically decreased both the peak and ETP. Compared to R9D-14T alone, a saturating concentration of 9.3T and sub-saturating concentration of R9D-14T in combination decreased the peak by greater than 60% and decreased the ETP by approximately 60%. 11F7T+R9D-14T did not produce as powerful anticoagulation in the CAT compared to previous assays. At sub-saturating doses of each aptamer the combination had no impact on the lag-time, decreased the peak by approximately 25%, and decreased the ETP by approximately 30% (Table 4). However, high doses of R9D-14T and 11F7T are difficult to analyze with CAT because high concentrations of these individual aptamers alone can severely impair thrombin generation. Thus, it may be difficult to analyze synergy with these aptamers in the CAT assay, and it is likely that these aptamers synergize at higher concentrations than tested here.

Control experiments were also performed to determine if aptamer synergy is a result of combining two specific anticoagulants, rather than elevated concentrations of RNA or non-specific interactions between two RNA species. Each functional aptamer was tested in combination with the appropriate point mutant control RNA at the relevant concentrations. As expected, the control combinations did not exhibit synergism and anticoagulated plasma to a degree that is similar to the individual functional aptamers (Table 4).

Combinations of two individual aptamers were further analyzed with TEG in whole blood. The initial TEG studies showed that no single aptamer prevented clot formation for greater than 1 hour following either kaolin or TF stimulation (FIG. 22). However, the aptamer combinations 9.3T+11F7T, 9.3T+R9D-14T, and 11F7T+R9D-14T all inhibited clot formation for greater than 3 hours with kaolin activation, again indicating that aptamer combinations produce powerful anticoagulant cocktails (FIGS. 24B, 24C and 24D, respectively). In contrast, 7S-1+11F7T anticoagulation prevented clot formation for greater than 3 hours in only one of three donors with TF stimulation (lag-time of 78.3 and 73 min) (FIG. 24F). 7S-1+9.3T anticoagulation varied between the three different donors and was not able to prevent clot formation for greater than 55 min (lag time range 12.7-54.4 min) (FIG. 24G). Similar to the data that were obtained with the plasma-based assays, combinations of one functional aptamer and one mutant RNA in the TEG assay did not synergize (Table 5).

TABLE 5

Thromboelastography clot formation parameters for whole blood anticoagulated with various aptamer combinations and stimulated with kaolin or tissue factor.

| Aptamer 1 | Aptamer 2 | Stimulant | Lag-time (min) | Angle (deg) | Max. Amplitude (mm) |
|---|---|---|---|---|---|
| None | None | Kaolin | 7.6 ± 0.6 | 60.8 ± 0.4 | 63.8 ± 1.3 |
| None | None | TF | 4.6 ± 0.2 | 65.2 ± 2.4 | 67.8 ± 1.2 |
| 7S-1 (0.5 µM) | 9.3T (1.0 µM) | TF | 29.7 ± 12.6 | 40.8 ± 9.2 | 60.8 ± 1.5 |
| 7S-1 (0.5 µM) | 11F7T (2.0 µM) | TF | 75.5 ± 2.8* | 8.5 ± 1.5* | 43.2 ± 6.6* |
| 9.3T (1.0 µM) | 11F7T (2.0 µM) | Kaolin | No clot formation within 3 hr | | |
| 9.3T (1.0 µM) | R9D-14T (5.0 µM) | Kaolin | No clot formation within 3 hr | | |
| 11F7T (0.5 µM) | R9D-14T (5.0 µM) | Kaolin | No clot formation within 3 hr | | |
| 7S-1 (0.5 µM) | 9.3Tmut (1.0 µM) | TF | 5.6 ± 0.2 | 54.1 ± 4.9 | 67.5 ± 1.5 |
| 11F7T (2.0 µM) | 7S-1mut (0.5 µM) | TF | 45.5 ± 11.3 | 23.7 ± 10.1 | 51.7 ± 6.1 |
| 11F7T (2.0 µM) | 9.3Tmut (1.0 µM) | Kaolin | 77.8 ± 36.8 | 16.7 ± 11.2 | 31.8 ± 15.4 |
| R9D-14T (5.0 µM) | 9.3Tmut (1.0 µM) | Kaolin | 42.1 ± 1.0 | 17.2 ± 1.4 | 41.6 ± 1.4 |
| 11F7T (0.5 µM) | R9D-14Tmut (5.0 µM) | Kaolin | 26.7 ± 5.1 | 34.3 ± 8.9 | 52.2 ± 3.4 |

The data represent the mean ± SEM of three independent experiments with blood from three different healthy donors.
TF = tissue factor;
min = minutes;
deg = degrees;
mm = millimeters;
max. amplitude = maximum amplitude.
*For this combination, clotting was observed within 3 hours for only two of the three donors; these data represent the mean ± SEM of these two donors.

Extracorporeal Circulation:

Cardiopulmonary bypass (CPB) is the most thrombotic indication for rapid onset anticoagulation. During CPB, the patient's blood is removed from the heart and siphoned off into a machine (extracorporeal circuit) that replaces heart and lung function by controlling the blood temperature, keeping it oxygenated, and circulating it to the extremities (Cohn and Edmunds, Cardiac surgery in the adult. 2nd ed. New York: McGraw-Hill Medical Pub.; 2003. Potent systemic anticoagulation is required during CPB to maintain blood fluidity in response to numerous stimuli, including exposure of the blood to the surgical incision site, repeated and extensive contact of the blood with the foreign materials that comprise the extracorporeal circuit, and extremely high shear in the circuit (Yavari and Becker, J Thromb Thrombolysis 26:218-28 (2008)). Because such an intense degree of anticoagulation is required for CPB, post-operative bleeding is a common surgical complication. Currently, the powerful anticoagulant unfractionated heparin (UFH) and its antidote protamine are the standard of care for CPB anticoagulation. UFH binds to antithrombin (AT), which is a constitutive circulating serine protease inhibitor, and significantly accelerates AT-mediated inhibition of several coagulation enzymes, including FIXa, FXa, and thrombin (Bedsted et al, Biochemistry 42:8143-52 (2003), Olson et al, J Biol Chem 267:12528-38 (1992), Beeler D et al, J Biol Chem 254:2902-13 (1979)).

To assess the clinical applicability of the aptamers, they were compared to UFH anticoagulation in experiments where human blood was continuously circulated within an ex vivo oxygenator minicircuit for two hours. It is believed that the procoagulant stimuli that occur in the minicircuit mimic many of the procoagulant stimuli that occur during CPB. The minicircuit consists of a reservoir, mini-oxygenator, and several lengths of tubing that connect the outflow port of the reservoir to the input port of the oxygenator and the output port of the oxygenator to the input port of the reservoir (de Lange et al, Br J Anaesth 99:177-83 (2007), de Lange et al, J Cardiothorac Surg 3:51 (2008)). The blood is continually circulated from the reservoir to the membrane via a mechanical roller pump, and as the blood is circulated it is heated to approximately 33° C. and supplied with a mixture of 95% $O_2$ and 5% $CO_2$. The goal of these experiments was to determine if an aptamer or combination of aptamers could maintain blood fluidity during extracorporeal circulation and mimic UFH anticoagulation. Whole human blood was anticoagulated with the aptamers or UFH as a control and circulated in the extracorporeal bypass circuit for two hours or until visible clot formation was observed. At specified time points, blood samples were withdrawn to determine the activated clotting time plus (ACT+) on a point of care device.

As expected, UFH anticoagulation (5 U/mL) of blood from three different donors maintained blood fluidity and circuit patency for 2 hours. The ACT+ clotting time was increased from an average of 115 seconds (average donor baseline) to an average maximal clotting time of 423 seconds, which is within the suggested range of 400-480 sec for CPB (Cohn and Edmunds, Cardiac surgery in the adult. 2nd ed. New York: McGraw-Hill Medical Pub.; 2003). At the end of the 2 hour experiment the circuit was flushed with PBS and no visible clotting was observed. Scanning electron microscopy of the oxygenator membrane shows that there was no microscopic fibrin deposition and minimal cellular adhesion to the membrane (FIG. 25A).

In contrast to UFH, no single aptamer prevented clot formation in the circuit. Macroscopic clots were formed either within the reservoir, on the oxygenator membrane, or at both sites within 2 hours (data not shown). Compared to the average donor baseline ACT+ clot time of 115 sec, 9.3T anticoagulation had no effect, 11F7T increased the ACT+ to a maximum of 213 seconds, and R9D-14T increased the ACT+ to a maximum of 365 seconds (data not shown). Interestingly, while in some experiments the clotting time returned to baseline values around the time of clot formation, in other experiments the clotting times exceeded the assay maximum. It is possible that extensive clot formation within the circuits consumed the clotting factors, and the elevated clotting times observed with these circuits may reflect a state of consumptive coagulopathy. Scanning electron micrographs of the oxygenator membrane from minicircuits anticoagulated with 9.3T, 11F7T, or R9D-14T show obvious fibrin deposition on the membrane (FIGS. 25B, 25C and 25D), indicating that none of these anticoagulants provides a satisfactory degree of anticoagulation for extracorporeal circulation.

Because UFH anticoagulates blood by inhibiting several procoagulant enzymes, it was hypothesized that combinations of anticoagulant aptamers could more effectively mimic UFH anticoagulation in the ex vivo circuit than single aptamers. The three potent aptamer combinations that kept whole blood fluid in a TEG for greater than three hours (9.3T+11F7T, 9.3T+R9D-14T, and 11F7T+R9D-14T) were tested in the ex vivo circuit. 9.3T+11F7T failed in the ex vivo circuit as there was macroscopic clotting in the reservoir and on the oxygenator membrane after the blood was circulated for 2 hours and the circuit was flushed with saline (data not shown). This combination increased the ACT+ from an average baseline of 115 seconds to a maximum of 205 seconds. 9.3T+R9D-14T also failed again as there was visible clotting on the oxygenator membrane after the blood was circulated for 2 hours and the circuit was subsequently flushed with saline (data not shown). This aptamer combination increased the ACT+ clotting to a maximum of 368 seconds.

In contrast, 11F7T+R9D-14T prevented clot formation in the circuit for greater than 2 hours in independent experiments with blood from three different donors. This combination prolonged the ACT+ clotting time from an average of 115 seconds (donor baseline) to a maximal time of 462 seconds. Scanning electron micrographs of the oxygenator membrane with 11F7T+R9D-14T show minimal fibrin deposition and cellular adhesion, similar to the UFH heparin control membrane (FIG. 25E). Thus, a synergistic combination of the FXa and prothrombin aptamers can emulate UFH and robustly anticoagulate human blood during circulation in an extracorporeal bypass circuit.

Antidote Reversal of the 11F7T+R9D-14T Synergistic Combination:

With the exception of UFH, aptamers are the only rapid onset anticoagulants whose anticoagulant effects are directly neutralizable/reversible. Two independent methods of anticoagulant aptamer control have been described previously, with either a complementary oligonucleotide antidote (Rusconi et al, Nature 419: 90-4 (2002)) or a universal antidote (Oney et al, Nat Med 15:1224-8 (2009)). Clinical data to date indicate that antidote modulation of an aptamer anticoagulant is rapid and safe. Because the data here show that aptamer combinations result in extremely robust anticoagulation, there was interest in showing that synergistic aptamer combinations can be effectively controlled with an antidote, thereby improving the drug safety profile. Therefore, an assessment was made of antidote reversal of the robust 11F7T+R9D-14T synergistic aptamer combination that was successful in the extracorporeal bypass circuit.

Whole blood was anticoagulated with 11F7T+R9D-14T at a dose that prevents clot formation for greater than three hours, and various antidotes were subsequently added after one hour to assess anticoagulation reversal and resulting clot formation. Both protamine and the β-cyclodextrin containing polymer (CDP) were tested for their ability to function as a universal antidote by simultaneously reversing both aptamers in combination (Oney et al, Nat Med 15:1224-8 (2009)). After anticoagulation with 11F7T+R9D-14T for 1 hour, a 4-fold molar excess of protamine (22 μM) resulted in stable clot formation within an average of 15 minutes (FIG. 26B), while CDP (50 μg) reversed anticoagulation and resulted in stable clot formation within an average of 10 minutes (FIG. 26C). Additionally, an antidote oligonucleotide cocktail containing a 3-fold molar excess of the 11F7T antidote oligonucleotide and a 2-fold molar excess of the R9D-14T antidote oligonucleotide reversed anticoagulation and resulted in clot formation within an average of 10 minutes (FIG. 26D). Thus, although the 11F7T+R9D-14T aptamer combination is an extremely potent anticoagulant cocktail that can mimic UFH anticoagulation in an ex vivo oxygenator circuit, the aptamer combination can be rapidly reversed with either a universal antidote or a combination of oligonucleotide antidotes.

Summarizing, heart disease, which is intimately related to thrombosis, is currently the leading cause of morbidity and mortality in the western world (Roger et al, Circulation 123:e18-e209 (2011)). Surgical intervention is often required to treat thrombosis and restore blood flow, and challenging surgical settings, such as coronary artery surgery supported by cardiopulmonary bypass (CPB) represent extremely thrombogenic environments that require robust anticoagulation. However, anticoagulation must be controllable in the event of complications, such as hemorrhage (Levi et al, J Thromb Haemost 9:1705-1712 (2011)). Because the current standard of care for bypass anticoagulation (unfractionated heparin, UFH, with protamine reversal) has a number of untoward side effects (Warkentin, Hematol Oncol Clin North Am 21:589-607 (2007), Wakefield et al, Surgery 119:123-128 (1996), Oe et al, J Thorac Cardiovasc Surg 112:462-471 (1996), Hird et al, Circulation 92:11433-446 (1995), Takenoshita et al, Anesthesiology 84:233-235 (1996)), new effective antidote-controllable anticoagulants with improved safety profiles are needed. It has been previously shown that modified RNA aptamers can bind to coagulation proteins and bury a large surface area, thereby inhibiting protein-protein interactions that are essential for coagulation (Buddai et al, J. Biol. Chem. 285:5212-5223 (2010), Long et al, RNA 14:1-9 (2008), Bompiani et al, J. Thromb. Haemost. 10:870-80 (2012), Sullenger et al, J. Biol. Chem. 287:12779-86 (2012)). Moreover, these aptamers can be functionally modulated with antidotes, resulting in anticoagulation that can be controlled by physicians as required (Rusconi et al, Nature 419:90-94 (2002), Bompiani et al, J. Thromb. Haemost. 10:870-80 (2012)).

The data here indicate that the individual aptamers each have a unique dose-dependent impact on thrombin generation and clot formation in various in vitro assays. Although all of the aptamers specifically bind to their therapeutic target with low-nanomolar binding affinities (Rusconi et al, Nature 419:90-94 (2002), Layzer and Sullenger, Oligonucleotides 17:1-11 (2007), Buddai et al, J. Biol. Chem. 285: 5212-5223 (2010), Bompiani et al, J. Thromb. Haemost. 10:870-80 (2012)), the in vitro plasma data indicate that to produce optimal anticoagulation, enough aptamer must be titrated in to a concentration that saturates the protein target in plasma. For example, although R9D-14T binds to human prothrombin with an apparent Kd of 10 nM (Bompiani et al, J. Thromb. Haemost. 10:870-80 (2012)), micromolar concentrations are required to saturate prothrombin, which has an estimated concentration of 1.4 μM in human plasma. As can be predicted based upon the plasma protein concentrations of the four coagulation factors studied here, lower concentrations of aptamers targeting "upstream" coagulation factors (i.e., FVII and FIX) are required for saturation compared to aptamers targeting "downstream" coagulation factors (i.e., FX and prothrombin). However, the data indicate that aptamers targeting upstream proteins (i.e., 7S-1 and 9.3T) are only able to partially impair clot formation and reduce thrombin generation, while aptamers targeting downstream proteins (11F7T and R9D-14T) have a more robust effect. For example, the FVIIa aptamer (7S-1) has only a modest effect on thrombin generation/clot formation in the PT, CAT, and TEG assays, even with TF stimulation via the "extrinsic" pathway. The anticoagulant mechanism for this aptamer has not been studied, and it is possible that the aptamer only partially blocks either FVII activation or FVIIa activity and thus only partially reduces thrombin generation. Moreover, it is currently unclear why the anticoagulation effect of this aptamer appears to vary from donor to donor. Additional studies are needed to determine whether this variability is due to differences in the 7S-1 binding affinity to FVII/VIIa from the different donors, or whether FVII/VIIa inhibition itself produces variable donor-specific anticoagulation.

Clinical studies have shown that the FIXa aptamer (9.3T) generates a Hemophilia B-like state by inhibiting greater than 99% of FIXa activity in vivo (Povsic et al, Eur Heart J 32:2412-9 (2011). Moreover, this aptamer/antidote pair sufficiently anticoagulated blood in a model of neonatal porcine cardiopulmonary bypass (Nimjee et al, Mol Ther 14:408-415 (2006)). However, the data clearly show that this aptamer has a limited anticoagulant effect in the presence of high TF and may, therefore, be less effective for treating clinical indications that are associated with high levels of TF, such as atherosclerotic plaque formation and rupture. Although it is commonly believed that coagulation is mainly initiated by the contact/intrinsic pathway during extracorporeal circulation (Wachtfogel et al, Blood 73:468-471 (1989), Fuhrer et al, Adv Exp Med Biol 198 (Pt B):385-391 (1986), Wachtfogel et al, J Thorac Cardiovasc Surg 106:1-9 discussion—10 (1993)), several studies have indicated that TF stimulation also plays a major role (Burman et al, Lancet 344:1192-1193 (1994), Kappelmayer et al, Circ Res 72:1075-1081 (1993), Boisclair et al, Blood 82:3350-3357 (1993)). Correspondingly, 9.3T cannot sufficiently anticoagulate human blood during ex vivo extracorporeal circulation and may, therefore, not be ideal for CPB anticoagulation.

Strikingly, no individual aptamer was able to prevent clot formation in the ex vivo circuit, which indicates that inhibiting one coagulation protein is not sufficient for extracorporeal circulation anticoagulation. The current regimen for cardiopulmonary bypass (UFH) anticoagulates blood by inhibiting several coagulation factors (i.e., FIXa, FXa, and thrombin) (Bedsted et al, Biochemistry 42:8143-8152 (2003), Olson et al, J Biol Chem 267:12528-12538 (1992), Beeler et al, J., Biol Chem 254:2902-2913 (1979)); therefore, it is hypothesized that a combination of anticoagulant aptamers may better mimic heparin anticoagulation. Interestingly, although some of the aptamer cocktails resulted in synergistic anticoagulation in vitro, several aptamer combinations were not synergistic. Aptamer combinations that inhibit two non-sequential enzymatic reactions (i.e., 7S-1+R9D-14T) appeared less synergistic compared to combinations that inhibit sequential steps were synergistic (i.e., FX+FII). However, of the three synergistic aptamer combinations that were tested in the ex vivo circuit, only the 11F7T+R9D-14T combination was successful and prevented fibrin deposition on the oxygenator membrane for the duration of the experiment. This combination may be optimal because it inhibits the only two non-redundant steps in coagulation, rather than pathway specific steps. Mechanistic studies with these two individual aptamers indicate that this drug combination blocks FX cleavage (by the intrinsic, but not extrinsic tenase complex), FXa activity, prothrombin cleavage, and thrombin exosite I function (Buddai et al, J. Biol. Chem. 285:5212-5223 (2010)) (Bompiani et al, J. Thromb. Haemost. 10:870-80 (2012)). This, this powerful combination severely impairs thrombin generation by inhibiting multiple crucial enzymatic reactions.

Although there are currently a number of anticoagulant and antiplatelet agents available, many of these drugs do not produce an optimal level of anticoagulation for extracorporeal bypass circulation and/or cannot be controlled with an antidote (Murphy and Marymont, J. Cardiothorac Vasc Anesth 21:113-126 (2007)). Current antithrombotics are not typically used in combination because of their potential uncontrollable drug synergy. In contrast, the present data show that a powerful aptamer cocktail (11F7T+R9D-14T) can effectively anticoagulate blood and be rapidly and safely controlled with either a universal antidote, or a cocktail of matched oligonucleotide antidotes. Thus, aptamers represent a unique class of therapeutics that can be combined to produce synergistic anticoagulation by inhibiting multiple proteins within coagulation, yet can be rapidly modulated with an antidote. These aptamer cocktails, in conjunction with antidotes, represent the first attractive strategy for cardiopulmonary bypass circulation since the development of unfractionated heparin/protamine. Furthermore, based on their unique ability to be used alone or in combination, yet safely modulated with an antidote, indicate that aptamers have broad clinical applicability for thrombosis treatment.

Example IV

A series of bifunctional or "dogbone" aptamer combinations were created which are single molecules that contain binding sites for both FIX and FX or FX and FII. The starting dogbones varied in the length of the stems and flexible linker regions between each aptamer (FIG. 27). The dogbones were compared to the free combination of aptamers in an aPTT assay to determine any differences in functionality. For the FIX/FX combination, dogbones 1 and 2 show equal anti-coagulation compared to the free combination (FIG. 28, upper panel). As seen in the lower panel of FIG. 28, with the FX/FII combination dogbones 1 and 3 shows better anti-coagulation when compared to the free aptamers.

Additional data from another project revealed the FX/FII combination was superior to the FIX/FX combination in a small ex vivo circuit used to mimic cardio-pulmonary bypass. Because of this, the decision was made to move forward with additional testing and refinement of the FX/FII dogbone combination.

Figure 29A:
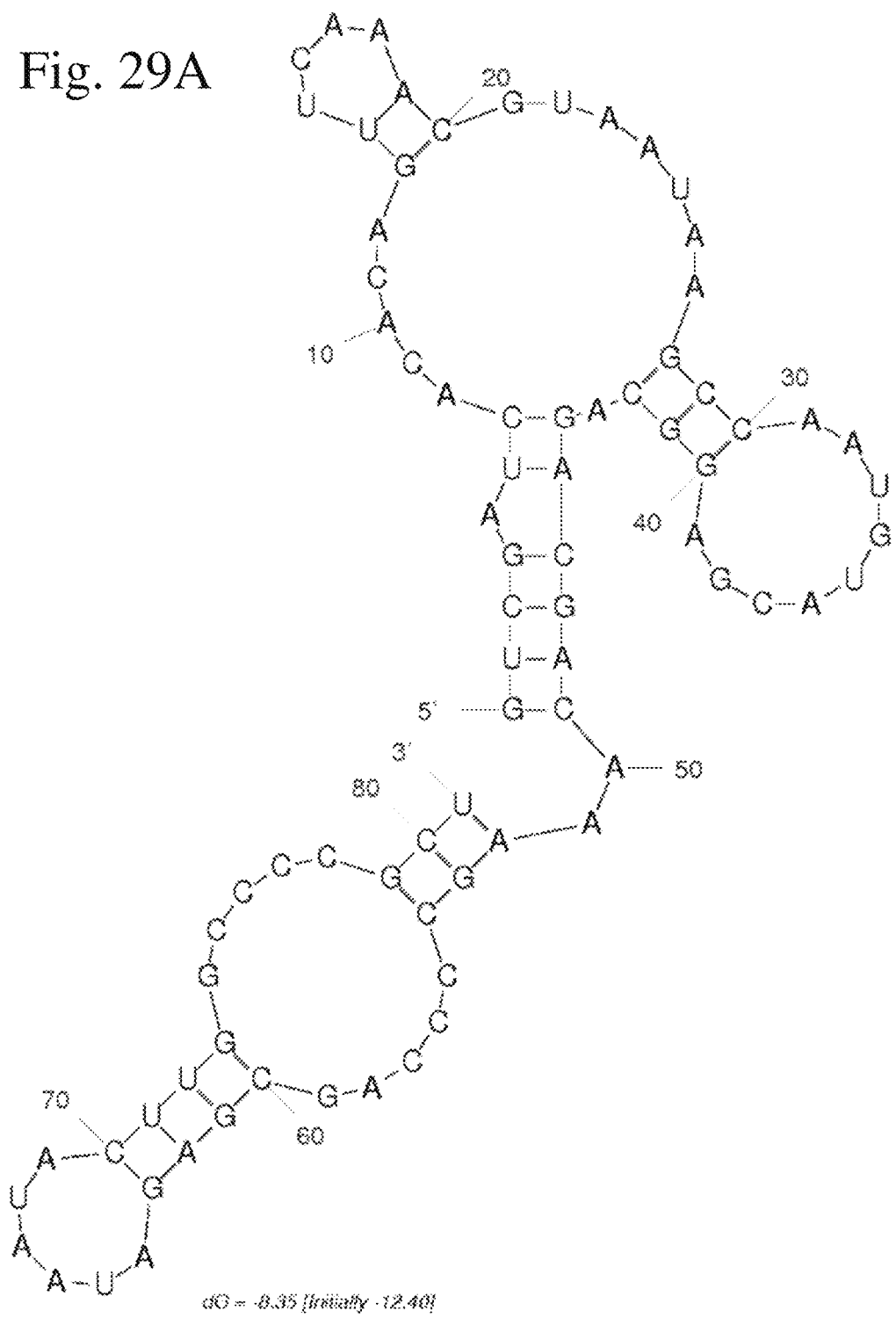
FIGS. 29A-29C: FX/FII Dogbone 4 and Truncates.
Figure 29B:
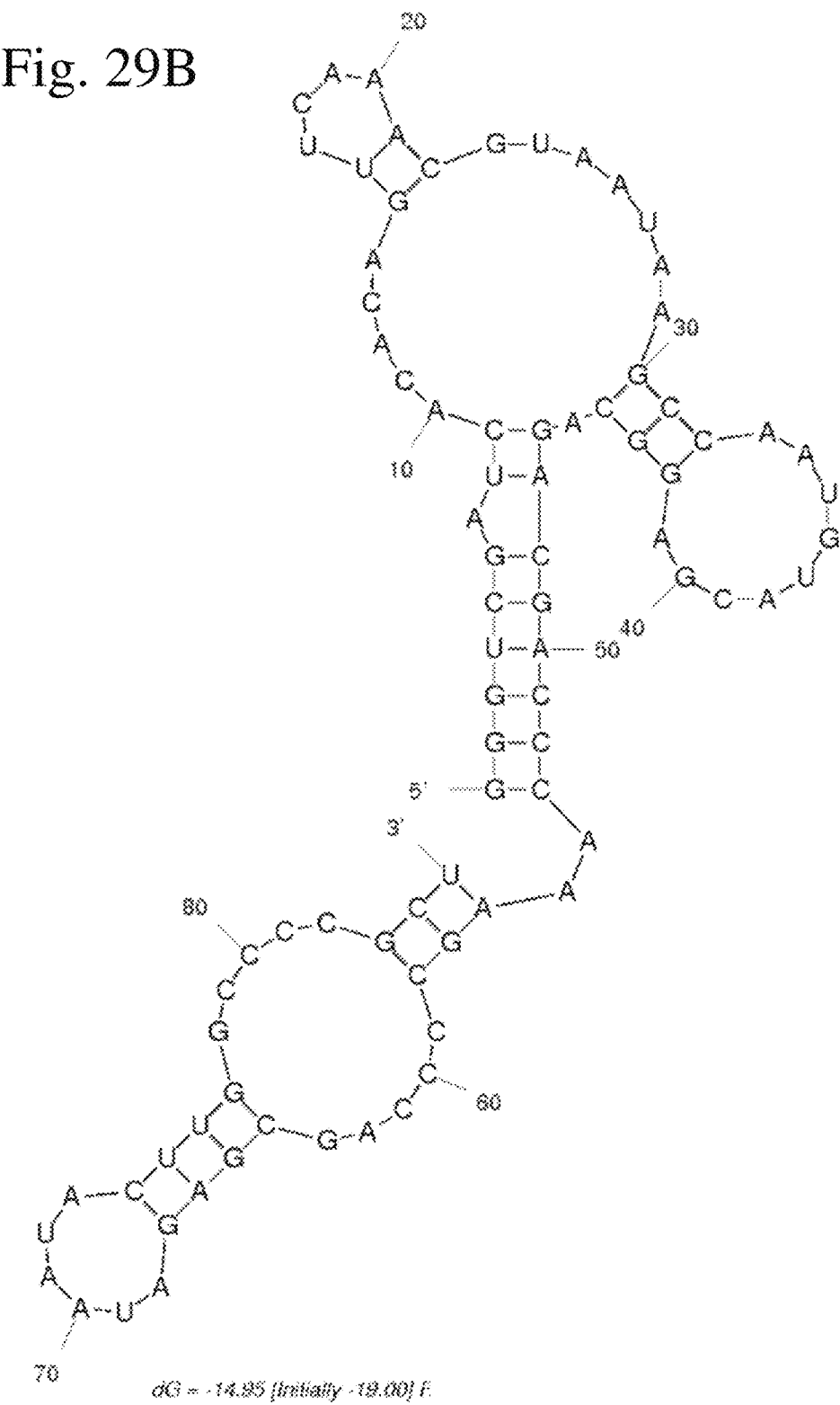
Figure 29C:
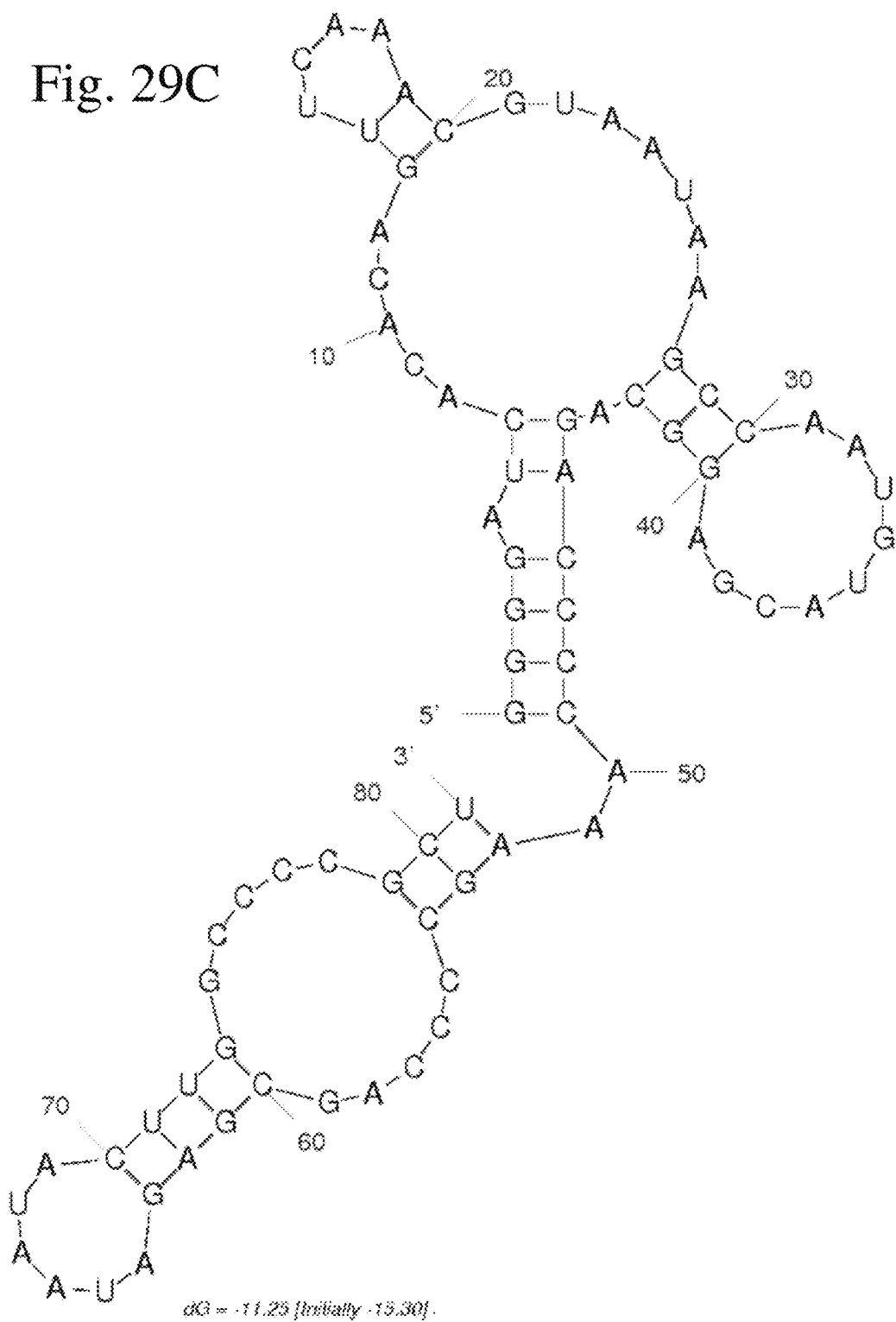

Truncation is an important part of aptamer development. An effort was made to reduce the size of the FX/FII dogbone so it is more cost-effective to create on a large scale. This led to the creation of dogbone 4 and a variety of truncates from this structure (FIG. 29). Testing for functionality in an aPTT indicated the 3G and 4G versions of dogbone 4 had the best anti-coagulation activity of the truncates (FIG. 30).

Reversibility of the aptamers is a major benefit of this class of drugs. The antidotes are generated based on Watson-Crick base pairing making their activity highly specific. It was found that generating aptamers with one of the aptamers mutated reduces the activity of the bone, leaving the other aptamer functional (FIG. 31). Additionally, single antidote was created that can reverse the inhibitory effect of both ends of the dogbone at the same time. The antidote sequences were based off the original sequence for dogbone 4 (FIG. 32, upper panel) and, despite imperfect base-pairing, show significant reversal of 4G dogbone 4 activity (FIG. 32, lower panel). Thus a single antidote oligonucleotide that recognizes the linker between aptamers present in a dogbone configuration can surprisingly reverse the activity of both aptamers on the ends of the dogbone structure.

Activity of dogbone 4 was tested using thromboelastography (TEG), an assay using whole human blood. It was found that FX/FII dogbone 4 both have comparable or better activity than the free combination of aptamers (FIG. 33).

All documents and other information sources cited herein are hereby incorporated in their entirety by reference.

What is claimed is:

1. A composition comprising at least two agents that directly inhibit more than one step in a coagulation pathway and a carrier, wherein one of the agents is capable of inhibiting Factor X or Factor Xa and the other agent is capable of inhibiting prothrombin or thrombin, wherein the agents are aptamers and the aptamers are 11F7T (SEQ ID NO:2) and R9D-14T (SEQ ID NO: 3 or 13).

2. A composition comprising two agents that each directly inhibit a different step in a coagulation pathway and a carrier, wherein the agents are aptamers and the aptamers are linked to form a single nucleic acid molecule, and wherein the aptamers are 11F7T (SEQ ID NO: 2) and R9D-14T (SEQ ID NO: 3 or 13).

3. The composition of claim 2, wherein the aptamers comprise a nucleic acid sequence selected from the group consisting of SEQ ID NOs: 19-24.

4. A method of controlling coagulation comprising administering to a subject in need thereof the composition of claim 2 in an amount sufficient to control coagulation.

5. The method according to claim 4, wherein said subject is a surgery patient or the subject suffers from stroke or deep vein thrombosis.

6. The method according to claim 4, wherein said subject is undergoing cardiopulmonary bypass surgery or percutaneous coronary intervention.

7. The method of claim 4, wherein the aptamers comprise a nucleic acid sequence selected from the group consisting of SEQ ID NOs: 19-24.

8. The composition of claim 1, wherein at least one of the aptamers may be neutralized by an aptamer-specific antidote oligonucleotide or a nucleic acid binding polymer.

9. The composition of claim 8, wherein the nucleic acid binding polymer is protamine or a cyclodextrin-containing polycation (CDP).

10. The composition of claim 1, wherein the aptamers are linked to form a single nucleic acid molecule comprising a nucleic acid sequence selected from the group consisting of SEQ ID NOs: 19-24.

11. A method of controlling coagulation comprising administering to a subject in need thereof the composition of claim 1 in an amount sufficient to control coagulation.

12. The method of claim 11, wherein said subject is a surgery patient or suffers from stroke or deep vein thrombosis.

13. The method of claim 11, wherein the aptamers are linked to form a single nucleic acid molecule comprising a nucleic acid sequence selected from at least one of SEQ ID NOs: 19-24.

14. A composition comprising two agents that each directly inhibit a different step in a coagulation pathway and a carrier, wherein the agents are aptamers and the aptamers are linked to form a single nucleic acid molecule, and wherein the aptamers comprise a nucleic acid sequence selected from the group consisting of SEQ ID NOs: 15-24.

15. A method of controlling coagulation comprising administering to a subject in need thereof the composition of claim 14 in an amount sufficient to control coagulation.

16. The method of claim 15, wherein said subject is a surgery patient or suffers from stroke or deep vein thrombosis.

17. The method according to claim 16, wherein said subject is undergoing cardiopulmonary bypass surgery or percutaneous coronary intervention.

* * * * *